US008097620B2

(12) United States Patent
Allen et al.

(10) Patent No.: US 8,097,620 B2
(45) Date of Patent: Jan. 17, 2012

(54) DIAZAQUINOLONES THAT INHIBIT PROLYL HYDROXYLASE ACTIVITY

(75) Inventors: Jennifer R. Allen, Newbury Park, CA (US); Kaustav Biswas, Pasadena, CA (US); Roland Burli, Bishop's Shortford (GB); Jennifer E. Golden, Simi Valley, CA (US); Stephanie Mercede, Thousand Oaks, CA (US); Christopher M. Tegley, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 877 days.

(21) Appl. No.: 12/150,998

(22) Filed: May 2, 2008

(65) Prior Publication Data
US 2009/0099171 A1 Apr. 16, 2009

Related U.S. Application Data

(60) Provisional application No. 60/927,748, filed on May 4, 2007.

(51) Int. Cl.
C07D 471/04 (2006.01)
C07D 413/14 (2006.01)
A61K 31/519 (2006.01)
A61K 31/5355 (2006.01)
A61P 3/10 (2006.01)
A61P 35/00 (2006.01)
A61P 29/00 (2006.01)

(52) U.S. Cl. .................. 514/234.2; 514/264.1; 544/279; 544/117

(58) Field of Classification Search ............ 514/234.2, 514/264.1; 544/279, 117
See application file for complete search history.

(56) References Cited

U.S. PATENT DOCUMENTS

| 3,954,733 | A | 5/1976 | Tobiki et al. |
| 3,992,371 | A | 11/1976 | Tobiki et al. |
| 4,215,123 | A | 7/1980 | Scotese et al. |
| 4,374,138 | A | 2/1983 | Haskell et al. |
| 4,382,089 | A | 5/1983 | Haskell et al. |
| 4,404,201 | A | 9/1983 | Haskell et al. |
| 4,468,394 | A | 8/1984 | Machida et al. |
| 4,710,473 | A | 12/1987 | Morris |
| 5,037,826 | A | 8/1991 | Blythin et al. |
| 5,126,341 | A | 6/1992 | Suzuki et al. |
| 5,378,679 | A | 1/1995 | Nuebling et al. |
| 5,502,035 | A | 3/1996 | Haviv et al. |
| 5,620,995 | A | 4/1997 | Weidmann et al. |
| 5,719,164 | A | 2/1998 | Weidmann et al. |
| 5,798,451 | A | 8/1998 | von Deyn et al. |
| 5,972,841 | A | 10/1999 | von Deyn et al. |
| 6,093,730 | A | 7/2000 | Weidmann et al. |
| 6,593,343 | B2 | 7/2003 | Björk et al. |
| 6,787,326 | B1 | 9/2004 | Ratcliffe et al. |
| 2003/0153503 | A1 | 8/2003 | Klaus et al. |
| 2004/0235082 | A1 | 11/2004 | Fourney et al. |
| 2004/0254215 | A1 | 12/2004 | Arend et al. |
| 2005/0020487 | A1 | 1/2005 | Klaus et al. |
| 2005/0107364 | A1 | 5/2005 | Hutchinson et al. |
| 2006/0216295 | A1 | 9/2006 | Crabtree et al. |
| 2006/0251638 | A1 | 11/2006 | Guenzler-Pukall et al. |
| 2006/0276477 | A1 | 12/2006 | Klaus et al. |
| 2007/0004627 | A1 | 1/2007 | Seeley et al. |
| 2007/0203174 | A1 | 8/2007 | Klimko et al. |
| 2007/0249605 | A1 | 10/2007 | Allen et al. |
| 2008/0171756 | A1 | 7/2008 | Shaw et al. |
| 2009/0082357 | A1 | 3/2009 | Fitch et al. |
| 2010/0093738 | A1* | 4/2010 | Muller et al. ............... 514/243 |
| 2010/0216799 | A1* | 8/2010 | Gore et al. ............... 514/248 |
| 2010/0280008 | A1 | 11/2010 | Deak et al. |
| 2010/0282228 | A1* | 11/2010 | Al-Garni et al. ............ 124/59 |
| 2011/0046112 | A1* | 2/2011 | Ackermann et al. ..... 514/211.09 |
| 2011/0065714 | A1* | 3/2011 | Golding et al. ........... 514/249 |

FOREIGN PATENT DOCUMENTS

| AT | 328085 | 3/1976 |
| EP | 0 500 297 A1 | 8/1992 |
| EP | 0 503 844 A1 | 9/1992 |
| EP | 0 937 459 A2 | 8/1999 |
| EP | 0 547 708 B1 | 2/2003 |
| EP | 1 541 558 A1 | 8/2003 |
| EP | 1 538 160 A1 | 6/2005 |
| GB | 1 449 256 | 9/1976 |
| JP | 493592 A | 4/1974 |
| JP | 7224040 A2 | 8/1995 |
| SU | 1735288 | 5/1992 |

(Continued)

OTHER PUBLICATIONS

Vippagunta, S.R. et al. "Crystalline Solids," Advanced Drug Delivery Reviews, 48, pp. 3-26 (2001).
Lala, P. K. et al. "Role of nitric oxide in tumor progression: Lessons from experimental tumors," Cancer and Metastasis Reviews, 17, pp. 91-106, (1998).
Golub, T. R. et al. "Molecular Classification of Cancer: Class Discovery and Class Prediction by Gene Expression Monitoring", Science, 286, pp. 531-537 (1999).
Prosecution History of U.S. Appl. No. 12/002,538 Without References, From Dec. 17, 2007 to Jun. 17, 2011.

(Continued)

Primary Examiner — James O Wilson
Assistant Examiner — Cecilia M Jaisle
(74) Attorney, Agent, or Firm — Bernard P. Friedrichsen

(57) ABSTRACT

Compounds of Formula I are useful inhibitors of HIF prolyl hydroxylases. Compounds of Formula I have the following structure:

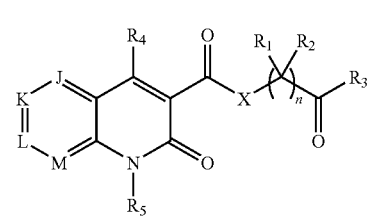

where the definitions of the variables are provided herein.

62 Claims, 5 Drawing Sheets

FOREIGN PATENT DOCUMENTS

| WO | WO 01/85732 A1 | 11/2001 |
|---|---|---|
| WO | WO 02/24679 A1 | 3/2002 |
| WO | WO 02/076396 A2 | 10/2002 |
| WO | WO 03/053997 A2 | 7/2003 |
| WO | WO 2004/037853 A2 | 5/2004 |
| WO | WO 2004/103974 A1 | 12/2004 |
| WO | WO 2004/104000 A1 | 12/2004 |
| WO | WO 2004/108121 A1 | 12/2004 |
| WO | WO 2004/108681 A1 | 12/2004 |
| WO | WO 2005/011696 A1 | 2/2005 |
| WO | WO 2005/021546 A1 | 3/2005 |
| WO | WO 2005/047285 A1 | 5/2005 |
| WO | WO 2005/077050 A2 | 8/2005 |
| WO | WO 2005/111044 A1 | 11/2005 |
| WO | WO 2006/088246 A1 | 8/2006 |
| WO | WO 2006/094292 A2 | 9/2006 |
| WO | WO 2007/038571 A2 | 4/2007 |
| WO | WO 2007/070359 A2 | 6/2007 |
| WO | WO 2007/097929 A1 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/040002 A2 | 4/2008 |

OTHER PUBLICATIONS

Prosecution History of U.S. Appl. No. 11/635,683 Without References, From Dec. 8, 2006 to Aug. 2, 2010.
Prosecution History of U.S. Appl. No. 12/703,496 Without References, From Feb. 10, 2010 to May 16, 2011.
Prosecution History of U.S. Appl. No. 12/703,716 Without References, From Feb. 10, 2010 to May 17, 2011.
Prosecution History of U.S. Appl. No. 12/002,537 Without References, From Dec. 17, 2007 to De. 22, 2009.
Prosecution History of U.S. Appl. No. 12/612,465 Without References, From Nov. 4, 2009 to Apr. 19, 2011.
Prosecution History of U.S. Appl. No. 12/082,263 Without References, From Apr. 9, 2008 to Aug. 4, 2009.
Prosecution History of U.S. Appl. No. 12/148,179 Without References, From Apr. 16, 2008 to May 24, 2011.
Prosecution History of U.S. Appl. No. 13/109,877 Without References, From May 17, 2011 to Jun. 9, 2011.
Prosecution History of U.S. Appl. No. 12/150,675 Without References, From Apr. 29, 2008 to Jun. 16, 2011.
U.S. Appl. No. 12/002,537, filed Dec. 17, 2007, Allen et al.
U.S. Appl. No. 12/002,538, filed Dec. 17, 2007, Allen et al.
U.S. Appl. No. 12/082,263, filed Apr. 9, 2008, Allen et al.
U.S. Appl. No. 12/148,179, filed Apr. 16, 2008, Allen et al.
U.S. Appl. No. 12/150,675, filed Apr. 29, 2008, Allen et al.
International Search Report from co-pending PCT Application No. PCT/US2008/005698 (WO 2008/137085 A3, first page and ISR) published on Nov. 13, 2008.
He, L. et al., "Probabilistic Neural Network Multiple Classifier System for Predicting the Genotoxicity of Quinolones and Quinoline Derivatives," Chem. Res. Toxicol. 18, pp. 428-440 (2005).
Ukrainets, I.V. et al., "4-Hydroxy-2-Quinolines. XXI. 1H-2-Oxo-4-Hydroxyquinoline-3-Carboxylic Alkylamides as a Novel Group of Antithyroid Drugs," Farmatsevtichnii Zhurnal (Kiev) 6, pp. 54-55 (1995).
Bezuglyi, P.A., "Amides of 4-Hydroxyquinoline-2-oxo-3-carboxylic Acid: Synthesis and Anticoagulant Activity," Khimiko-Farmatsevticheskii Zhurnal, 24(4) pp. 31-32 (1990). This document is in the Russian language-an English language abstract is included.
Schofield, C.J. et al., "Oxygen Sensing by HIF Hydroxylases", Nature Reviews, Molecular Cell Biology, 5(5), pp. 243-254 (2004).
McDowell, R. S. et al., "From Peptide to Non-Peptide. 2. The De Novo Design of Potent, Non-peptidal Inhibitors of Platelet Aggregation Based on a Benzodiazepinedione Scaffold," J. Am. Chem. Soc. 116(12) pp. 5077-5083 (1994).
Bohnert et al., "Redox Reactions with Cyclopeptide-Like Quinoline Derivatives as Lipophilic, Masked NAD Model Compounds," Zeitschrift für Naturforschung, B.: Chemical Sciences, 42(9) pp. 1159-1166 (1987). This document is in the German language-an English language abstract is included.
Kath, J.C. et al., Potent Small Molecule CCR1 Antagonists, Bioorg & Med. Chem. Letters, 14(9), pp. 2169-2173 (2004).
Ukrainets, I.V. et al., "4-Hydroxy-2-Quinolones. 4. Selection of the Optimum Path for Synthesis of N-R-Substituted 4-Hydroxy-2-Quinolone-3-Carboxylic Acid Amides." Chemistry of Heterocyclic Compounds 28(5), pp. 538-540 (1992).
Warshakoon, N.C. et al., "Design and Synthesis of a Series of Novel Pyrazolopyridines as HIF 1-α Prolyl Hydroxylase Inhibitors," Bioorg & Med. Chem. Letters, 16, pp. 5687-5690 (2006).
Warshakoon, N.C. et al., "Structure-Based Design, Synthesis, and SAR Evaluation of a New Series of 8-Hydroxyquinolinse as HIF-1α Prolyl Hydroxylase Inhibitors," Bioorg & Med. Chem. Letters, 16, pp. 5517-5522 (2006).
Warshakoon, N.C. et al., "A Novel Series of Imidazo[1,2-a]pyridine Derivatives as HIF-1α Prolyl Hydroxylase Inhibitors," Bioorg & Med. Chem. Letters, 16, pp. 5598-5601 (2006).
McDonough, M.A. et al., "Cellular Oxygen Sensing: Crystal Structure of Hypoxia-Inducible Factor Prolyl Hydroxylase (PHD2)," Proc. Natl. Acad. Sci., 103(26) pp. 9814-9819 (2006).
Jönssen, S. et al., "Synthesis and Biological Evaluation of New 1,2-Dihydro-4-hydroxy-2-oxo-3-quinolinecarboxamides for Treatment of Autoimmune Diorders: Structure-Activity Relationship," J. Med. Chem. 47, pp. 2075-2088 (2004).
Buckle, D.R. et al., "Synthesis and Antiallergic Activity of 2-Hydroxy-3-nitro-1,4-naphthoquinones," J. Med. Chem. 20(8), pp. 1059-1064 (1977).
Franklin, T.J. et al., "Approaches to the Design of Anti-Fibrotic Drugs," Biochem. Soc. Trans. 19, pp. 812-815 (1991).

* cited by examiner

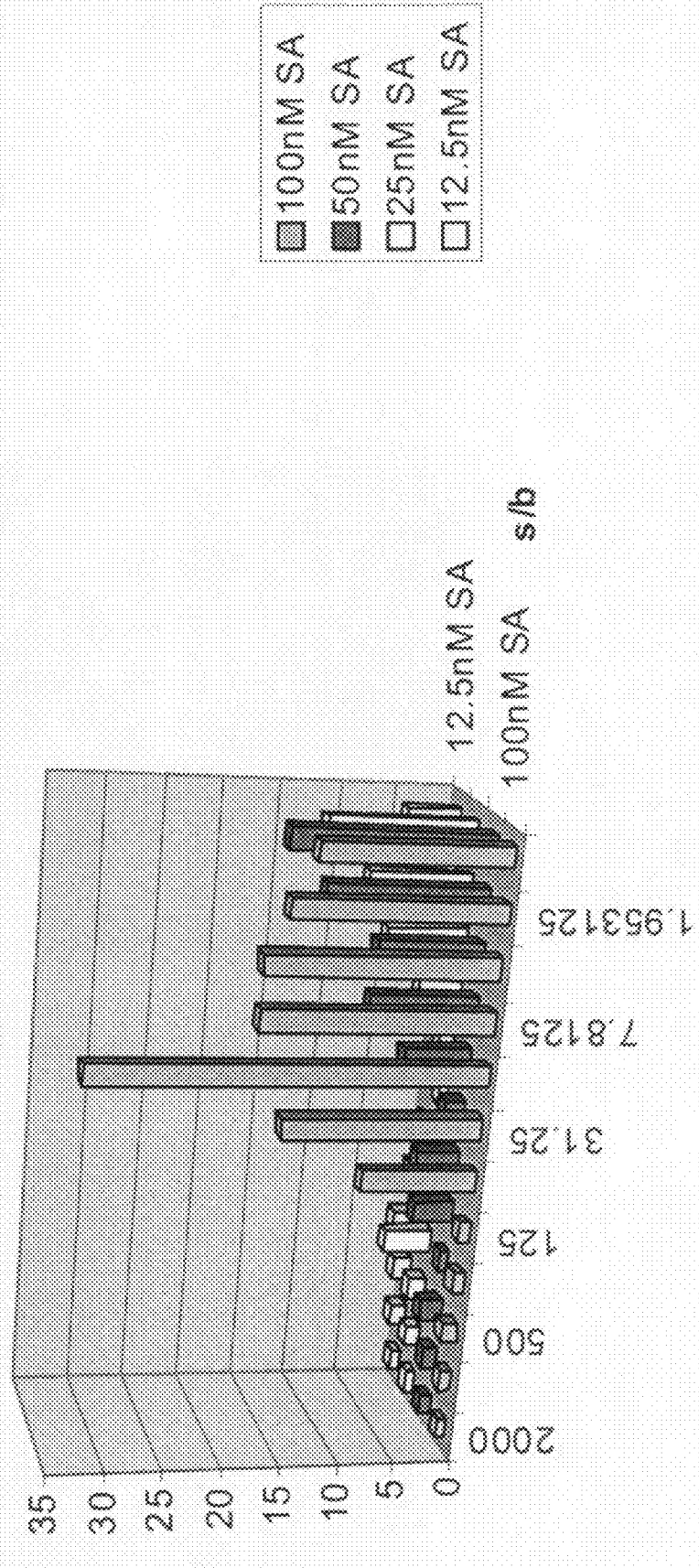

DIAZAQUINOLONES THAT INHIBIT PROLYL HYDROXYLASE ACTIVITY

CROSS REFERENCES TO RELATED APPLICATIONS

This application claims the benefit of U.S. Provisional Application No. 60/927,748, filed on May 4, 2007, which is hereby incorporated by reference in its entirety and for all purposes as if fully set forth herein.

FIELD OF THE INVENTION

The present invention relates to compounds capable of inhibiting prolyl hydroxylases such as HIF prolyl hydroxylases, compounds that modulate HIF levels, compounds that stabilize HIF, compositions comprising the compounds, and methods for their use for controlling HIF levels. The compounds and compositions may be used to treat diseases or conditions modulated by HIF such as ischemia, anemia, wound healing, auto-transplantation, allo-transplantation, xeno-transplantation, systemic high blood pressure, thalassemia, diabetes, cancer, and inflammatory disorders.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an αβ heterodimer: HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL) binds to hydroxylated HIF-α subunits, thereby promoting their ubiquitin dependent proteolysis. This process is suppressed under hypoxic conditions, stabilizing HIF-α and promoting transcriptional activation by the HIF αβ complex. See, e.g., U.S. Pat. No. 6,787,326.

Hydroxylation of HIF-α subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1α. Inhibition of FIH or the PHDs leads to HIF stabilization and transcriptional activation. See, e.g., Schofield and Ratcliffe, Nature Rev. Mol. Cell. Biol., Vol 5, pages 343-354 (2004).

SUMMARY OF THE INVENTION

In one aspect, the invention provides composition of matter that includes at least one compound of Formula I:

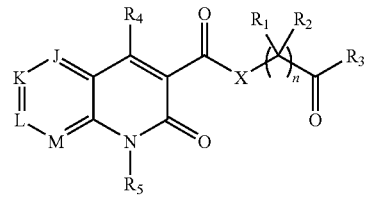

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J, K, L, and M are selected from $CR_6$ or N, wherein two of J, K, L, and M are N and the other two of J, K, L, and M are $CR_6$;

n is 1 to 6;

$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

X is selected from —$NR_a$—, —O—, or —S—, wherein $R_a$ is selected from H or lower alkyl;

$R_3$ is selected from OH, SH, $NH_2$, lower alkyl, substituted lower alkyl, lower alkoxy, substituted lower alkoxy, or sulfanyl;

$R_4$ is selected from H, OH, lower alkoxy, SH, $NH_2$, $NHSO_2R_7$, or sulfonyl;

$R_5$ is selected from H, lower alkyl, or substituted lower alkyl;

each $R_6$ is independently selected from H, F, Cl, Br, I, alkyl, substituted alkyl, haloalkyl, perhaloalkyl, alkenyl, substituted alkenyl, alkynyl, substituted alkynyl, $NR_dR_e$, $C(O)R_7$, $C(O)OR_8$, $OR_8$, $SR_8$, $SO_2R_8$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_9$, wherein:

Y is selected from —$N(R_{10})$—Z— or —Z—$N(R_{10})$—;

Z is selected from C(O), $SO_2$, alkylene, substituted alkylene, alkenylene, substituted alkenylene, alkynylene, or substituted alkynylene;

$R_7$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_8$ is selected from H, alkyl, substituted alkyl, alkenyl, substituted alkenyl, alkynyl, or substituted alkynyl;

$R_9$ is selected from H, heterocyclyl, substituted heterocyclyl, aryl, substituted aryl, heteroaryl, or substituted heteroaryl;

$R_{10}$ is selected from H, lower alkyl, or substituted lower alkyl; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments, M and L are N and J and K are $CR_6$. In other embodiments, M and K are N and J and L are $CR_6$. In still further embodiments, J and M are N and K and L are $CR_6$.

In some embodiments, $R_1$ and $R_2$ are not both H if X is —$NR_a$—; $R_a$ is H; and n is 1.

In some embodiments, n is 1, $R_1$ and $R_2$ are both H, X is —$NR_a$—; and $R_a$ is H.

In some embodiments, at least one of $R_1$ and $R_2$ is not H. In some such embodiments, at least one of $R_1$ and $R_2$ is a lower alkyl such as a ($C_1$-$C_4$)alkyl. In some such embodiments, one of $R_1$ and $R_2$ is H and the other of $R_1$ and $R_2$ is a lower alkyl. In some such embodiments, at least one of $R_1$ and $R_2$ is a methyl group, and in some such embodiments, the other of $R_1$ and $R_2$ is a methyl group.

In some embodiment, $R_3$ is OH.

In some embodiments, $R_4$ is selected from OH, SH, $NH_2$, $NHSO_2R_8$, or sulfonyl. In some such embodiments, $R_4$ is OH.

In some embodiments, X is —$NR_a$—. In some such embodiments, X is —NH—.

In some embodiments, at least one instance of $R_6$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_6$ is a heterocyclyl group. In other such embodiments, at least one instance of $R_6$ is a heteroaryl group. In other such embodiments, at least one instance of $R_6$ is a phenyl or substituted phenyl group.

In some embodiments, at least one instance of $R_6$ is independently selected from halo or a moiety substituted with at least one halo. For example, in some embodiments, at least one instance of $R_6$ is haloalkyl. In some embodiments, at least one instance of $R_6$ is a perhaloalkyl. In some such embodiments, the perhaloalkyl is a perfluoroalkyl group such as $CF_3$.

In some embodiments, n is 1.

In some embodiment, $R_1$ and $R_2$ are independently chosen from H and lower alkyl. In some such embodiments, $R_1$ and $R_2$ are both H. In some such embodiments, n is 1.

In some embodiments, n is 1; $R_1$ is H or lower alkyl; $R_2$ is H; $R_3$ is OH; $R_4$ is OH; X is —$NR_a$—; and $R_a$ is H.

In some embodiments of the compound of Formula I, $R_5$ is H. In other embodiments, $R_5$ is a lower alkyl group. In some such embodiments, $R_5$ is a methyl. In still other embodiments, $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

In some embodiments, the compound of Formula I has the Formula IA, and the variables have the definitions provided in any of the aspects and embodiments described above.

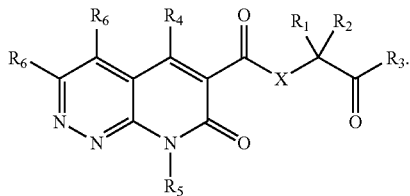

IA

In some embodiments, the compound of Formula I has the Formula IB, and the variables have the definitions provided in any of the aspects and embodiments described above.

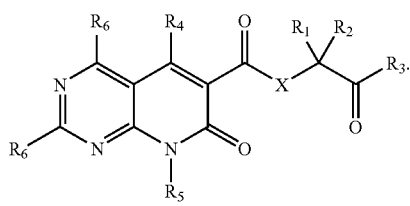

IB

In some embodiments, the compound of Formula I has the Formula IC, and the variables have the definitions provided in any of the aspects and embodiments described above.

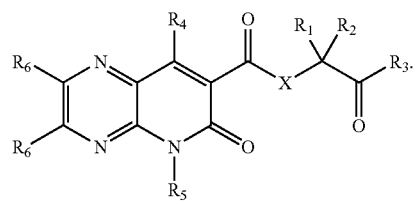

IC

In some embodiments, the composition of matter is a salt. Such salts may be anhydrous or associated with water as a hydrate.

In some embodiments, the composition of matter is a prodrug. In some such embodiments, the composition of matter is a ($C_1$-$C_6$)alkyl ester such as a methyl, ethyl, propyl, butyl, pentyl, or hexyl ester.

Also provided herein are pharmaceutical formulations that include at least one pharmaceutically acceptable carrier, excipient or diluent and a therapeutically effective amount of the composition of matter of any of the embodiments described herein. In such embodiments, the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical formulations that include at least one pharmaceutically acceptable carrier, and a therapeutically effective amount of the composition of matter of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject the composition of matter of any of the embodiments described herein.

Further provided is a method of treating a condition where it is desired to modulate HIF activity comprising administering to a subject the composition of matter of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject the composition of matter of any of the embodiments described herein.

Also provided is a method of treating anemia in a subject comprising administering to a subject the composition of matter of any of the embodiments described herein.

Further provided is a method of modulating the amount of HIF in a cell comprising contacting the cell with the composition of matter of any of the embodiments described herein.

Additionally provided is a method of increasing the amount of hemoglobin F in a subject comprising administering to the subject the composition of matter of any of the embodiments described herein.

Also provided is a method of modulating angiogenesis in a subject comprising administering to the subject the composition of matter of any of the embodiments described herein.

Additionally provided is a method of treating at least one disease in a patient in need of such treatment comprising administering to the patient a therapeutically effective amount of the composition of matter of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject the composition of matter n of any of the embodiments described herein.

In some embodiments, the HIF PHD inhibitory activity $IC_{50}$ value of the composition of matter is 40 µM or less. In other embodiments, the HIF PHD inhibitory activity $IC_{50}$ value of the composition of matter is 10 µM or less.

In some embodiments, the composition of matter of any of the embodiments is used in the preparation of a medicament.

In some such embodiments, the composition of matter of any of the embodiments is used in the preparation of a medicament for increasing or stabilizing HIF levels or activity in a subject.

In some such embodiments, the composition of matter of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the composition of matter of any of the embodiments is used in the preparation of a medicament for treating a hypoxic or ischemic related disorder in a subject.

In some embodiments, the composition of matter of any of the embodiments is used in the preparation of a medicament for modulating the amount if HIF in a cell. In some embodiments, the composition of matter according to any of the embodiments is used to modulate the amount of HIF in a cell.

In some embodiments, the composition of matter of any of the embodiments is used in the preparation of a medicament for modulating angiogenesis in a subject.

In some embodiments, the composition of matter of any of the embodiments is used in the preparation of a medicament for inhibiting HIF hydroxylation in a subject.

In some embodiments, the composition of matter of any of the embodiments is used in the preparation of a medicament for treating anemia.

In some embodiments, the composition of matter of any of the embodiments is used in a method for increasing the level of erythropoietin in the blood of a subject.

Other objects, features and advantages of the invention will become apparent to those skilled in the art from the following description and claims.

BRIEF DESCRIPTION OF THE DRAWINGS

FIG. 1 is a graph illustrating the ratio of fluorescence signal to background generated by the interaction of Eu-VCB with streptavidin-APC-hydroxypropyl HIF1α peptide.

FIG. 2A illustrates a 0-125 nM peptide range and FIG. 2B illustrates a 0-10 nM peptide range.

FIG. 3A illustrates a time course for the hydroxylation of the HIF1α peptide with increasing amounts of HIF PHD2 enzyme. FIG. 3B illustrates initial rates with increasing enzyme concentrations.

DETAILED DESCRIPTION OF THE INVENTION

Figure 2A:
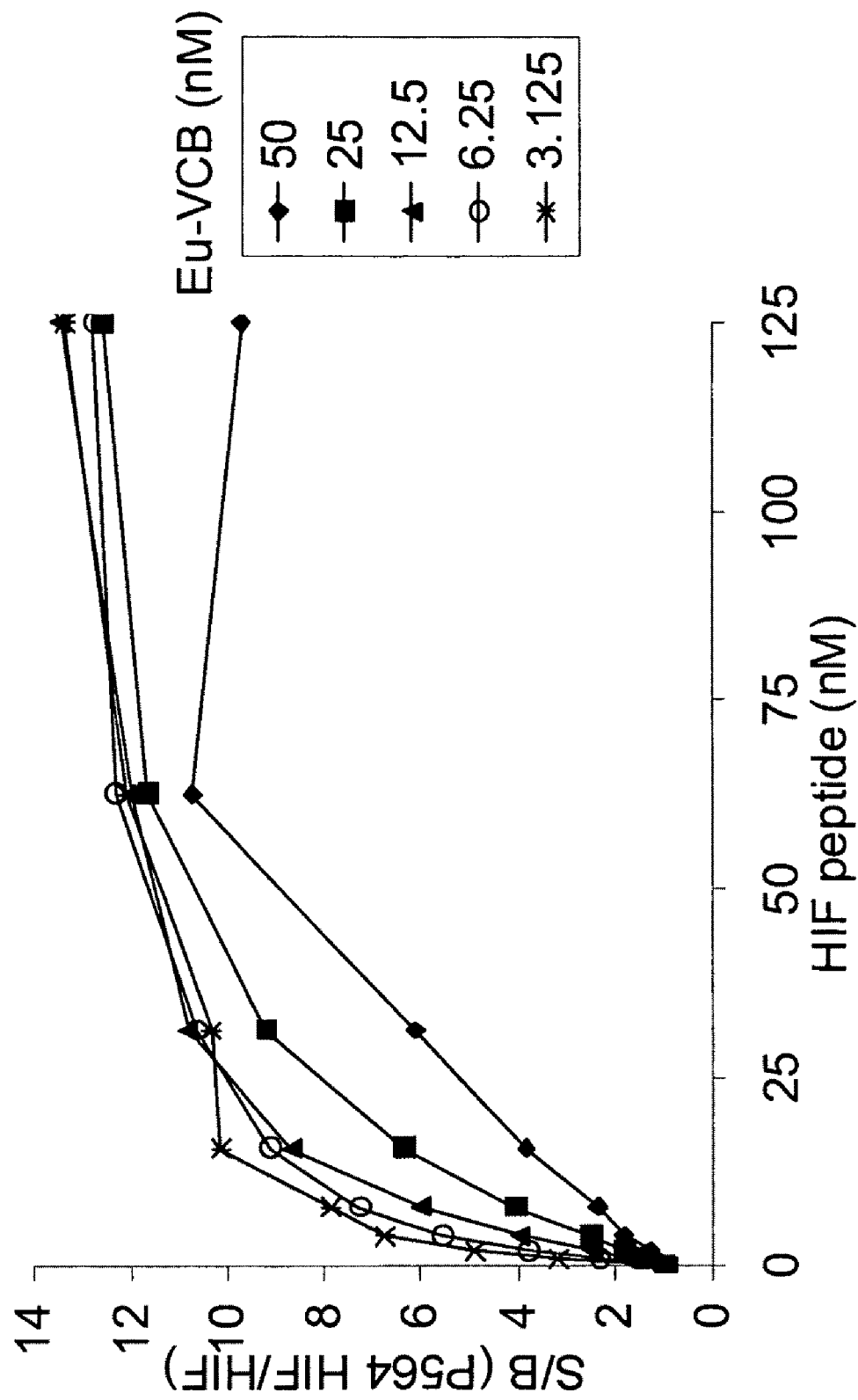
FIGS. 2A and 2B are graphs illustrating the ratio of TR-FRET signal generated by the interaction of Eu-VCB with streptavidin-APC-hydroxyprolyl HIF1α peptide over background signal generated by the interaction of Eu-VCB with streptavidin-APC-HIF1α peptide (nonhydroxylated).

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds.

Compounds of the invention may exist in multiple tautomeric forms. These forms are illustrated below as "Tautomer A", "Tautomer B", and "Tautomer C":

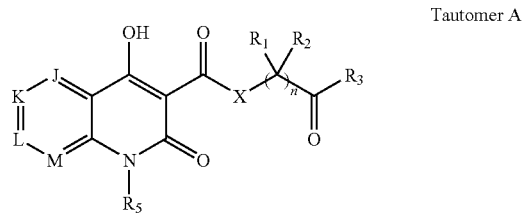

Tautomer A

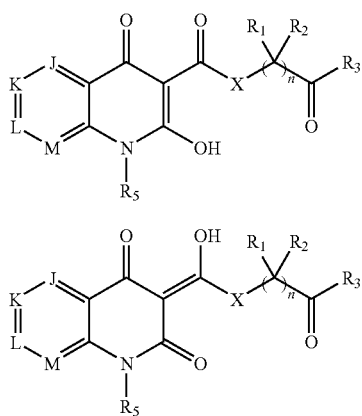

Compounds of the invention are depicted structurally and named as compounds in the "Tautomer A" form. However, it is specifically contemplated that the compounds may also exist in "Tautomer B" or "Tautomer C" form and compounds in "Tautomer B" form or "Tautomer C" form or another tautomeric form are expressly considered to be part of the invention.

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$)alkyl esters. In other embodiments, the term "compound: encompasses the compound itself, pharmaceutically acceptable salts thereof, tautomers of the compound, pharmaceutically acceptable salts of the tautomers As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I. In some embodiments, the prodrugs of the compounds of Formula I are esters such as methyl, ethyl, propyl, butyl, pentyl, and hexyl esters.

The term "solvate" refers to the compound formed by the interaction of a solvent and a compound. Suitable solvates are pharmaceutically acceptable solvates, such as hydrates, including monohydrates and hemihydrates.

"Alkyl" refers to a saturated, branched, straight-chain, or cyclic monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Alkenyl" refers to an unsaturated branched, straight-chain, or cyclic hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms, i.e. "lower alkynyl."

"Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include from 1 to 10 carbon atoms, from 1 to 6 carbon atoms or from 1 to 4 carbon atoms in the R group. Lower alkoxy groups include ($C_{1-6}$) alkyl groups and, in some embodiments, may include ($C_{1-4}$) alkyl groups.

"Alkylene" refers to a divalent saturated hydrocarbon group derived from a parent alkane by removal of two hydrogen atoms. Examples of alkylene group include, but are not limited to, —$CH_2$—, —$CH_2CH_2$—, —$CH(CH_3)$—, —$CH_2CH_2CH_2$—, —$CH_2C(CH_3)(H)$—, and the like.

"Alkenylene" refers to a divalent unsaturated hydrocarbon group having at least one carbon-carbon double bond derived by the removal of two hydrogen atoms from a parent alkene. The group may be in either the Z- or E-form (cis or trans) about the double bond(s). Examples of alkenylene groups, include, but are not limited to, —CH=CH—, —CH=C(H)$CH_2$—, $CH_2C(H)$=C(H)$CH_2$—, and the like.

"Alkynylene" refers to a divalent unsaturated hydrocarbon group having at least one carbon-carbon triple bond derived by the removal of two hydrogen atoms from a parent alkyne. Example of alkynylene groups, include, but are not limited to, —C≡C—, —$CH_2$C≡C—, —$CH_2$C≡$CCH_2$—.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocyclic ring containing 1 or more heteroatoms chosen from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocyclic aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically, but not necessarily, a terminal carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. In certain embodiments, an arylalkyl group can be ($C_{6-30}$) arylalkyl, e.g., the alkyl group of the arylalkyl group can be ($C_{1-10}$) and the aryl moiety can be ($C_{5-20}$).

"Arylalkenyl" refers to an alkenyl group in which a bond to one of the hydrogen atoms of the alkenyl group is replaced with a bond to an aryl group.

"Arylalkynyl" refers to an alkynyl group in which a bond to one of the hydrogen atoms of the alkynyl group is replaced with a bond to an aryl group.

"Carbonyl" refers to the radical —C(O) group.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocyclic", "heterocyclo" or "heterocyclyl" refer to a saturated or unsaturated, but non-aromatic, cyclic hydrocarbon group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, O, and S. Typical heterocyclyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Heterocyclylalkyl" refers to an alkyl group in which one of the hydrogen atoms of the alkyl is replaced with a bond to a heterocyclyl group. Examples of heterocyclylalkyl groups, include, but are not limited to, morpholinylmethyl, morpholinylethyl, tetrahydrofuranylmethyl, piperidinylmethyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic ring systems containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or a carbocyclic aromatic ring and a 5- to 7-membered heteroaromatic ring fused to a 5- to 7-membered heterocyclic ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkyl moiety of the heteroarylalkyl can include 1 to 10 members and the heteroaryl moiety of the heteroarylalkyl can include from 5 to 20-members.

"Sulfonyl" refers to a radical —S(O)₂R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —$R_{11}$, —OH, =O, —$OR_{11}$, —$SR_{11}$, —SH, =S, —$NR_{11}R_{12}$, =$NR_{11}$, —$CX_3$, —$CF_3$, —CN, —$NO_2$, —$S(O)_2R_{11}$, —$OS(O_2)OH$, —$OS(O)_2R_{11}$, —OP(O)($OR_{11}$)($OR_{12}$), —$C(O)R_{11}$, —$C(S)R_{11}$, —$C(O)OR_{11}$, —$C(O)NR_{11}R_{12}$, —C(O)OH, —$C(S)OR_{11}$, —$NR_{13}C(O)NR_{11}R_{12}$, —$NR_{13}C(S)NR_{11}R_{12}$, —$NR_{13}C(NR_{11})NR_{11}R_{12}$, —$C(NR_{11})NR_{11}R_{12}$, —$S(O)_2NR_{11}R_{12}$, —$NR_{13}S(O)_2R_{11}$, —$NR_{13}C(O)R_{11}$, and —$S(O)R_{11}$ where each X is independently a halo; each $R_{11}$ and $R_{12}$ are independently hydrogen, alkyl, substituted alkyl, alkyl interrupted by one or more —O— or —S— groups, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl, substituted heteroarylalkyl, —$NR_{13}R_{14}$, —$C(O)R_{13}$ or —$S(O)_2R_{13}$ or optionally $R_{11}$ and $R_{12}$ together with the atom to which $R_{11}$ and $R_{12}$ are attached form one or more heterocyclyl, substituted heterocyclyl, heteroaryl, or substituted heteroaryl rings; and $R_{13}$ and $R_{14}$ are independently hydrogen, alkyl, substituted alkyl, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl or substituted heteroarylalkyl, or optionally $R_{13}$ and $R_{14}$ together with the nitrogen atom to which $R_{13}$ and $R_{14}$ are attached form one or more heterocyclyl, substituted heterocyclyl, heteroaryl, or substituted heteroaryl rings. In certain embodiments, a tertiary amine or aromatic nitrogen may be substituted with on or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides composition of matter that includes at least one compound of Formula I:

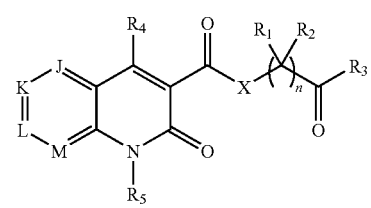

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

J, K, L, and M are selected from $CR_6$ or N, wherein two of J, K, L, and M are N and the other two of J, K, L, and M are $CR_6$;

n is 1 to 6;

$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;

X is selected from —$NR_a$—, —O—, or —S—, wherein $R_a$ is selected from H or lower alkyl;

$R_3$ is selected from OH, SH, $NH_2$, lower alkyl, substituted lower alkyl, lower alkoxy, substituted lower alkoxy, or sulfanyl;

$R_4$ is selected from H, OH, lower alkoxy, SH, $NH_2$, $NHSO_2R_7$, or sulfonyl;

$R_5$ is selected from H, lower alkyl, or substituted lower alkyl;

each $R_6$ is independently selected from H, F, Cl, Br, I, alkyl, substituted alkyl, haloalkyl, perhaloalkyl, alkenyl, substituted alkenyl, alkynyl, substituted alkynyl, $NR_dR_e$, $C(O)R_7$, $C(O)OR_8$, $OR_8$, $SR_8$, $SO_2R_8$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_9$, wherein:

Y is selected from —$N(R_{10})$—Z— or —Z—$N(R_{10})$—;

Z is selected from C(O), $SO_2$, alkylene, substituted alkylene, alkenylene, substituted alkenylene, alkynylene, or substituted alkynylene;

$R_7$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

$R_8$ is selected from H, alkyl, substituted alkyl, alkenyl, substituted alkenyl, alkynyl, or substituted alkynyl;

$R_9$ is selected from H, heterocyclyl, substituted heterocyclyl, aryl, substituted aryl, heteroaryl, or substituted heteroaryl;

$R_{10}$ is selected from H, lower alkyl, or substituted lower alkyl; and $R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

In some embodiments, $R_1$ and $R_2$ are not both H if X is —$NR_a$—; $R_a$ is H; and n is 1.

In some embodiments, n is 1, $R_1$ and $R_2$ are both H, X is —$NR_a$—; and $R_a$ is H.

In some embodiments, at least one of $R_1$ and $R_2$ is not H. In some such embodiments, at least one of $R_1$ and $R_2$ is a lower alkyl such as a $(C_1-C_4)$alkyl. In some such embodiments, one of $R_1$ and $R_2$ is H and the other of $R_1$ and $R_2$ is a lower alkyl. In some such embodiments, at least one of $R_1$ and $R_2$ is a methyl group, and in some such embodiments, the other of $R_1$ and $R_2$ is a methyl group.

In some embodiments, M and L are N and J and K are $CR_6$. In other embodiments, M and K are N and J and L are $CR_6$. In still other embodiments, J and M are N and K and L are $CR_6$.

In some embodiment, $R_3$ is OH.

In some embodiments, $R_4$ is selected from OH, SH, $NH_2$, $NHSO_2R_8$, or sulfonyl. In some such embodiments, $R_4$ is OH.

In some embodiments, X is —$NR_a$—. In some such embodiments, X is —NH—.

In some embodiments, at least one instance of $R_6$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_6$ is a heterocyclyl group. In other such embodiments, at least one instance of $R_6$ is a heteroaryl group. In other such embodiments, at least one instance of $R_6$ is a phenyl or substituted phenyl group.

In some embodiments, at least one instance of $R_6$ is independently selected from halo or a moiety substituted with at least one halo. For example, in some embodiments, at least one instance of $R_6$ is haloalkyl. In some embodiments, at least one instance of $R_6$ is a perhaloalkyl. In some such embodiments, the perhaloalkyl is a perfluoroalkyl group such as $CF_3$.

In some embodiments, one instance of $R_6$ is selected from —Cl, —$CF_3$, —SMe, —OMe, or a group having the formula

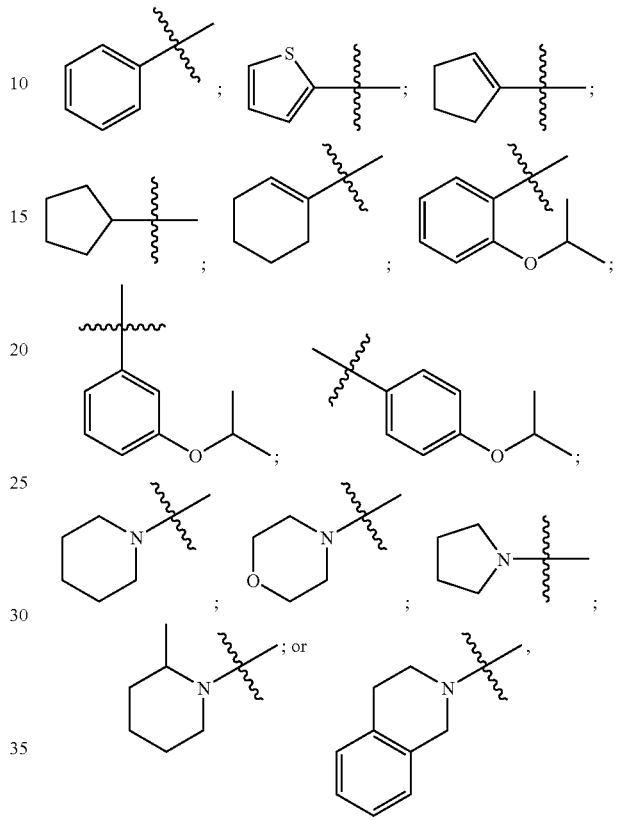

wherein the wavy line indicates the point of attachment to the rest of the molecule. In some such embodiments, one of $R_6$ is selected from a group having the formula

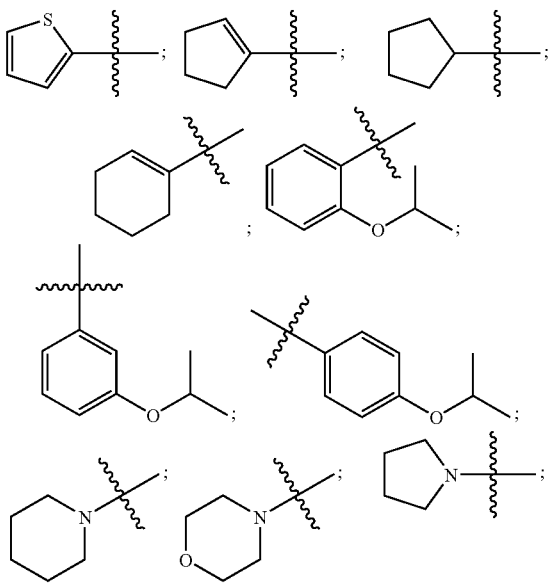

-continued

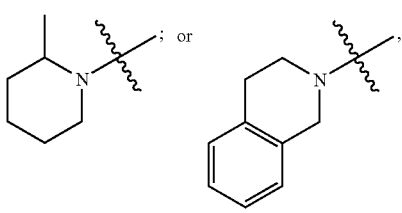; or

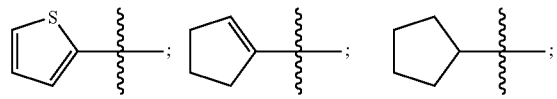

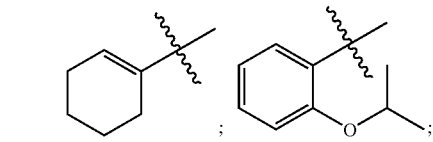

wherein the wavy line indicates the point of attachment to the rest of the molecule.

In some embodiments, one instance of $R_6$ is selected from —Cl, —CF$_3$, —SMe, —OMe, or a group having the formula

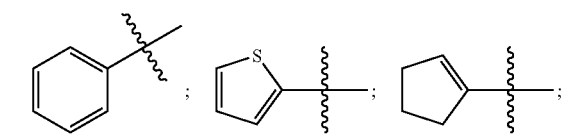

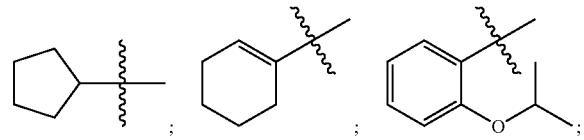

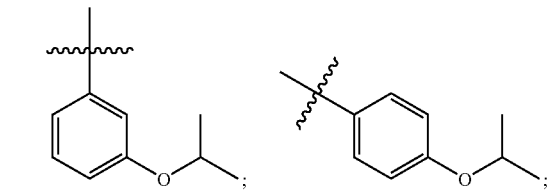

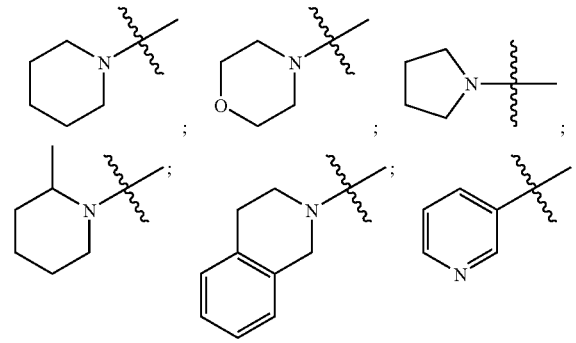

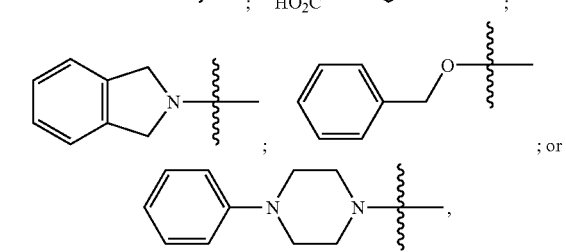

wherein the wavy line indicates the point of attachment to the rest of the molecule. In some such embodiments, one of $R_6$ is selected from a group having the formula

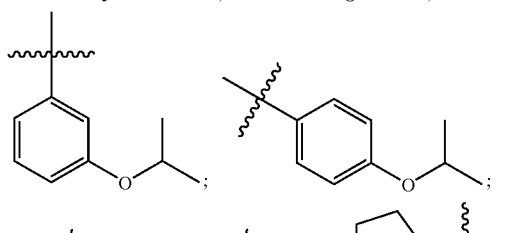

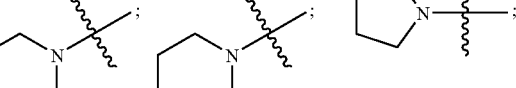

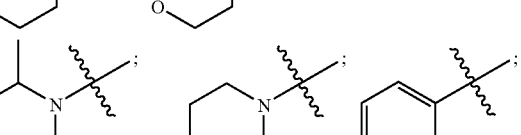

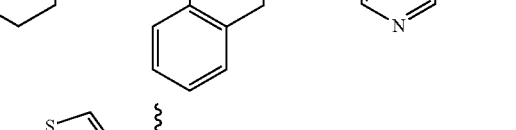

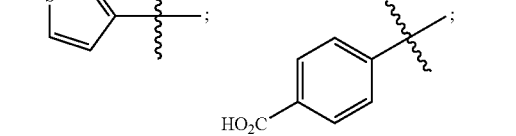

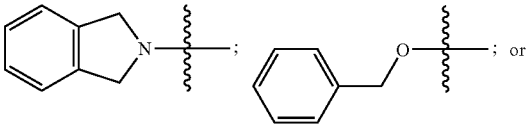

wherein the wavy line indicates the point of attachment to the rest of the molecule.

In some embodiments, $R_6$ is a group having the formula

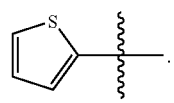

In some embodiments, $R_6$ is a group having the formula

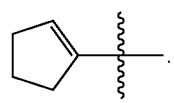

In some embodiments, $R_6$ is a group having the formula

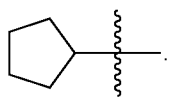

In some embodiments, $R_6$ is a group having the formula

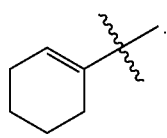

In some embodiments, $R_6$ is a group having the formula

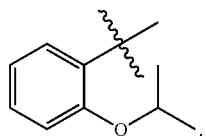

In some embodiments, $R_6$ is a group having the formula

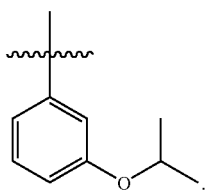

In some embodiments, $R_6$ is a group having the formula

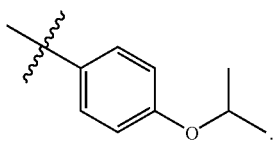

In some embodiments, $R_6$ is a group having the formula

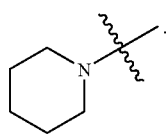

In some embodiments, $R_6$ is a group having the formula

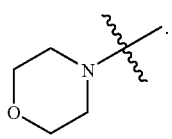

In some embodiments, $R_6$ is a group having the formula

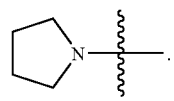

In some embodiments, $R_6$ is a group having the formula

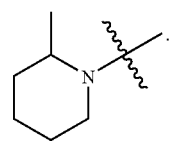

In some embodiments, $R_6$ is a group having the formula

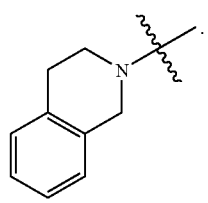

In some embodiments, n is 1.

In some embodiment, $R_1$ and $R_2$ are independently chosen from H and lower alkyl. In some such embodiments, $R_1$ and $R_2$ are both H. In some such embodiments, n is 1.

In some embodiments, n is 1; $R_1$ is H or lower alkyl; $R_2$ is H; $R_3$ is OH; $R_4$ is OH; X is —$NR_a$—; and $R_a$ is H.

In some embodiments of the compound of Formula I, $R_5$ is H. In other embodiments, $R_5$ is a lower alkyl group. In some such embodiments, $R_5$ is a methyl. In still other embodiments, $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

In some embodiments, the compound of Formula I has the Formula IA, and the variables have the definitions provided in any of the aspects and embodiments described above.

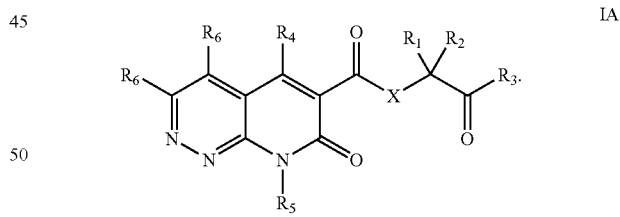

IA

In some embodiments, the compound of Formula I has the Formula IB, and the variables have the definitions provided in any of the aspects and embodiments described above.

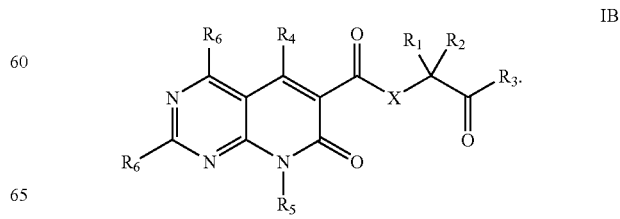

IB

In some embodiments, the compound of Formula I has the Formula IC, and the variables have the definitions provided in any of the aspects and embodiments described above.

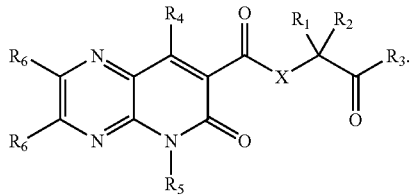

In some embodiments, the composition of matter is a salt. Such salts may be anhydrous or associated with one or more molecules of water as a hydrate.

In some embodiments, the composition of matter is a prodrug. In some such embodiments, the composition of matter is a ($C_1$-$C_6$)alkyl ester such as a methyl, ethyl, propyl, butyl, pentyl, or hexyl ester.

In one embodiment, the compound is any one of the Example compounds described herein. Therefore, in some embodiments, the compound is selected from any one or all of those listed below or is a salt thereof, a tautomer thereof, or a salt of the tautomer:

2-(3-chloro-5-hydroxy-8-methyl-7-oxo-7,8-dihydropyrido[2,3-c]pyridazine-6-carboxamido)acetic acid;
2-(5-hydroxy-8-methyl-7-oxo-3-phenyl-7,8-dihydropyrido[2,3-c]pyridazine-6-carboxamido)acetic acid;
2-(5-hydroxy-8-methyl-7-oxo-3-(thiophen-2-yl)-7,8-dihydropyrido[2,3-c]pyridazine-6-carboxamido)acetic acid;
2-(3-cyclopentenyl-5-hydroxy-8-methyl-7-oxo-7,8-dihydropyrido[2,3-c]pyridazine-6-carboxamido)acetic acid;
2-(3-cyclopentyl-5-hydroxy-8-methyl-7-oxo-7,8-dihydropyrido[2,3-c]pyridazine-6-carboxamido)acetic acid;
2-(3-cyclohexenyl-5-hydroxy-8-methyl-7-oxo-7,8-dihydropyrido[2,3-c]pyridazine-6-carboxamido)acetic acid;
2-(5-hydroxy-3-(3-isopropoxyphenyl)-8-methyl-7-oxo-7,8-dihydropyrido[2,3-c]pyridazine-6-carboxamido)acetic acid;
2-(5-hydroxy-3-(4-isopropoxyphenyl)-8-methyl-7-oxo-7,8-dihydropyrido[2,3-c]pyridazine-6-carboxamido)acetic acid;
2-(5-hydroxy-3-(2-isopropoxyphenyl)-8-methyl-7-oxo-7,8-dihydropyrido[2,3-c]pyridazine-6-carboxamido)acetic acid;
2-(5-hydroxy-8-methyl-2-(methylthio)-7-oxo-7,8-dihydropyrido[2,3-d]pyrimidine-6-carboxamido)acetic acid;
2-(5-hydroxy-8-methyl-7-oxo-2-(piperidin-1-yl)-7,8-dihydropyrido[2,3-d]pyrimidine-6-carboxamido)acetic acid;
2-(5-hydroxy-2-methoxy-8-methyl-7-oxo-7,8-dihydropyrido[2,3-d]pyrimidine-6-carboxamido)acetic acid;
2-(5-hydroxy-8-methyl-2-morpholino-7-oxo-7,8-dihydropyrido[2,3-d]pyrimidine-6-carboxamido)acetic acid;
2-(5-hydroxy-8-methyl-7-oxo-2-(trifluoromethyl)-7,8-dihydropyrido[2,3-d]pyrimidine-6-carboxamido)acetic acid;
2-(5-hydroxy-8-methyl-7-oxo-2-(pyrrolidin-1-yl)-7,8-dihydropyrido[2,3-d]pyrimidine-6-carboxamido)acetic acid;
2-(5-hydroxy-8-methyl-2-(2-methylpiperidin-1-yl)-7-oxo-7,8-dihydropyrido[2,3-d]pyrimidine-6-carboxamido)acetic acid; or
2-(2-(3,4-dihydroquinolin-1(2H)-yl)-5-hydroxy-8-methyl-7-oxo-7,8-dihydropyrido[2,3-d]pyrimidine-6-carboxamido)acetic acid; or 2-(8-hydroxy-5-methyl-6-oxo-3-phenyl-5,6-dihydropyrido[3,2-b]pyrazine-7-carboxamido)acetic acid.

In one embodiment, the compound is any one of the Example compounds described herein. Therefore, in some embodiments, the compound is selected from any one or all of those listed below or is a salt thereof, a tautomer thereof, or a salt of the tautomer:

2-(3-chloro-5-hydroxy-8-methyl-7-oxo-7,8-dihydropyrido[2,3-c]pyridazine-6-carboxamido)acetic acid;
2-(5-hydroxy-8-methyl-7-oxo-3-phenyl-7,8-dihydropyrido[2,3-c]pyridazine-6-carboxamido)acetic acid;
2-(5-hydroxy-8-methyl-7-oxo-3-(thiophen-2-yl)-7,8-dihydropyrido[2,3-c]pyridazine-6-carboxamido)acetic acid;
2-(3-cyclopentenyl-5-hydroxy-8-methyl-7-oxo-7,8-dihydropyrido[2,3-c]pyridazine-6-carboxamido)acetic acid;
2-(3-cyclopentyl-5-hydroxy-8-methyl-7-oxo-7,8-dihydropyrido[2,3-c]pyridazine-6-carboxamido)acetic acid;
2-(3-cyclohexenyl-5-hydroxy-8-methyl-7-oxo-7,8-dihydropyrido[2,3-c]pyridazine-6-carboxamido)acetic acid;
2-(5-hydroxy-3-(3-isopropoxyphenyl)-8-methyl-7-oxo-7,8-dihydropyrido[2,3-c]pyridazine-6-carboxamido)acetic acid;
2-(5-hydroxy-3-(4-isopropoxyphenyl)-8-methyl-7-oxo-7,8-dihydropyrido[2,3-c]pyridazine-6-carboxamido)acetic acid; or
2-(5-hydroxy-3-(2-isopropoxyphenyl)-8-methyl-7-oxo-7,8-dihydropyrido[2,3-c]pyridazine-6-carboxamido)acetic acid.

In other embodiments, the compound is selected from any one or all of those listed below or is a salt thereof, a tautomer thereof, or a salt of the tautomer:

2-(5-hydroxy-8-methyl-2-(methylthio)-7-oxo-7,8-dihydropyrido[2,3-d]pyrimidine-6-carboxamido)acetic acid;
2-(5-hydroxy-8-methyl-7-oxo-2-(piperidin-1-yl)-7,8-dihydropyrido[2,3-d]pyrimidine-6-carboxamido)acetic acid;
2-(5-hydroxy-2-methoxy-8-methyl-7-oxo-7,8-dihydropyrido[2,3-d]pyrimidine-6-carboxamido)acetic acid;
2-(5-hydroxy-8-methyl-2-morpholino-7-oxo-7,8-dihydropyrido[2,3-d]pyrimidine-6-carboxamido)acetic acid;
2-(5-hydroxy-8-methyl-7-oxo-2-(trifluoromethyl)-7,8-dihydropyrido[2,3-d]pyrimidine-6-carboxamido)acetic acid;
2-(5-hydroxy-8-methyl-7-oxo-2-(pyrrolidin-1-yl)-7,8-dihydropyrido[2,3-d]pyrimidine-6-carboxamido)acetic acid;
2-(5-hydroxy-8-methyl-2-(2-methylpiperidin-1-yl)-7-oxo-7,8-dihydropyrido[2,3-d]pyrimidine-6-carboxamido)acetic acid; or
2-(2-(3,4-dihydroquinolin-1(2H)-yl)-5-hydroxy-8-methyl-7-oxo-7,8-dihydropyrido[2,3-d]pyrimidine-6-carboxamido)acetic acid.

In yet another embodiment, the compound is selected from the following compound or is a salt thereof, a tautomer thereof, or a salt of the tautomer:

2-(8-hydroxy-5-methyl-6-oxo-3-phenyl-5,6-dihydropyrido[3,2-b]pyrazine-7-carboxamido)acetic acid.

In yet other embodiments, the compound is selected from any one or all of those listed below or is a salt thereof, a tautomer thereof, or a salt of the tautomer:

2-(5-hydroxy-8-methyl-7-oxo-7,8-dihydropyrido[2,3-c]pyridazine-6-carboxamido)acetic acid;
2-(5-hydroxy-8-methyl-7-oxo-3-(pyridin-3-yl)-7,8-dihydropyrido[2,3-c]pyridazine-6-carboxamido)acetic acid;
2-(5-hydroxy-8-methyl-7-oxo-3-(thiophen-3-yl)-7,8-dihydropyrido[2,3-c]pyridazine-6-carboxamido)acetic acid;
4-(6-(((carboxymethyl)carbamoyl)-5-hydroxy-8-methyl-7-oxo-7,8-dihydropyrido[2,3-c]pyridazin-3-yl)benzoic acid;

2-(8-benzyl-3-chloro-5-hydroxy-7-oxo-7,8-dihydropyrido [2,3-c]pyridazine-6-carboxamido)acetic acid;
2-(8-benzyl-5-hydroxy-7-oxo-7,8-dihydropyrido[2,3-c]pyridazine-6-carboxamido)acetic acid;
6-((carboxymethyl)carbamoyl)-5-hydroxy-8-methyl-7-oxo-7,8-dihydropyrido[2,3-c]pyridazine-3-carboxylic acid;
2-(2-cyano-5-hydroxy-8-methyl-7-oxo-7,8-dihydropyrido [2,3-d]pyrimidine-6-carboxamido)acetic acid;
6-((carboxymethyl)carbamoyl)-5-hydroxy-8-methyl-7-oxo-7,8-dihydropyrido[2,3-d]pyrimidine-2-carboxylic acid;
2-(5-hydroxy-2-(isoindolin-2-yl)-8-methyl-7-oxo-7,8-dihydropyrido[2,3-d]pyrimidine-6-carboxamido)acetic acid;
2-(2-(benzyloxy)-5-hydroxy-8-methyl-7-oxo-7,8-dihydropyrido[2,3-d]pyrimidine-6-carboxamido)acetic acid;
2-(8-benzyl-5-hydroxy-7-oxo-2-(trifluoromethyl)-7,8-dihydropyrido[2,3-d]pyrimidine-6-carboxamido)acetic acid;
2-(5-hydroxy-8-methyl-7-oxo-2-(4-phenylpiperazin-1-yl)-7,8-dihydropyrido[2,3-d]pyrimidine-6-carboxamido)acetic acid;
2-(5-hydroxy-3-methoxy-8-methyl-7-oxo-7,8-dihydropyrido[2,3-c]pyridazine-6-carboxamido)acetic acid; or
2-(5-hydroxy-8-methyl-7-oxo-3-(piperidin-1-yl)-7,8-dihydropyrido[2,3-c]pyridazine-6-carboxamido)acetic acid.

In other embodiments, the compound is selected from any one or all of those listed below or is a salt thereof, a tautomer thereof, or a salt of the tautomer:

2-(2-(2-ethylpiperidin-1-yl)-5-hydroxy-8-methyl-7-oxo-7,8-dihydropyrido[2,3-d]pyrimidine-6-carboxamido)acetic acid;
2-(2-(5-ethyl-2-methylpiperidin-1-yl)-5-hydroxy-8-methyl-7-oxo-7,8-dihydropyrido[2,3-d]pyrimidine-6-carboxamido)acetic acid;
2-(5-hydroxy-8-methyl-2-(octahydroquinolin-1(2H)-yl)-7-oxo-7,8-dihydropyrido[2,3-d]pyrimidine-6-carboxamido) acetic acid;
2-(2-(3-fluorophenyl)-5-hydroxy-8-methyl-7-oxo-7,8-dihydropyrido[2,3-d]pyrimidine-6-carboxamido)acetic acid;
2-(2-(2-cyclopropylethynyl)-5-hydroxy-8-methyl-7-oxo-7,8-dihydropyrido[2,3-d]pyrimidine-6-carboxamido)acetic acid;
2-(2-cyclopropyl-5-hydroxy-8-methyl-7-oxo-7,8-dihydropyrido[2,3-d]pyrimidine-6-carboxamido)acetic acid;
2-(5-hydroxy-8-methyl-7-oxo-2-phenyl-7,8-dihydropyrido [2,3-d]pyrimidine-6-carboxamido)acetic acid;
2-(2-(2-fluorophenyl)-5-hydroxy-8-methyl-7-oxo-7,8-dihydropyrido[2,3-d]pyrimidine-6-carboxamido)acetic acid;
2-(2-(4-fluorophenyl)-5-hydroxy-8-methyl-7-oxo-7,8-dihydropyrido[2,3-d]pyrimidine-6-carboxamido)acetic acid;
2-(5-hydroxy-8-methyl-2-(2-morpholinophenyl)-7-oxo-7,8-dihydropyrido[2,3-d]pyrimidine-6-carboxamido)acetic acid;
2-(5-hydroxy-8-methyl-2-(4-morpholinophenyl)-7-oxo-7,8-dihydropyrido[2,3-d]pyrimidine-6-carboxamido)acetic acid;
2-(2-(furan-3-yl)-5-hydroxy-8-methyl-7-oxo-7,8-dihydropyrido[2,3-d]pyrimidine-6-carboxamido)acetic acid;
2-(5-hydroxy-2-(2-methoxyphenyl)-8-methyl-7-oxo-7,8-dihydropyrido[2,3-d]pyrimidine-6-carboxamido)acetic acid;
2-(5-hydroxy-8-methyl-7-oxo-2-(4-(piperidin-1-yl)phenyl)-7,8-dihydropyrido[2,3-d]pyrimidine-6-carboxamido)acetic acid;
2-(5-hydroxy-2-(4-methoxyphenyl)-8-methyl-7-oxo-7,8-dihydropyrido[2,3-d]pyrimidine-6-carboxamido)acetic acid;
2-(5-hydroxy-2-(3-methoxyphenyl)-8-methyl-7-oxo-7,8-dihydropyrido[2,3-d]pyrimidine-6-carboxamido)acetic acid;
2-(5-hydroxy-8-methyl-7-oxo-2-(quinolin-5-yl)-7,8-dihydropyrido[2,3-d]pyrimidine-6-carboxamido)acetic acid;
2-(2-(benzo[b]thiophen-2-yl)-5-hydroxy-8-methyl-7-oxo-7,8-dihydropyrido[2,3-d]pyrimidine-6-carboxamido)acetic acid;
2-(5-hydroxy-8-methyl-7-oxo-2-m-tolyl-7,8-dihydropyrido [2,3-d]pyrimidine-6-carboxamido)acetic acid;
2-(2-(furan-2-yl)-5-hydroxy-8-methyl-7-oxo-7,8-dihydropyrido[2,3-d]pyrimidine-6-carboxamido)acetic acid;
2-(2-(4-chlorophenyl)-5-hydroxy-8-methyl-7-oxo-7,8-dihydropyrido[2,3-d]pyrimidine-6-carboxamido)acetic acid;
2-(2-(benzo[b]thiophen-3-yl)-5-hydroxy-8-methyl-7-oxo-7,8-dihydropyrido[2,3-d]pyrimidine-6-carboxamido)acetic acid;
2-(5-hydroxy-8-methyl-2-(naphthalen-2-yl)-7-oxo-7,8-dihydropyrido[2,3-d]pyrimidine-6-carboxamido)acetic acid;
2-(5-hydroxy-2-(1H-indol-2-yl)-8-methyl-7-oxo-7,8-dihydropyrido[2,3-d]pyrimidine-6-carboxamido)acetic acid;
2-(2-(3-chlorophenyl)-5-hydroxy-8-methyl-7-oxo-7,8-dihydropyrido[2,3-d]pyrimidine-6-carboxamido)acetic acid;
2-(5-hydroxy-8-methyl-2-(1-methyl-1H-indol-5-yl)-7-oxo-7,8-dihydropyrido[2,3-d]pyrimidine-6-carboxamido)acetic acid;
2-(5-hydroxy-8-methyl-7-oxo-2-(quinolin-4-yl)-7,8-dihydropyrido[2,3-d]pyrimidine-6-carboxamido)acetic acid;
2-(5-hydroxy-8-methyl-2-(naphthalen-1-yl)-7-oxo-7,8-dihydropyrido[2,3-d]pyrimidine-6-carboxamido)acetic acid;
2-(5-hydroxy-8-methyl-7-oxo-2-p-tolyl-7,8-dihydropyrido [2,3-d]pyrimidine-6-carboxamido)acetic acid;
2-(2-(benzofuran-5-yl)-5-hydroxy-8-methyl-7-oxo-7,8-dihydropyrido[2,3-d]pyrimidine-6-carboxamido)acetic acid;
2-(5-hydroxy-8-methyl-7-oxo-2-(quinolin-3-yl)-7,8-dihydropyrido[2,3-d]pyrimidine-6-carboxamido)acetic acid;
2-(5-hydroxy-8-methyl-7-oxo-2-o-tolyl-7,8-dihydropyrido [2,3-d]pyrimidine-6-carboxamido)acetic acid;
2-(2-(benzo[b]thiophen-5-yl)-5-hydroxy-8-methyl-7-oxo-7,8-dihydropyrido[2,3-d]pyrimidine-6-carboxamido)acetic acid;
2-(2-(4-cyanophenyl)-5-hydroxy-8-methyl-7-oxo-7,8-dihydropyrido[2,3-d]pyrimidine-6-carboxamido)acetic acid;
2-(5-hydroxy-8-methyl-2-(3-morpholinophenyl)-7-oxo-7,8-dihydropyrido[2,3-d]pyrimidine-6-carboxamido)acetic acid;
2-(5-hydroxy-8-methyl-7-oxo-2-(thiophen-3-yl)-7,8-dihydropyrido[2,3-d]pyrimidine-6-carboxamido)acetic acid;
2-(5-hydroxy-8-methyl-7-oxo-2-(pyridin-3-yl)-7,8-dihydropyrido[2,3-d]pyrimidine-6-carboxamido)acetic acid;
2-(5-hydroxy-2-(1H-indol-4-yl)-8-methyl-7-oxo-7,8-dihydropyrido[2,3-d]pyrimidine-6-carboxamido)acetic acid;
2-(5-hydroxy-8-methyl-2-(1-methyl-1H-indol-2-yl)-7-oxo-7,8-dihydropyrido[2,3-d]pyrimidine-6-carboxamido)acetic acid; or
2-(5-hydroxy-8-methyl-7-oxo-2-(1-tosyl-1H-indol-3-yl)-7,8-dihydropyrido[2,3-d]pyrimidine-6-carboxamido)acetic acid.

Compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

Also provided herein are pharmaceutical formulations that include at least one pharmaceutically acceptable carrier, excipient, or diluent, and a therapeutically effective amount of the composition of matter any of the embodiments described herein. In such embodiments, the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical formulations that include at least one pharmaceutically acceptable carrier, and a therapeutically effective amount of the composition of matter of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject the composition of matter of any of the embodiments described herein.

Further provided is a method of treating a condition where it is desired to modulate HIF activity comprising administering to a subject the composition of matter of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject the composition of matter of any of the embodiments described herein.

Also provided is a method of treating anemia in a subject comprising administering to a subject the composition of matter of any of the embodiments described herein.

The compounds of the invention may also be used to prepare medicaments or in methods for stimulating erythropoiesis in a subject. Such methods and medicaments utilize a compound of any of the embodiments of the invention. In such methods, a compound of any of the embodiments is typically administered to a subject such as a human subject in a therapeutically effective amount.

Further provided is a method of modulating the amount of HIF in a cell comprising contacting the cell with the composition of matter of any of the embodiments described herein.

Additionally provided is a method of increasing the amount of hemoglobin F in a subject comprising administering to the subject the composition of matter of any of the embodiments described herein.

Also provided is a method of modulating angiogenesis in a subject comprising administering to the subject the composition of matter of any of the embodiments described herein.

Additionally provided is a method of treating at least one disease in a patient in need of such treatment comprising administering to the patient a therapeutically effective amount of the composition of matter of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject the composition of matter of any of the embodiments described herein.

In some embodiments, the HIF PHD inhibitory activity $IC_{50}$ value of the composition of matter is 40 µM or less. In other embodiments, the HIF PHD inhibitory activity $IC_{50}$ value of the composition of matter is 10 µM or less. In still other embodiments, the HIF PHD inhibitory activity $IC_{50}$ value of the composition of matter is 100 nM or less, whereas in others it is 10 nM or less.

In some embodiments, the composition of matter of any of the embodiments is used in the preparation of a pharmaceutical formulation or medicament.

In some such embodiments, the composition of matter of any of the embodiments is used in the preparation of a medicament for increasing or stabilizing HIF levels or activity in a subject.

In some such embodiments, the composition of matter of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the composition of matter of any of the embodiments is used in the preparation of a medicament for treating a hypoxic or ischemic related disorder in a subject.

In some embodiments, the composition of matter of any of the embodiments is used in the preparation of a medicament for modulating the amount if HIF in a cell. In some embodiments, the composition of matter according to any of the embodiments is used to modulate the amount of HIF in a cell.

In some embodiments, the composition of matter of any of the embodiments is used in the preparation of a medicament for modulating angiogenesis in a subject.

In some embodiments, the composition of matter of any of the embodiments is used in the preparation of a medicament for inhibiting HIF hydroxylation in a subject.

In some embodiments, the composition of matter of any of the embodiments is used in the preparation of a medicament for treating anemia.

In some embodiments, the composition of matter of any of the embodiments is used in a method for increasing the level of erythropoietin in the blood of a subject.

The phrase "composition of matter" as used herein is intended to encompass the compounds of the invention, pharmaceutically acceptable salts thereof, tautomers thereof, and pharmaceutically acceptable salts of the tautomer. It may also includes solvates, chelates, non-covalent complexes, pro-drugs and mixtures of these in addition to a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be prepared using the general synthetic route shown below in Scheme 1 and described more fully in the Examples.

Scheme 1

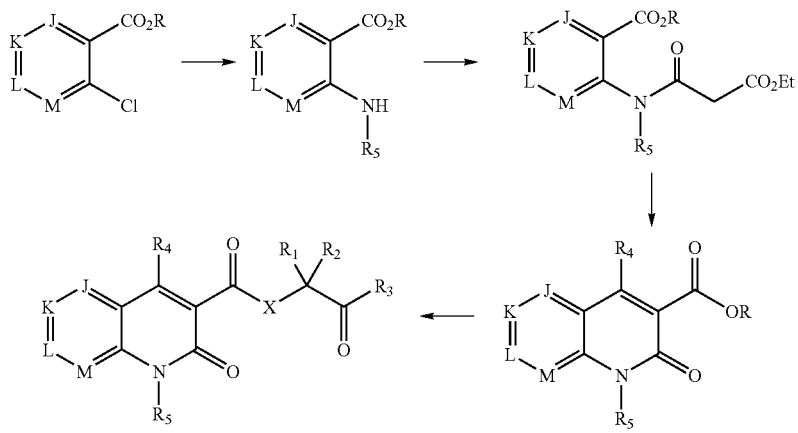

The invention is further described by reference to the following examples, which are intended to exemplify the claimed invention but not to limit it in any way.

EXAMPLES

Unless otherwise stated, all compounds were obtained from commercial sources or were prepared using the methods and experimental procedures described herein. The following abbreviations are used to refer to various reagents and solvents:

| | |
|---|---|
| AcOH | Acetic Acid |
| ACN | Acetonitrile |
| DCM | Dichloromethane |
| DIPEA | Diisopropylethylamine |
| DMA | Dimethylacetamide |
| DMAP | Dimethylaminopyridine |
| DMF | N,N-Dimethylformamide |
| DMSO | Dimethylsulfoxide |
| EtOAc | Ethyl Acetate |
| EtOH | Ethanol |
| MCPBA | meta-Chloroperoxybenzoic acid |
| MeOH | Methanol |
| TFA | Trifluoroacetic acid |
| THF | Tetrahydrofuran |
| TR-FRET | Time Resolved-Fluorescence Resonance Energy Transfer |

Method 1. Preparation of Sodium 3-Chloro-6-(ethoxycarbonyl)-8-methyl-7-oxo-7,8-dihydropyrido[2,3-c]pyridazin-5-olate

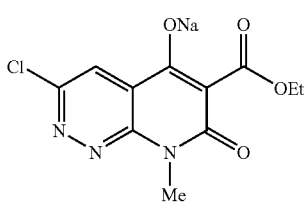

(a) Ethyl 3,6-dichloropyridazine-4-carboxylate. To a solution of 3,6-dichloropyridazine-4-carboxylic acid (5.0 g, 26 mmol, commercially available from Aldrich, Milwaukee, Wis.) in THF (5.0 mL) and EtOH (5.0 mL, 26 mmol) was added DMAP (0.32 g, 2.6 mmol) and n-(3-dimethylaminopropyl)-n'-ethylcarbodiimide hydrochloride (5.0 g, 28 mmol). The reaction was stirred at room temperature for 12 hours. Solvent was removed under reduced pressure to afford an oil. The oil was partitioned between EtOAc and water, and the organic extracts were combined, dried over sodium sulfate, filtered, and concentrated to afford a yellow oil. The crude product was purified by silica gel flash chromatography (10% EtOAc/Hexane) to provide a colorless oil. MS (ESI) m/z: Calculated: 221.0. Observed: 221.0. $^1$H NMR (400 MHz, CDCl$_3$) δ ppm 7.85 (s, 1H), 4.48 (q, J=7.24 Hz, 2H), 1.44 (t, J=7.24 Hz, 3H).

(b) Ethyl 6-chloro-3-(methylamino)pyridazine-4-carboxylate. To a sealed tube was added ethyl 3,6-dichloropyridazine-4-carboxylate (2.0 g, 9 mmol), anhydrous K$_2$CO$_3$ (1.0 g, 10 mmol), and 2.0 M MeNH$_2$ in THF (6 mL, 12 mmol). The tube was sealed, the resulting yellow mixture was stirred at room temperature for 16 hours, and then the solids were collected by filtration and washed with EtOAc to afford a white solid. MS (ESI) m/z: Calculated: 215.6. Observed: 216.1.

(c) Ethyl 6-chloro-3-(3-ethoxy-N-methyl-3-oxopropanamido)pyridazine-4-carboxylate. To a mixture of ethyl 6-chloro-3-(methylamino)pyridazine-4-carboxylate (1.6 g, 7.4 mmol) and anhydrous K$_2$CO$_3$ (1.3 g, 9.6 mmol) in THF (50.0 mL) was added dropwise propanoic acid, 3-chloro-3-oxo-, ethyl ester (1.1 mL, 8.9 mmol, commercially available from Aldrich, Milwaukee, Wis.). After stirring the reaction at room temperature for 16 hours, the solids were removed by filtration, and the filtrate was concentrated to afford a dark oil. The crude product was purified by silica gel flash chromatography (40% EtOAc/Hexane) to provide a yellow oil. MS (ESI) m/z: Calculated: 329.7. Observed: 330.0.

(d) Sodium 3-chloro-6-(ethoxycarbonyl)-8-methyl-7-oxo-7,8-dihydropyrido[2,3-c]pyridazin-5-olate. To an ice-cooled solution of EtOH (5.0 mL) were added small pieces of sodium metal (0.17 g, 7.3 mmol). The ice bath was removed and the mixture was stirred at room temperature until the sodium was no longer visible. The NaOEt solution was transferred dropwise to a solution of ethyl 6-chloro-3-(3-ethoxy-N-methyl-3-oxopropanamido)pyridazine-4-carboxylate (1.2 g, 3.6 mmol) in EtOH (3 mL). After the addition was complete, the mixture was stirred for an additional 2 minutes, and then the solids were collected by filtration and washed with ether. MS (ESI) m/z: Calculated: 283.7. Observed: 284.0. $^1$H NMR (300 MHz, DMSO-d$_6$) δ ppm 7.84 (s, 1H), 4.06 (q, J=7.16 Hz, 2H), 3.54 (s, 3H), 1.19 (t, J=7.16 Hz, 3H).

Method 2. Preparation of 2-(5-Hydroxy-8-methyl-7-oxo-3-phenyl-7,8-dihydropyrido[2,3-c]pyridazine-6-carboxamido)acetic acid

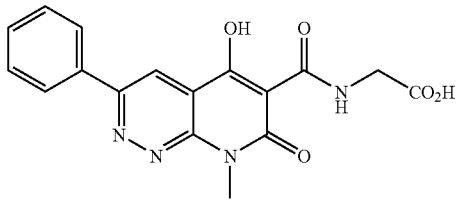

(a) Ethyl 5-hydroxy-8-methyl-7-oxo-3-phenyl-7,8-dihydropyrido[2,3-c]pyridazine-6-carboxylate. In a sealed tube was combined sodium 3-chloro-6-(ethoxycarbonyl)-8-methyl-7-oxo-7,8-dihydropyrido[2,3-c]pyridazin-5-olate (0.50 g, 1.8 mmol), phenyl boronic acid (3.5 mmol, commercially available from Aldrich, Milwaukee, Wis.), Pd(PPh$_3$)$_4$ (0.20 g, 0.18 mmol), 2.0 M aq. Na$_2$CO$_3$ (2.6 mL, 5.3 mmol), and 1,2-dimethoxyethane (10.0 mL, 1.8 mmol). The tube was flushed with argon, sealed, and then heated in an oil bath at 100° C. for 16 hours. The crude reaction mixture was adsorbed onto silica and purified via flash chromatography (5% to 20% MeOH/CHCl$_3$).

(b) tert-Butyl 2-(5-hydroxy-8-methyl-7-oxo-3-phenyl-7,8-dihydropyrido[2,3-c]pyridazine-6-carboxamido)acetate. In a sealed tube was combined ethyl 5-hydroxy-8-methyl-7-oxo-3-substituted-7,8-dihydropyrido[2,3-c]pyridazine-6-carboxylate (0.57 g, 1.8 mmol), tert-butyl 2-aminoacetate hydrochloride (0.29 g, 1.8 mmol), and N-ethyl-N-isopropylpropan-2-amine (0.31 mL, 1.8 mmol) in dioxane (5.0 mL). The tube was sealed and heated in an oil bath at 100° C. for 12 hours. The crude reaction mixture was purified by flash chromatography (100% CHCl$_3$).

(c) 2-(5-Hydroxy-8-methyl-7-oxo-3-phenyl-7,8-dihydropyrido[2,3-c]pyridazine-6-carboxamido)acetic acid. A solution of TFA (2 mL) and tert-butyl 2-(5-hydroxy-8-methyl-7-oxo-3-substituted-7,8-dihydropyrido[2,3-c]pyridazine-6-carboxamido)acetate was stirred at room temperature for 15 minutes and then concentrated under reduced pressure. Ether (5 mL) was added, and the resulting solid was collected by filtration, washed with water (3×5 mL) and then washed with ether (2×5 mL), and dried under vacuum at 50° C. $^1$H NMR (400 MHz, DMSO-d$_6$) δ ppm 10.31-10.46 (1H, m), 8.58 (1H, s), 8.19-8.29 (2H, m), 7.46-7.65 (3H, m), 4.18 (2H, d, J=5.5 Hz), 3.87 (3H, s).

Method 3. Preparation of 2-(3-Chloro-5-hydroxy-8-methyl-7-oxo-7,8-dihydropyrido[2,3-c]pyridazine-6-carboxamido)acetic acid

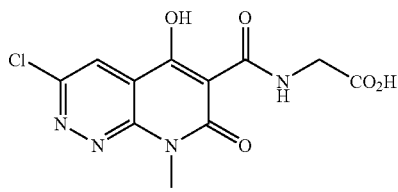

(a) tert-Butyl 2-(3-chloro-5-hydroxy-8-methyl-7-oxo-7,8-dihydropyrido[2,3-c]pyridazine-6-carboxamido)acetate. To a solution of sodium 3-chloro-6-(ethoxycarbonyl)-8-methyl-7-oxo-7,8-dihydropyrido[2,3-c]pyridazin-5-olate (7.0 g, 23 mmol), tert-butyl 2-aminoacetate hydrochloride (3.8 g, 23 mmol) in dioxane (80 mL) was added N-ethyl-N-isopropylpropan-2-amine (4.0 mL, 23 mmol). The flask was sealed and heated in an oil bath at 90° C. for 12 hours. The reaction was filtered while still very warm, and the collected solids were washed with ether. The filtrate was concentrated to afford crude tert-butyl 2-(3-chloro-5-hydroxy-8-methyl-7-oxo-7,8-dihydropyrido[2,3-c]pyridazine-6-carboxamido)acetate.

(b) 2-(3-Chloro-5-hydroxy-8-methyl-7-oxo-7,8-dihydropyrido[2,3-c]pyridazine-6-carboxamido)acetic acid. tert-Butyl 2-(3-chloro-5-hydroxy-8-methyl-7-oxo-7,8-dihydropyrido[2,3-c]pyridazine-6-carboxamido)acetate (0.140 g, 0.358 mmol) was dissolved in TFA (2 mL) and stirred for 10 minutes. The reaction was concentrated under reduced pressure, and the resulting yellow solid was washed with water (3×20 mL) and then washed with ether (2×10 mL) and acetone (2×10 mL). MS (ESI) m/z: Calculated: 312.7. Observed (M$^+$−1): 311.1. $^1$H NMR (400 MHz, DMSO-d$_6$) δ ppm 10.24-10.46 (m, 1H), 8.37 (s, 1H), 4.16 (d, J=5.67 Hz, 2H), 3.77 (s, 3H).

Method 4. Preparation of 2-(3-Cyclopentyl-5-hydroxy-8-methyl-7-oxo-7,8-dihydropyrido[2,3-c]pyridazine-6-carboxamido)acetic acid

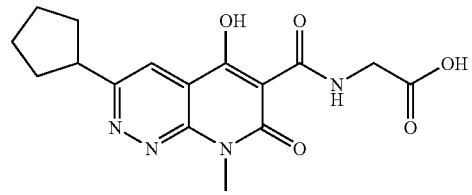

(a) tert-Butyl 2-(3-cyclopentenyl-5-hydroxy-8-methyl-7-oxo-7,8-dihydropyrido[2,3-c]pyridazine-6-carboxamido)acetate. This compound was prepared according to Method 2 using cyclopentenyl boronic acid.

(b) tert-Butyl 2-(3-cyclopentyl-5-hydroxy-8-methyl-7-oxo-7,8-dihydropyrido[2,3-c]pyridazine-6-carboxamido)acetate. To a solution of tert-butyl 2-(3-cyclopentenyl-5-hydroxy-8-methyl-7-oxo-7,8-dihydropyrido[2,3-c]pyridazine-6-carboxamido)acetate (0.33 g, 0.82 mmol) (in MeOH (20 mL) was added 10 mol % palladium/carbon. The reaction was flushed with hydrogen three times and then kept under balloon pressure while stirring for 72 hours. After filtering the reaction through celite and washing with DCM, the filtrate was concentrated. The crude mixture was adsorbed onto silica and purified via flash chromatography (2% MeOH/CHCl$_3$).

(c) 2-(3-Cyclopentyl-5-hydroxy-8-methyl-7-oxo-7,8-dihydropyrido[2,3-c]pyridazine-6-carboxamido)acetic acid. tert-Butyl 2-(3-cyclopentyl-5-hydroxy-8-methyl-7-oxo-7,8-dihydropyrido[2,3-c]pyridazine-6-carboxamido)acetate (0.170 g, 0.42 mmol), was combined with silica (2.0 g) and toluene (30 mL) in a sealed tube and heated at 125° C. for 3 hours. The reaction was cooled, 2.0 g of fresh silica was added, and the reaction was heated at 125° C. for 12 hours. After cooling to room temperature, the reaction was filtered and the silica was washed with acetone. The filtrate was concentrated, and the crude reaction mixture was purified by flash chromatography to afford a brown solid. MS (ESI) m/z: Calculated: 346.3. Observed: 347.1. $^1$H NMR (400 MHz, DMSO-d$_6$) δ ppm 10.31-10.48 (1H, m), 8.03 (1H, s), 4.15 (2H, d, J=4.9 Hz), 3.80 (3H, s), 3.48-3.59 (1H, m), 2.06-2.19 (2H, m), 1.65-1.92 (6H, m).

TABLE 1

The following table lists compounds which were prepared by the methods described above.

| Ex. | Structure | Name | $^1$H NMR (δ ppm) | Method |
|---|---|---|---|---|
| 1 | 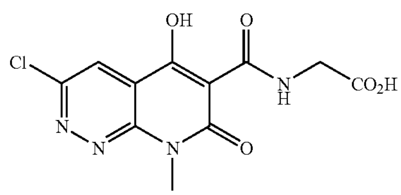 | 2-(3-chloro-5-hydroxy-8-methyl-7-oxo-7,8-dihydropyrido[2,3-c]pyridazine-6-carboxamido)acetic acid | 10.24-10.46 (m, 1 H), 8.37 (s, 1 H), 4.16 (d, j = 5.67 Hz, 2 H), 3.77 (s, 3 H) | 1, 3 |
| 2 | 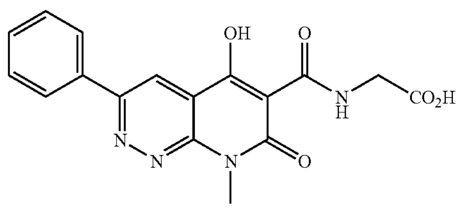 | 2-(5-hydroxy-8-methyl-7-oxo-3-phenyl-7,8-dihydropyrido[2,3-c]pyridazine-6-carboxamido)acetic acid | 10.31-10.46 (1 H, m), 8.58 (1 H, s), 8.19-8.29 (2 H, m), 7.46-7.65 (3 H, m), 4.18 (2 H, d, J = 5.5 Hz), 3.87 (3 H, s) | 1, 2 |
| 3 | 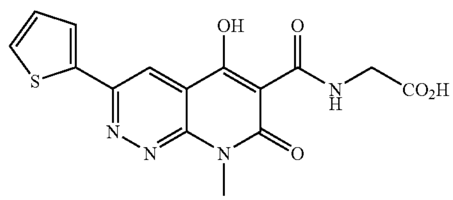 | 2-(5-hydroxy-8-methyl-7-oxo-3-(thiophen-2-yl)-7,8-dihydropyrido[2,3-c]pyridazine-6-carboxamido)acetic acid | 8.61 (1 H, s), 8.03-8.12 (1 H, m), 7.72-7.78 (1 H, m), 7.20-7.28 (1 H, m), 4.17 (2 H, d, J = 5.5 Hz), 3.82 (3 H, s) | 1, 2 |
| 4 | 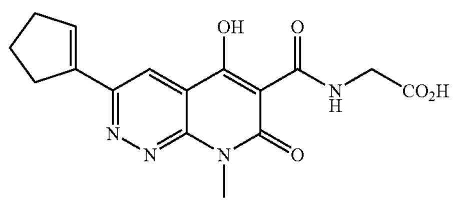 | 2-(3-cyclopentenyl-5-hydroxy-8-methyl-7-oxo-7,8-dihydropyrido[2,3-c]pyridazine-6-carboxamido)acetic acid | 10.29-10.44 (1 H, m), 8.28 (1 H, s), 6.82-6.97 (1 H, m), 4.17 (2 H, d, J = 5.1 Hz), 3.81 (3 H, s), 2.87-2.96 (2 H, m), 2.56-2.68 (2 H, m), 1.96-2.11 (2 H, m) | 1, 2 |
| 5 | 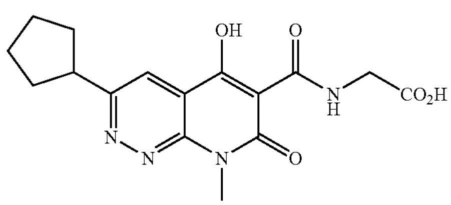 | 2-(3-cyclopentyl-5-hydroxy-8-methyl-7-oxo-7,8-dihydropyrido[2,3-c]pyridazine-6-carboxamido)acetic acid | 10.31-10.48 (1 H, m), 8.03 (1 H, s), 4.15 (2 H, d, J = 4.9 Hz), 3.80 (3 H, s), 3.48-3.59 (1 H, m), 2.06-2.19 (2 H, m), 1.65-1.92 (6 H, m). | 1, 4 |
| 6 | 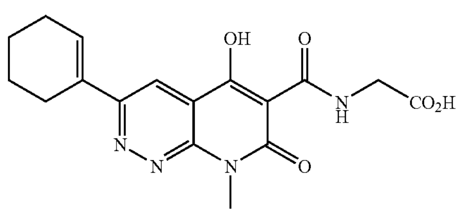 | 2-(3-cyclohexenyl-5-hydroxy-8-methyl-7-oxo-7,8-dihydropyrido[2,3-c]pyridazine-6-carboxamido)acetic acid | 10.31-10.45 (1 H, m), 8.19 (1 H, s), 6.79-6.96 (1 H, m), 4.09-4.23 (2 H, m), 3.83 (3 H, s), 2.59-2.71 (2 H, m), 2.24-2.35 (2 H, m), 1.62-1.87 (4 H, m) | 1, 2 |
| 7 | 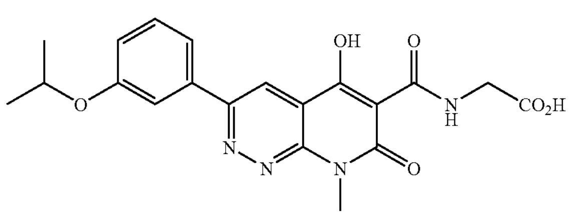 | 2-(5-hydroxy-3-(3-isopropoxyphenyl)-8-methyl-7-oxo-7,8-dihydropyrido[2,3-c]pyridazine-6-carboxamido)acetic acid | 10.35-10.48 (1 H, m), 8.58 (1 H, s), 7.70-7.81 (2 H, m), 7.40-7.52 (1 H, m), 7.02-7.12 (1 H, m), 4.71-4.85 (1 H, m), 4.11-4.23 (2 H, m), 3.86 (3 H, s), 1.22-1.40 (6 H, m) | 1, 2 |

TABLE 1-continued

The following table lists compounds which were prepared by the methods described above.

| Ex. | Structure | Name | ¹H NMR (δ ppm) | Method |
|---|---|---|---|---|
| 8 | 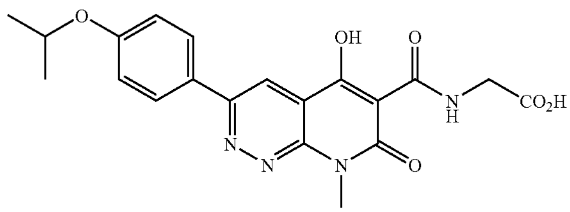 | 2-(5-hydroxy-3-(4-isopropoxyphenyl)-8-methyl-7-oxo-7,8-dihydropyrido[2,3-c]pyridazine-6-carboxamido)acetic acid | 10.36-10.46 (1 H, br s), 8.48 (1 H, s), 8.12-8.21 (2 H, m), 7.06-7.14 (2 H, m), 4.68-4.80 (1 H, m), 4.14-4.19 (2 H, m), 3.84 (3 H, s), 1.31 (6 H, d, J = 5.9 Hz) | 1, 2 |
| 9 | 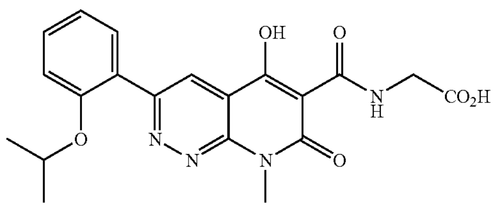 | 2-(5-hydroxy-3-(2-isopropoxyphenyl)-8-methyl-7-oxo-7,8-dihydropyrido[2,3-c]pyridazine-6-carboxamido)acetic acid | 10.34-10.43 (1 H, m), 8.68 (1 H, s), 7.92-8.00 (1 H, m), 7.44-7.53 (1 H, m), 7.23-7.29 (1 H, m), 7.08-7.19 (1 H, m), 4.70-4.84 (1 H, m), 4.16 (2 H, d, J = 5.5 Hz), 3.85 (3 H, s), 1.29 (6 H, d, J = 6.1 Hz) | 1, 2 |

Method 5. Preparation of 2-(5-Hydroxy-8-methyl-7-oxo-2-(trifluoromethyl)-7,8-dihydropyrido[2,3-d]pyrimidine-6-carboxamido)acetic acid

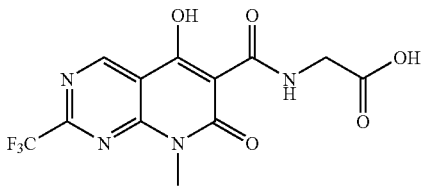

(a) Ethyl 4-(methylamino)-2-(trifluoromethyl)pyrimidine-5-carboxylate. A mixture of ethyl 4-chloro-2-(trifluoromethyl)pyrimidine-5-carboxylate (1 g, 4 mmol, commercially available from Maybridge), $K_2CO_3$ (2 g, 12 mmol) and methylamine (2.0M solution in THF (20 mL)) was stirred at room temperature overnight. The reaction mixture was filtered through Celite and concentrated under reduced pressure to give the crude product as a light-peach colored solid. MS m/z: Calculated: 249.19. Observed; 250.

(b) Ethyl 4-(3-ethoxy-N-methyl-3-oxopropanamido)-2-(trifluoromethyl)pyrimidine-5-carboxylate. To a solution of ethyl 4-(methylamino)-2-(trifluoromethyl)pyrimidine-5-carboxylate (200 mg, 0.80 mmol) in DCM (10 mL) were added ethyl malonoyl chloride (0.21 mL, 1.6 mmol) and a suspension of silver cyanide (0.027 mL, 0.8 mmol) in ACN (10 mL). Reaction was stirred at room temperature for 10 days. Another equivalent of AgCN and 1 mL of ethyl malonyl chloride was added, and the reaction was heated at reflux and stirred for 3 days. The solid was filtered off and the filtrate was concentrated to give an orange oil. The yield was approximately 48% as determined LCMS. The product was used in the next step without further purification.

(c) 5-Hydroxy-8-methyl-7-oxo-2-(trifluoromethyl)-7,8-dihydropyrido[2,3-d]pyrimidine-6-carboxylate. Ethyl 4-(3-ethoxy-N-methyl-3-oxopropanamido)-2-(trifluoromethyl)pyrimidine-5-carboxylate (140 mg, 0.39 mmol) was diluted in EtOH (10 mL) and then treated with 20 wt % NaOEt (5 mL, 0.39 mmol) at room temperature for 15 minutes. A yellow precipitate was filtered and some solid was recovered but filtrate was cloudy. AcOH was added to the filtrate which was then concentrated under reduced pressure to give an oily solid. Ether was added, and the mixture washed with water and brine and then dried over $MgSO_4$ and concentrated under reduced pressure to give a yellow oil. The product was used in the next step without further purification.

(d) tert-Butyl 2-(5-hydroxy-8-methyl-7-oxo-2-(trifluoromethyl)-7,8-dihydropyrido[2,3-d]pyrimidine-6-carboxamido)acetate. A mixture of ethyl 5-hydroxy-8-methyl-7-oxo-2-(trifluoromethyl)-7,8-dihydropyrido[2,3-d]pyrimidine-6-carboxylate (140 mg, 0.44 mmol), glycine, 1,1-dimethylethyl ester, DIPEA (0.23 mL, 1.3 mmol) and 1,4-dioxane (10 m) was stirred at 100° C. for 4 hours. The mixture was then concentrated under reduced pressure to give a yellow oil. The oil was purified by silica flash chromatography (0-30% EtOAc:Hex) to give a crystalline solid. The solid was washed with ether and decanted to give an initial solid, 34 mg. The filtrate was concentrated under reduced pressure to a yellow solid which was washed with hexane and filtered to give additional solid. Combined yield=81 mg (46%). MS m/z: Calculated: 402.33; Observed: 403.

(e) 2-(5-Hydroxy-8-methyl-7-oxo-2-(trifluoromethyl)-7,8-dihydropyrido[2,3-d]pyrimidine-6-carboxamido)acetic acid. A solution of tert-butyl 2-(5-hydroxy-8-methyl-7-oxo-2-(trifluoromethyl)-7,8-dihydropyrido[2,3-d]pyrimidine-6-carboxamido)acetate (81 mg, 0.2 mmol) and TFA (3 mL) was stirred at room temperature for 15 minutes. The mixture was concentrated under reduced pressure to give a white solid. The solid was dried under high vacuum to constant weight to give the title compound, 80 mg (86%). MS m/z: Calculated: 346.22. Observed: 347.

Method 6. Preparation of tert-Butyl 2-(5-hydroxy-8-methyl-2-(methylsulfonyl)-7-oxo-7,8-dihydropyrido[2,3-d]pyrimidine-6-carboxamido)acetate

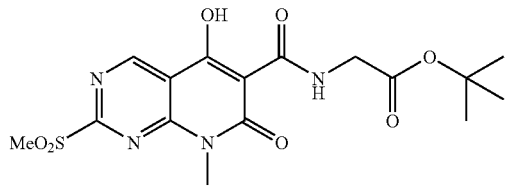

(a) Methyl 5-hydroxy-8-methyl-2-(methylthio)-7-oxo-7,8-dihydropyrido[2,3-d]pyrimidine-6-carboxylate. The title compound was prepared as described in Method 5(a)-5(c) using ethyl 4-chloro-2-(methylthio)pyrimidine-5-carboxylate as the starting material.

(b) tert-Butyl 2-(5-hydroxy-8-methyl-2-(methylthio)-7-oxo-7,8-dihydropyrido[2,3-d']pyrimidine-6-carboxamido)acetate. A solution of methyl 5-hydroxy-8-methyl-2-(methylthio)-7-oxo-7,8-dihydropyrido[2,3-d]pyrimidine-6-carboxylate (3 g), glycine tert-butyl ester hydrochloride (3.6 g), DIPEA (6 mL), and 1,4-dioxane (100 mL) was heated to 100° C. After 2 hours, the reaction was concentrated in vacuo and washed with EtOAc. Added water and filtered off undissolved solid to give the title compound (2.3 g). MS m/z: Calculated: 380.42. Observed: 381.

(c) tert-Butyl 2-(5-hydroxy-8-methyl-2-(methylsulfonyl)-7-oxo-7,8-dihydropyrido[2,3-d]pyrimidine-6-carboxamido)acetate. To a solution of tert-butyl 2-(5-hydroxy-8-methyl-2-(methylthio)-7-oxo-7,8-dihydropyrido[2,3-d]pyrimidine-6-carboxamido)acetate (1 g, 3 mmol) and DCM (50 mL) was added MCPBA (1.3 g, 8 mmol). The reaction was then stirred at room temperature. After 1 hour, the starting material had disappeared and the sulphone and sulfoxide products were observed by LCMS. After 2 more hours, 1 g of MCPBA was added. After another hour, the reaction was determined to be complete by LCMS. The mixture was concentrated under reduced pressure and washed with MeOH and filtered through Celite. The white solid on the Celite was determined to be the product by $^1$H NMR. The produce was dissolved in DCM and concentrated under reduced pressure. The resulting solid was dissolved in 3:1 EtOAc/DCM and washed with water and brine, and then dried with MgSO$_4$ and concentrated under reduced pressure to give 1 g of a white solid MS m/z: Calculated: 412.42. Observed: 413.

Method 7. Preparation of 2-(5-Hydroxy-8-methyl-7-oxo-2-(piperidin-1-yl)-7,8-dihydropyrido[2,3-d]pyrimidine-6-carboxamido)acetic acid

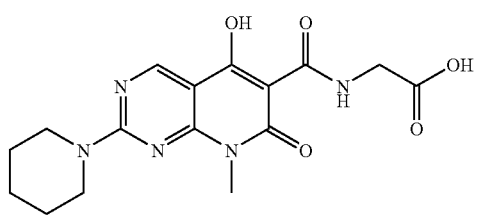

(a) tert-Butyl 2-(5-hydroxy-8-methyl-7-oxo-2-(piperidin-1-yl)-7,8-dihydropyrido[2,3-d]pyrimidine-6-carboxamido) acetate. A solution of tert-butyl 2-(5-hydroxy-8-methyl-2-(methylsulfonyl)-7-oxo-7,8-dihydropyrido[2,3-d]pyrimidine-6-carboxamido)acetate (100 mg, 0.24 mmol) and THF (5 mL) was treated with piperidine (0.1 mL, 1.2 mmol) and heated to 180° C. in a microwave (Biotage) for 10 minutes. The reaction mixture was then concentrated under vacuum and the solid was washed with ether. The white solid was then collected by filtration. The product was used in the next step without further purification.

(b) 2-(5-Hydroxy-8-methyl-7-oxo-2-(piperidin-1-yl)-7,8-dihydropyrido[2,3-d]pyrimidine-6-carboxamido)acetic acid. A solution of tert-butyl 2-(5-hydroxy-8-methyl-7-oxo-2-(piperidin-1-yl)-7,8-dihydropyrido[2,3-d]pyrimidine-6-carboxamido)acetate (101 mg, 0.24 mmol) and TFA (19 µl, 0.24 mmol) was stirred at room temperature. After 30 minutes, the reaction was determined to be complete by LCMS. The reaction was concentrated under reduced pressure to give a yellow oil. Water was added to the residue and a white precipitate formed. The solid was filtered and washed with water. The solid was dried under high-vacuum to give the title compound as a white solid (25 mg). MS m/z: Calculated: 361.35. Observed: 362. $^1$H NMR (300 MHz, DMSO-d$_6$) δ ppm 12.90 (1H, br. s.), 9.97-10.32 (1H, m), 8.88 (1H, s), 4.03-4.13 (2H, m), 3.91 (4H, s), 3.49 (3H, s), 1.47-1.76 (6H, m).

Method 8. Preparation of 2-(5-Hydroxy-2-methoxy-8-methyl-7-oxo-7,8-dihydropyrido[2,3-d]pyrimidine-6-carboxamido)acetic acid

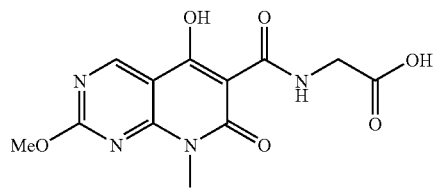

(a) tert-Butyl 2-(5-hydroxy-2-methoxy-8-methyl-7-oxo-7,8-dihydropyrido[2,3-d]pyrimidine-6-carboxamido)acetate. To a mixture of tert-butyl 2-(5-hydroxy-8-methyl-2-(methylsulfonyl)-7-oxo-7,8-dihydropyrido[2,3-d]pyrimidine-6-carboxamido)acetate (141 mg, 0.34 mmol) and THF (10 mL) was added ammonia, 2.0M methyl alcohol (3 mL, 5.1 mmol) at 0° C. under N$_2$. The mixture was then stirred at 0° C. and warmed to room temperature overnight. LCMS showed no starting material was left and two peaks corresponding to the 7-amino and to the 7-OMe product (ca. 1:1). The white solid was filtered off and discarded. The filtrate was concentrated under reduced pressure to give the title compound. MS m/z: Calculated: 364.35. Observed: 365.

(b) 2-(5-Hydroxy-2-methoxy-8-methyl-7-oxo-7,8-dihydropyrido[2,3-d]pyrimidine-6-carboxamido)acetic acid. A solution of tert-butyl 2-(5-hydroxy-2-methoxy-8-methyl-7-oxo-7,8-dihydropyrido[2,3-d]pyrimidine-6-carboxamido)acetate (100 mg, 0.27 mmol) and TFA (3 mL) was stirred at room temperature. After 30 minutes, the reaction was determined to be complete by LCMS. The reaction was concentrated under reduced pressure to give a yellow oil. Water was added, and a white precipitate formed. The solid was filtered, washed with water, and then washed with hexane. The product was then dried under high vacuum to provide 50 mg of the produce as an off-white solid (59%). MS m/z: Calculated: 308.25. Observed: 309.

TABLE 2

The following table lists compounds which were prepared by the methods described above.

| Ex. | Structure | Name | $^1$H NMR (δ ppm) | Method |
|---|---|---|---|---|
| 10 | 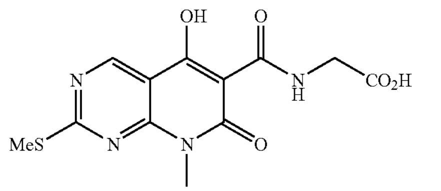 | 2-(5-hydroxy-8-methyl-2-(methylthio)-7-oxo-7,8-dihydropyrido[2,3-d]pyrimidine-6-carboxamido)acetic acid | 12.94 (1 H, br. s.), 9.90-10.41 (1 H, m), 8.79-9.27 (1 H, m), 4.04-4.23 (2 H, m), 3.51-3.67 (3 H, m), 2.58-2.68 (3 H, m). | 5, 6 |
| 11 | 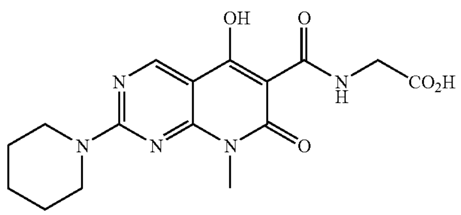 | 2-(5-hydroxy-8-methyl-7-oxo-2-(piperidin-1-yl)-7,8-dihydropyrido[2,3-d]pyrimidine-6-carboxamido)acetic acid | 12.90 (1 H, br. s.), 9.97-10.32 (1 H, m), 8.88 (1 H, s), 4.03-4.13 (2 H, m), 3.91 (4 H, s), 3.49 (3 H, s), 1.47-1.76 (6 H, m). | 5, 6, 7 |
| 12 | 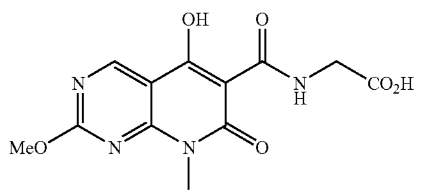 | 2-(5-hydroxy-2-methoxy-8-methyl-7-oxo-7,8-dihydropyrido[2,3-d]pyrimidine-6-carboxamido)acetic acid | 12.97 (1 H, s), 10.14 (1 H, s), 9.12 (1 H, s), 4.12 (2 H, d, J = 5.1 Hz), 4.06 (3 H, s), 3.57 (3 H, s). | 5, 6, 8 |
| 13 | 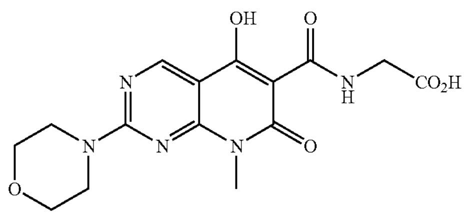 | 2-(5-hydroxy-8-methyl-2-morpholino-7-oxo-7,8-dihydropyrido[2,3-d]pyrimidine-6-carboxamido)acetic acid | 11.46 (1 H, s), 9.92-10.49 (1 H, m), 8.93 (1 H, s), 4.16 (2 H, d, J = 5.5 Hz), 3.98 (4 H, br. s.), 3.69-3.78 (4 H, m), 3.59 (3 H, s). | 5, 6, 7 |
| 14 | 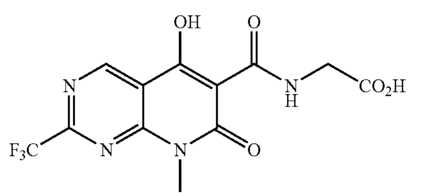 | 2-(5-hydroxy-8-methyl-7-oxo-2-(trifluoromethyl)-7,8-dihydropyrido[2,3-d]pyrimidine-6-carboxamido)acetic acid | 10.18 (1 H, br. s.), 9.49 (1 H, s), 4.16 (2 H, d, J = 5.7 Hz), 3.63 (3 H, s). | 5 |
| 15 | 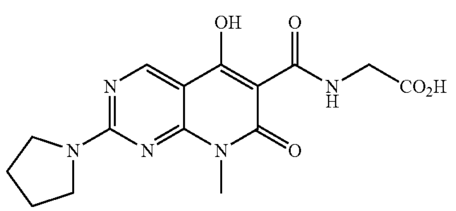 | 2-(5-hydroxy-8-methyl-7-oxo-2-(pyrrolidin-1-yl)-7,8-dihydropyrido[2,3-d]pyrimidine-6-carboxamido)acetic acid | 12.88 (1 H, br. s.), 10.15 (1 H, t, J = 6.7 Hz), 8.89 (1 H, s), 4.09 (2 H, d, J = 0.8 Hz), 3.57-3.66 (4 H, m), 3.51 (3 H, s), 1.84-2.02 (4 H, m) | 5, 6, 7 |
| 16 | 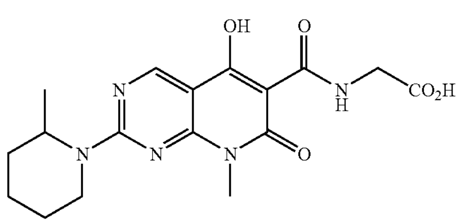 | 2-(5-hydroxy-8-methyl-2-(2-methylpiperidin-1-yl)-7-oxo-7,8-dihydropyrido[2,3-d]pyrimidine-6-carboxamido)acetic acid | 10.14 (1 H, t, J = 5.5 Hz), 8.89 (1 H, s), 4.09 (2 H, d, J = 5.7 Hz), 3.49 (3 H, s), 3.07 (1 H, t, J = 12.3 Hz), 1.49-1.96 (6 H, m), 1.22 (3 H, d, J = 6.8 Hz). | 5, 6, 7 |

| Ex. | Structure | Name | $^1$H NMR (δ ppm) | Method |
|---|---|---|---|---|
| 17 | 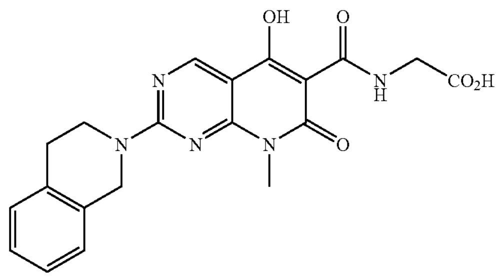 | 2-(2-(3,4-dihydroquinolin-1(2H)-yl)-5-hydroxy-8-methyl-7-oxo-7,8-dihydropyrido[2,3-d]pyrimidine-6-carboxamido)acetic acid | 10.15 (1 H, t, J = 5.5 Hz), 8.95 (1 H, s), 7.30 (1 H, br. s.), 7.22 (3 H, d, J = 2.2 Hz), 5.03 (2 H, d, J = 5.4 Hz), 4.06-4.22 (4 H, m), 3.47-3.61 (5 H, m) | 5, 6, 7 |

Method 9. Preparation of 2-(8-Hydroxy-5-methyl-6-oxo-3-phenyl-5,6-dihydropyrido[3,2-b]pyrazine-7-carboxamido)acetic acid

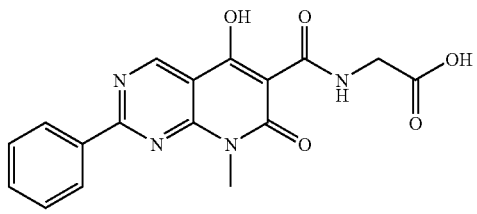

(a) Methyl 3-aminopyrazine-2-carboxylate 4-oxide. A solution of methyl 3-amino-2-pyrazinecarboxylate (2962 mg, 19.3 mmol) in CHCl$_3$ (32 mL) was treated with MCPBA (4450 mg, 19.3 mmol). After all the solids had dissolved (5 minutes), the reaction was heated to 70° C. The reaction was removed from the oil bath after 1 hour and chilled in an ice-water bath. The reaction was stored at –20° C. overnight. The precipitate was collected by filtration, washed with diethyl ether (2×30 mL) and dried under vacuum, affording 2857 mg (87%) of methyl 3-aminopyrazine-2-carboxylate 4-oxide as a yellow solid. Mass: Calculated: 169.138. Observed: 170.1 (M+H)$^+$. $^1$H NMR (400 MHz, DMSO-d$_6$) δ ppm 8.41 (1H, d, J=3.5 Hz), 7.85 (1H, d, J=3.5 Hz), 3.88 (3H, s).

(b) Methyl 3-amino-5-chloropyrazine-2-carboxylate. A suspension of methyl 3-aminopyrazine-2-carboxylate 4-oxide (2845 mg, 16.8 mmol) in DMF (25 mL) was treated with phosphorous oxychloride (7839 μl, 84.1 mmol). The reaction was heated at 80° C. for 15 minutes. The reaction mixture was poured into an ice-water mixture (200 mL) and allowed to stand at 23° C. After 18 hours, the precipitated solid was collected by filtration, washed with water (200 mL) and dried under vacuum, affording 1493 mg (47%) of methyl 3-amino-5-chloropyrazine-2-carboxylate as an off-white solid. Mass: Calculated: 187.584. Observed: 188.0 (M+H)$^+$; $^1$H NMR (400 MHz, MeOH-d$_4$) δ ppm 7.83 (1H, s), 3.91-3.95 (3H, m).

(c) Methyl 3-amino-5-phenylpyrazine-2-carboxylate. Methyl 3-amino-5-chloropyrazine-2-carboxylate (307 mg, 1637 μmol), phenylboronic acid (399 mg, 3273 μmol), tri-t-butylphosphonium tetrafluoroborate (95.0 mg, 327 μmol) and tris(dibenzylideneacetone)dipalladium (0) (150 mg, 164 μmol) were added to an oven-dried round bottom flask, which was purged through vacuum-argon cycles (3×). Potassium fluoride (285 mg, 4910 μmol) was added under argon, followed by THF (5 mL), and the reaction was stirred at 45° C. After 4 hours, the reaction was cooled to 23° C. and was filtered through a silica gel plug. The silica gel was washed with a 10% MeOH/DCM solution (250 mL), and the combined filtrate was concentrated in vacuo and purified on silica gel (eluant: 1% MeOH/DCM) to afford 360 mg (96%) of methyl 3-amino-5-phenylpyrazine-2-carboxylate as a dark brown solid. Mass: Calculated: 229.235. Observed: 230.0 (M+H)$^+$; $^1$H NMR (400 MHz, CDCl$_3$) δ ppm 8.48 (1H, s), 8.04 (2H, dd, J=6.6, 2.8 Hz), 7.44-7.58 (3H, m), 4.02 (3H, s).

(d) Methyl 3-(methylamino)-5-phenylpyrazine-2-carboxylate. A solution of methyl 3-amino-5-phenylpyrazine-2-carboxylate (360 mg, 1570 μmol) in DCM (10 mL) was treated with DIPEA (547 μl, 3141 μmol) and trifluoroacetic anhydride (275 μl, 1963 μmol). The reaction stirred under nitrogen at 23° C. After 14 hours, the reaction was diluted with DCM (50 mL) and washed with water (50 mL) and brine (50 mL), dried over MgSO$_4$, and concentrated in vacuo affording methyl 5-phenyl-3-(2,2,2-trifluoroacetamido)pyrazine-2-carboxylate as an orange solid, which was carried forward to the next reaction. A suspension of methyl 5-phenyl-3-(2,2,2-trifluoroacetamido)pyrazine-2-carboxylate (511 mg, 1571 μmol) and potassium carbonate (651 mg, 4713 μmol) in DMF (10 mL) was treated with iodomethane (196 μl, 3142 μmol). The reaction flask was capped with a septum and heated to 65° C. After 4 hours, the reaction was cooled to 23° C., diluted with EtOAc (75 mL) and washed with water (50 mL) and brine (50 mL), dried over MgSO$_4$, concentrated in vacuo and purified by silica gel chromatography (eluant: 5-25% EtOAc/hexane), affording 221 mg (41%, 2 steps) of methyl 5-phenyl-3-(2,2,2-trifluoro-N-methylacetamido)pyrazine-2-carboxylate as an yellow solid. A solution of methyl 5-phenyl-3-(2,2,2-trifluoro-N-methylacetamido)pyrazine-2-carboxylate (253 mg, 746 μmol) in MeOH (2 mL) and DCM (2 mL) was treated with sodium methoxide (0.5M solution in MeOH (2983 μl, 1491 μmol)). The reaction was stirred under nitrogen at 23° C. After 90 minutes, the reaction was diluted with brine (25 mL) and extracted with DCM (3×25 mL). The combined organic layers were dried (MgSO$_4$) and concentrated, affording 179 mg (99%) of methyl 3-(methylamino)-5-phenylpyrazine-2-carboxylate as a yellow solid. Mass: Calculated: 243.261. Observed: 244.0 (M+H)$^+$; $^1$H NMR (400 MHz, CDCl$_3$) δ ppm 8.37 (1H, s), 8.07-8.17 (2H, m), 7.95 (1H, br. s.), 7.46-7.55 (3H, m), 4.00 (3H, s), 3.18 (3H, d, J=4.7 Hz).

(e) Methyl 3-(3-ethoxy-N-methyl-3-oxopropanamido)-5-phenylpyrazine-2-carboxylate. A suspension of methyl 3-(methylamino)-5-phenylpyrazine-2-carboxylate (178 mg, 732 µmol) and potassium carbonate (152 mg, 1098 µmol) in THF (5 mL) was cooled to 0° C. under nitrogen and treated with ethyl malonoyl chloride (115 µl, 915 µmol) in a dropwise fashion. The reaction was slowly warmed to 23° C. After 19 hours, the reaction was diluted with EtOAc (50 mL) and washed with a saturated ammonium chloride solution (50 mL) and brine (50 mL), dried over $MgSO_4$, and concentrated in vacuo affording 260 mg (99%) of methyl 3-(3-ethoxy-N-methyl-3-oxopropanamido)-5-phenylpyrazine-2-carboxylate as a yellow oil. Mass: Calculated: 357.361. Observed: 358.1 $(M+H)^+$.

(f) Ethyl 8-hydroxy-5-methyl-6-oxo-3-phenyl-5,6-dihydropyrido[3,2-b]pyrazine-7-carboxylate. A solution of methyl 3-(3-ethoxy-N-methyl-3-oxopropanamido)-5-phenylpyrazine-2-carboxylate (260 mg, 728 µmol) in EtOH (5 mL) was treated with freshly prepared sodium ethoxide, 1.0 M in EtOH (728 µl, 728 µmol). The reaction was stirred at 23° C. under nitrogen. After 75 minutes, the reaction was filtered. The residue was washed with diethyl ether (25 mL) and dried under vacuum, affording 228 mg (96%) of ethyl 8-hydroxy-5-methyl-6-oxo-3-phenyl-5,6-dihydropyrido[3,2-b]pyrazine-7-carboxylate as an yellow solid. Mass: Calculated: 325.319. Observed: 326.0 (M+H); $^1$H NMR (400 MHz, DMSO-$d_6$) δ ppm 8.82 (1H, s), 8.20 (2H, d, J=7.0 Hz), 7.50-7.60 (3H, m), 4.09 (2H, q, J=6.8 Hz), 3.55 (3H, s), 1.22 (3H, t, J=6.9 Hz).

(g) tert-Butyl 2-(8-hydroxy-5-methyl-6-oxo-3-phenyl-5,6-dihydropyrido[3,2-b]pyrazine-7-carboxamido)acetate. A suspension of ethyl 8-hydroxy-5-methyl-6-oxo-3-phenyl-5,6-dihydropyrido[3,2-b]pyrazine-7-carboxylate (222 mg, 682 µmol), glycine tert-butyl ester hydrochloride (126 mg, 751 µmol) and DIPEA (238 µl, 1365 µmol) in 1,4-dioxane (5 mL) was heated to 120° C. in a sealed vessel. After 15 hours, the reaction was cooled to 23° C. and filtered. The crude residue was washed with water (25 mL) and diethyl ether (5 mL), and dried under vacuum, affording 192 mg (69%) of tert-butyl 2-(8-hydroxy-5-methyl-6-oxo-3-phenyl-5,6-dihydropyrido[3,2-b]pyrazine-7-carboxamido)acetate as an yellow solid. Mass: Calculated: 410.423. Observed: 411.1 $(M+H)^+$; $^1$H NMR (400 MHz, DMSO-$d_6$) δ ppm 9.00 (1H, s), 8.25 (2H, d, J=6.5 Hz), 7.52-7.61 (3H, m), 3.97 (2H, d, J=1.8 Hz), 3.63 (3H, s), 1.44 (9H, s).

(h) 2-(8-Hydroxy-5-methyl-6-oxo-3-phenyl-5,6-dihydropyrido[3,2-b]pyrazine-7-carboxamido)acetic acid. A solution of tert-butyl 2-(8-hydroxy-5-methyl-6-oxo-3-phenyl-5,6-dihydropyrido[3,2-b]pyrazine-7-carboxamido)acetate (185 mg, 451 µmol) in TFA (2 mL) was stirred at 23° C. After 30 minutes, the reaction was concentrated in vacuo and diluted with water (20 mL). The precipitated solids were collected by filtration, washed with diethyl ether (10 mL) and dried under vacuum, affording 151 mg (94%) of 2-(8-hydroxy-5-methyl-6-oxo-3-phenyl-5,6-dihydropyrido[3,2-b]pyrazine-7-carboxamido)acetic acid as an yellow solid. Mass: Calculated: 354.317. Observed: 355.0 $(M+H)^+$; $^1$H NMR (400 MHz, DMSO-$d_6$) δ ppm 10.34-10.53 (1H, m), 9.35 (1H, s), 8.33-8.40 (2H, m), 7.58-7.67 (3H, m), 4.12-4.20 (2H, m), 3.77 (3H, s).

Method 10. Preparation of tert-Butyl 2-(2-chloro-5-hydroxy-8-methyl-7-oxo-7,8-dihydropyrido[2,3-d]pyrimidine-6-carboxamido)acetate

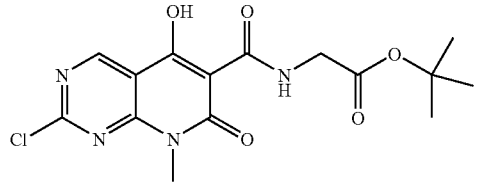

(a) tert-Butyl 2-(5-hydroxy-8-methyl-2-(methylthio)-7-oxo-7,8-dihydropyrido[2,3-d]pyrimidine-6-carboxamido)acetate. A solution of methyl 5-hydroxy-8-methyl-2-(methylthio)-7-oxo-7,8-dihydropyrido[2,3-d]pyrimidine-6-carboxylate (7.5 g, 27 mmol, Method 6a), glycine t-butyl ester (3.5 g, 27 mmol), DIPEA (9.2 mL, 2 54 mmol) in dry dioxane (300 mL) was heated at 100° C. overnight. In order to bring the reaction to completion, 1 equivalent each of glycine t-butyl ester and DIPEA were added after 16 hours. The mixture was then heated for a further 3 hours at 100° C. The solvent was then removed, and the residue was partitioned between $CH_2Cl_2$ and water. The water phase was extracted three times with $CH_2Cl_2$, washed with brine, dried over $Na_2SO_4$ and the solvent removed on the evaporator to obtain the product (9.83 g, 96%) as a yellow-brown solid that was used in the next step without purification. $C_{16}H_{20}N_4O_5S$ (380.4). HPLC (gradient I) $R_t$=3.47 (94). APCI-MS: 381 $([M+H]^+)$. $^1$H-NMR (DMSO-$d_6$): δ 10.16 (br s, 1H), 9.06 (s, 1H), 4.10 (d, J=5.7, 2H), 3.57 (s, 3H), 2.64 (s, 3H), 1.45 (s, 9H).

(b) tert-Butyl 2-(5-hydroxy-8-methyl-2-(methylsulfonyl)-7-oxo-7,8-dihydropyrido[2,3-d]pyrimidine-6-carboxamido)acetate. To a solution of tert-butyl 2-(5-hydroxy-8-methyl-2-(methylthio)-7-oxo-7,8-dihydropyrido[2,3-d]pyrimidine-6-carboxamido)acetate (15.7 g, 41.4 mmol) in dry $CH_2Cl_2$ (600 mL) was added mCPBA (30.6 g, 124 mmol) at 0° C. The mixture was stirred at room temperature for 40 minutes. To the reaction mixture, was added an aqueous $NaHCO_3$ solution, and the water phase was extracted three times with $CH_2Cl_2$, washed with $Na_2S_2O_3$, $NaHCO_3$, brine, dried over $Na_2SO_4$ and the solvent removed on the evaporator to obtain the product (14.6 g, 86%) as a light brown solid. $C_{16}H_{20}N_4O_7S$ (412.4). APCI-MS: 413 $([M+H]^+)$, 325 ([M-(t-Bu)+H]$^+$). $^1$H-NMR (DMSO-$d_6$): δ 10.16 (br s, 1H), 9.49 (s, 1H), 4.13 (d, J=5.8, 2H), 3.66 (s, 3H), 3.51 (s, 3H), 1.45 (s, 9H).

(c) tert-Butyl 2-(2-amino-5-hydroxy-8-methyl-7-oxo-7,8-dihydropyrido[2,3-d]pyrimidine-6-carboxamido)acetate. Ammonia (0.5 M in dioxane, 1 L, 500 mmol) was added to tert-butyl 2-(5-hydroxy-8-methyl-2-(methylsulfonyl)-7-oxo-7,8-dihydropyrido[2,3-d]pyrimidine-6-carboxamido)acetate (14.6 g, 35 mmol) at 0° C. The mixture was stirred at room temperature for 1 hour, and then the white solid was filtered off and washed with dioxane and ether. The product was obtained (11 g, 90%) as a white powder. $C_{15}H_{19}N_5O_5$ (349.3). APCI-MS: 350 $([M+H]^+)$, 294 ([M-(t-Bu)+H]$^+$). $^1$H-NMR (DMSO-$d_6$): δ 10.16 (t, J=5.6, 1H), 8.82 (s, 1H), 7.71 (s, 2H), 4.05 (d, J=5.6, 2H), 3.48 (s, 3H), 1.44 (s, 9H).

(d) tert-Butyl 2-(2-chloro-5-hydroxy-8-methyl-7-oxo-7,8-dihydropyrido[2,3-d]pyrimidine-6-carboxamido)acetate. To a mixture of tert-butyl 2-(2-amino-5-hydroxy-8-methyl-7- oxo-7,8-dihydropyrido[2,3-d]pyrimidine-6-carboxamido)acetate (10 g, 26 mmol) in dichloroethane (1.5 l) was added chlorotrimethylsilane (22 ml, 172 mmol). The mixture was stirred 5 minutes at 0° C. and then for 15 minutes at room temperature. The mixture was again cooled to 0° C. and t-butyl-nitrite (24.2 ml, 179 mmol) was added. The resulting solution was stirred at 70° C. for 1.5 hours. The reaction was not complete so a second portion of the two reagents were added again following the same procedure as before. After stirring the mixture at 70° C. for an additional 1.5 hours, the mixture was cooled to room temperature and quenched with a saturated NaHCO$_3$ solution. The phases were separated and extracted with more CH$_2$Cl$_2$. The combined organic phases were washed with water and brine, dried over Na$_2$SO$_4$ and concentrated to yield the product (4.8 g, 44%) as a yellow solid. C$_{15}$H$_{17}$ClN$_4$O$_5$ (368.8). HPLC (gradient E) R$_t$=4.39 (82). APCI-MS: 369 ([M+H]$^+$). $^1$H-NMR (DMSO-d$_6$): δ 10.11 (br s, 1H), 9.20 (s, 1H), 4.10 (d, J=5.8, 2H), 3.56 (s, 3H), 1.43 (s, 9H).

Method 11. Preparation of 2-(2-(3-Fluorophenyl)-5-hydroxy-8-methyl-7-oxo-7,8-dihydropyrido[2,3-d]pyrimidine-6-carboxamido)acetic acid

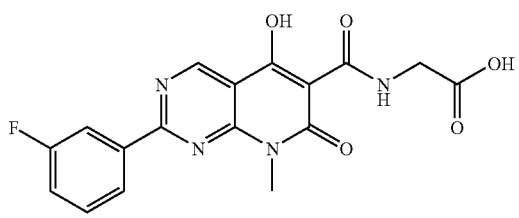

(a) tert-Butyl 2-(2-(3-fluorophenyl)-5-hydroxy-8-methyl-7-oxo-7,8-dihydropyrido[2,3-d]pyrimidine-6-carboxamido)acetate. To a mixture of tert-butyl 2-(2-chloro-5-hydroxy-8-methyl-7-oxo-7,8-dihydropyrido[2,3-d]pyrimidine-6-carboxamido)acetate (100 mg, 1 eq., Method 10), Pd(dppf)Cl$_2$ (0.05 eq.), 3-fluorophenylboronic acid (3.0 eq., available from Aldrich (Milwaukee, Wis.)) in degassed dioxane (4 mL) was added degassed aqueous Na$_2$CO$_3$ (2M, 3 eq.) in a sealed tube. The mixture was stirred overnight at 80° C. The mixture was then cooled to room temperature and diluted with water. The phases were separated and extracted with more CH$_2$Cl$_2$. The combined organic phases were washed with water and brine, dried over Na$_2$SO$_4$ and concentrated. The residue was dissolved in DMA and purified on reversed phase HPLC to give the title compound (48 mg, 41%) as a light brown solid. C$_{21}$H$_{21}$FN$_4$O$_5$ (428.4). APCI-MS: 429 ([M+H]$^+$), 373 ([M-(t-Bu)+H]$^+$). $^1$H-NMR (DMSO-d$_6$): δ 10.21 (br s, 1H), 9.39 (s, 1H), 8.40 (d, J=7.8, 1H), 8.25 (d, J=9.3, 1H), 7.66 (q, J=8.1, 1H), 7.49 (dt, J=8.5, 2.5, 1H), 4.13 (d, J=5.7, 2H), 3.55 (s, 3H), 1.46 (s, 9H).

(b) 2-(2-(3-Fluorophenyl)-5-hydroxy-8-methyl-7-oxo-7,8-dihydropyrido[2,3-d]pyrimidine-6-carboxamido)acetic acid. tert-Butyl 2-(2-(3-fluorophenyl)-5-hydroxy-8-methyl-7-oxo-7,8-dihydropyrido[2,3-d]pyrimidine-6-carboxamido)acetate (41 mg, 0.096 mmol) was dissolved in CH$_2$Cl$_2$ (1 mL) and cooled to 0° C. Trifluoroacetic acid (1 mL) was added and the reaction was stirred at room temperature for 2 hours. The reaction mixture was concentrated, coevaporated with more CH$_2$Cl$_2$ and washed with Et$_2$O to afford the product (30 mg, 67%) as a brown solid. C$_{17}$H$_{13}$FN$_4$O$_5$ (372.3). HPLC (gradient E) R$_t$=4.37 (96). APCI-MS: 373 ([M+H]$^+$). $^1$H-NMR (DMSO-d$_6$): δ 10.21 (br s, 1H), 9.40 (s, 1H), 8.40 (d, J=7.7, 1H), 8.23 (d, J=9.3, 1H), 7.66 (q, J=8.0, 1H), 7.50 (dt, J=8.6, 2.6, 1H), 4.16 (d, J=5.6, 2H), 3.75 (s, 3H).

Method 12. Preparation of 2-(2-Cyclopropyl-5-hydroxy-8-methyl-7-oxo-7,8-dihydropyrido[2,3-d]pyrimidine-6-carboxamido)acetic acid

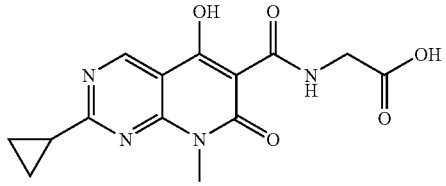

(a) tert-Butyl 2-(2-cyclopropyl-5-hydroxy-8-methyl-7-oxo-7,8-dihydropyrido[2,3-d]pyrimidine-6-carboxamido)acetate. A mixture of tert-butyl 2-(2-chloro-5-hydroxy-8-methyl-7-oxo-7,8-dihydropyrido[2,3-d]pyrimidine-6-carboxamido)acetate (80 mg, 0.22 mmol, Method 10), cyclopropylboronic acid (186 mg, 2 mmol, available from Aldrich (Milwaukee, Wis.)), Pd(OAc)$_2$ (2 mg, 0.01 mol), tricyclohexylphosphine (6 mg, 0.02 mmol), potassium phosphate (161 mg, 0.79 mmol) in degassed toluene (2 mL) and water (0.1 mL) in a sealed tube was stirred overnight at 110° C. The mixture was then cooled to room temperature and diluted with water. The phases were separated and extracted with more CH$_2$Cl$_2$. The combined organic phases were then washed with water and brine, dried over Na$_2$SO$_4$ and concentrated. The residue was dissolved in DMA and purified on reverse phase HPLC to afford the product (10 mg, 13%) as a brown solid. C$_{18}$H$_{22}$N$_4$O$_5$ (374.4). HPLC (gradient J) R$_t$=1.51 (96). APCI-MS: 375 ([M+H]$^+$), 319 ([M-(t-Bu)+H]$^+$).

(b) 2-(2-Cyclopropyl-5-hydroxy-8-methyl-7-oxo-7,8-dihydropyrido[2,3-d]pyrimidine-6-carboxamido)acetic acid. tert-Butyl 2-(2-cyclopropyl-5-hydroxy-8-methyl-7-oxo-7,8-dihydropyrido[2,3-d]pyrimidine-6-carboxamido)acetate (10 mg, 0.027 mmol) was dissolved in CH$_2$Cl$_2$ (0.5 mL) and cooled to 0° C. Trifluoroacetic acid (0.5 mL) was added, and the reaction was stirred at room temperature for 2 hours. The reaction mixture was concentrated, coevaporated with more CH$_2$Cl$_2$ and washed with CH$_2$Cl$_2$ to afford the product (4.3 mg, 34%) as a brown solid. C$_{14}$H$_{14}$N$_4$O$_5$ (318.3). HPLC (gradient E) R$_t$=2.00 (88). APCI-MS: 319 ([M+H]$^+$). $^1$H-NMR (DMSO-d$_6$): δ 10.22 (br s, 1H), 9.14 (s, 1H), 4.13 (d, J=5.6, 2H), 3.60 (s, 3H), 1.20-1.16 (m, 4H).

Method 13. Preparation of 2-(2-(2-Cyclopropylethynyl)-5-hydroxy-8-methyl-7-oxo-7,8-dihydropyrido[2,3-d]pyrimidine-6-carboxamido)acetic acid

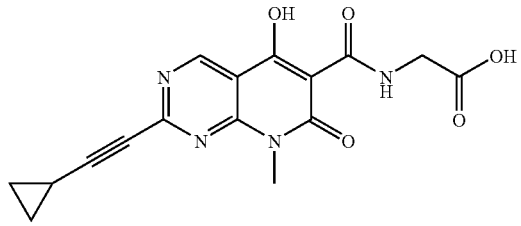

(a) tert-Butyl 2-(2-(2-cyclopropylethynyl)-5-hydroxy-8-methyl-7-oxo-7,8-dihydropyrido[2,3-d]pyrimidine-6-carboxamido)acetate. A mixture of tert-butyl 2-(2-chloro-5-hydroxy-8-methyl-7-oxo-7,8-dihydropyrido[2,3-d]pyrimidine-6-carboxamido)acetate (80 mg, 0.22 mmol, Method 10), ethynylcyclopropane (70% in toluene, 92 mg, 1.1 mmol, available from Aldrich (Milwaukee, Wis.)), Pd(PPh₃)₂Cl₂ (16 mg, 0.02 mol), PPh₃ (12 mg, 0.04 mmol), CuI (8 mg, 0.04 mmol), Et₃N (0.44 mmol) in DMF (1.5 mL) in a tube was stirred 20 minutes at 120° C. in a microwave. The mixture was then cooled to room temperature, and diluted with water. The phases were separated and extracted with more CH₂Cl₂. The combined organic phases were washed with water and brine, dried over Na₂SO₄ and concentrated. The residue was dissolved in DMA and purified on reverse phase HPLC to afford the product (20 mg, 23%) as a light brown solid. C₂₀H₂₂N₄O₅ (398.4). APCI-MS: 399 ([M+H]⁺).

(b) 2-(2-(2-Cyclopropylethynyl)-5-hydroxy-8-methyl-7-oxo-7,8-dihydropyrido[2,3-d]pyrimidine-6-carboxamido)acetic acid. tert-Butyl 2-(2-(2-cyclopropylethynyl)-5-hydroxy-8-methyl-7-oxo-7,8-dihydropyrido[2,3-d]pyrimidine-6-carboxamido)acetate was dissolved in CH₂Cl₂ (0.5 mL) and cooled to 0° C. Trifluoroacetic acid (0.5 mL) was added, and the reaction was stirred at room temperature for 2 hours. The reaction mixture was concentrated, coevaporated with more CH₂Cl₂ and washed with CH₂Cl₂ to afford the product (4.7 mg, 20%) as a light brown solid. C₁₆H₁₄N₄O₅ (342.3). HPLC (gradient E) R$_f$=2.43 (93). APCI-MS: 343 ([M+H]⁺).

TABLE 3

The following table lists compounds which were prepared by the methods described above.

| Ex. | Structure | Name | ¹H NMR δ ppm) or MS Data (M + H) | Method |
|---|---|---|---|---|
| 18 | 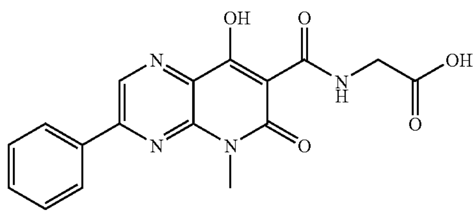 | 2-(8-hydroxy-5-methyl-6-oxo-3-phenyl-5,6-dihydropyrido[3,2-b]pyrazine-7-carboxamido)acetic acid | 10.34-10.53 (1 H, m), 9.35 (1 H, s), 8.33-8.40 (2 H, m), 7.58-7.67 (3 H, m), 4.12-4.20 (2 H, m), 3.77 (3 H, s). | 9 |
| 19 | 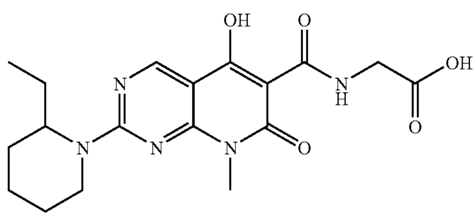 | 2-(2-(2-ethylpiperidin-1-yl)-5-hydroxy-8-methyl-7-oxo-7,8-dihydropyrido[2,3-d]pyrimidine-6-carboxamido)acetic acid | 447 | 7 |
| 20 | 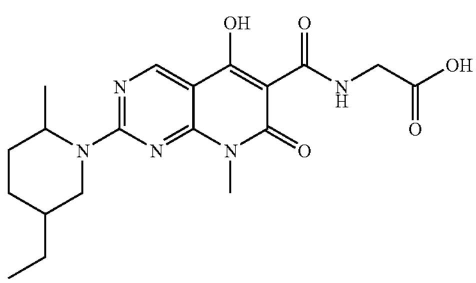 | 2-(2-(5-ethyl-2-methylpiperidin-1-yl)-5-hydroxy-8-methyl-7-oxo-7,8-dihydropyrido[2,3-d]pyrimidine-6-carboxamido)acetic acid | 433 | 7 |
| 21 | 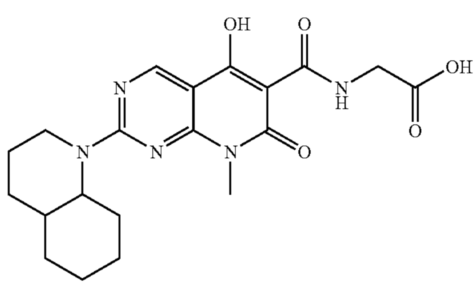 | 2-(5-hydroxy-8-methyl-2-(octahydroquinolin-1(2H)-yl)-7-oxo-7,8-dihydropyrido[2,3-d]pyrimidine-6-carboxamido)acetic acid | 435 | 7 |

TABLE 3-continued

The following table lists compounds which were prepared by the methods described above.

| Ex. | Structure | Name | ¹H NMR δ ppm) or MS Data (M + H) | Method |
|---|---|---|---|---|
| 22 | 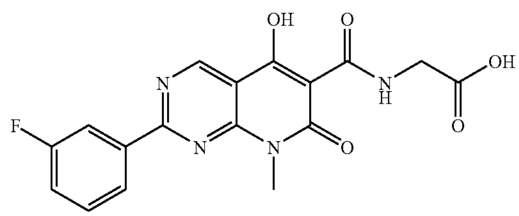 | 2-(2-(3-fluorophenyl)-5-hydroxy-8-methyl-7-oxo-7,8-dihydropyrido[2,3-d]pyrimidine-6-carboxamido)acetic acid | 373 | 11 |
| 23 | 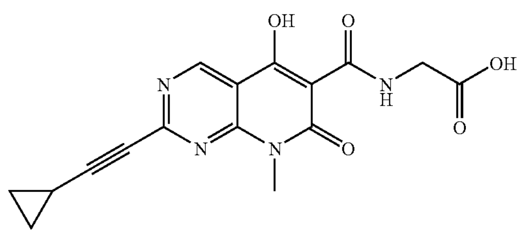 | 2-(2-(2-cyclopropylethynyl)-5-hydroxy-8-methyl-7-oxo-7,8-dihydropyrido[2,3-d]pyrimidine-6-carboxamido)acetic acid | 343 | 13 |
| 24 | 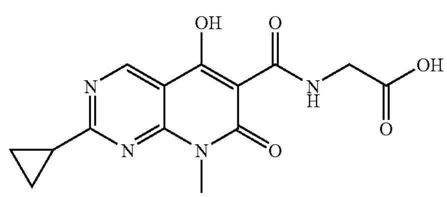 | 2-(2-cyclopropyl-5-hydroxy-8-methyl-7-oxo-7,8-dihydropyrido[2,3-d]pyrimidine-6-carboxamido)acetic acid | 319 | 12 |
| 25 | 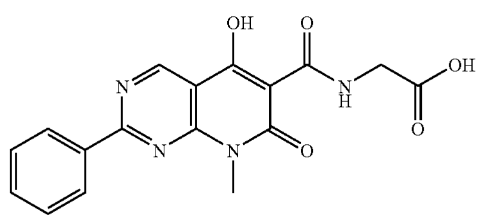 | 2-(5-hydroxy-8-methyl-7-oxo-2-phenyl-7,8-dihydropyrido[2,3-d]pyrimidine-6-carboxamido)acetic acid | 355 | 11 |
| 26 | 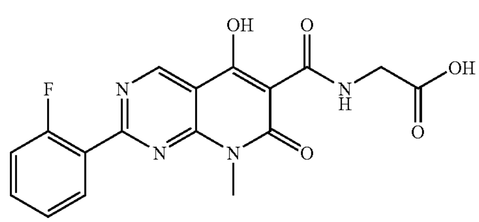 | 2-(2-(2-fluorophenyl)-5-hydroxy-8-methyl-7-oxo-7,8-dihydropyrido[2,3-d]pyrimidine-6-carboxamido)acetic acid | 373 | 11 |
| 27 | 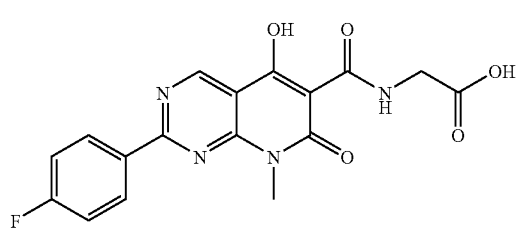 | 2-(2-(4-fluorophenyl)-5-hydroxy-8-methyl-7-oxo-7,8-dihydropyrido[2,3-d]pyrimidine-6-carboxamido)acetic acid | 373 | 11 |

TABLE 3-continued

The following table lists compounds which were prepared by the methods described above.

| Ex. | Structure | Name | ¹H NMR δ ppm) or MS Data (M + H) | Method |
|---|---|---|---|---|
| 28 | 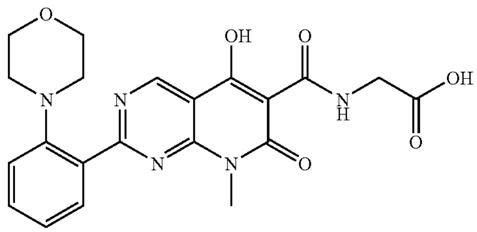 | 2-(5-hydroxy-8-methyl-2-(2-morpholinophenyl)-7-oxo-7,8-dihydropyrido[2,3-d]pyrimidine-6-carbox-amido)acetic acid | 440 | 11 |
| 29 | 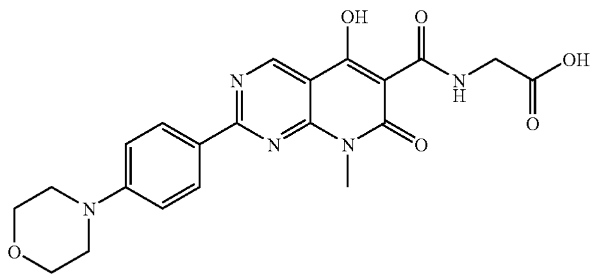 | 2-(5-hydroxy-8-methyl-2-(4-morpholinophenyl)-7-oxo-7,8-dihydropyrido[2,3-d]pyrimidine-6-carbox-amido)acetic acid | 440 | 11 |
| 30 | 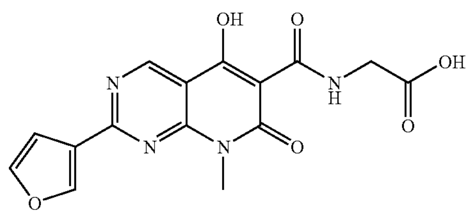 | 2-(2-(furan-3-yl)-5-hydroxy-8-methyl-7-oxo-7,8-dihydropyrido[2,3-d]pyrimidine-6-carbox-amido)acetic acid | 345 | 11 |
| 31 | 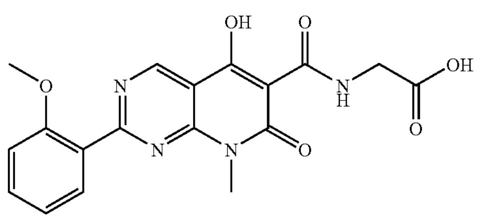 | 2-(5-hydroxy-2-(2-methoxyphenyl)-8-methyl-7-oxo-7,8-dihydropyrido[2,3-d]pyrimidine-6-carbox-amido)acetic acid | 385 | 11 |
| 32 | 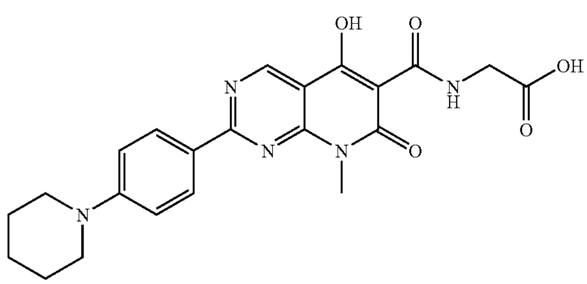 | 2-(5-hydroxy-8-methyl-7-oxo-2-(4-(piperidin-1-yl)phenyl)-7,8-dihydropyrido[2,3-d]pyrimidine-6-carbox-amido)acetic acid | 438 | 11 |
| 33 | 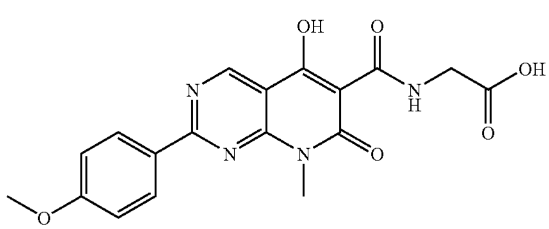 | 2-(5-hydroxy-2-(4-methoxyphenyl)-8-methyl-7-oxo-7,8-dihydropyrido[2,3-d]pyrimidine-6-carbox-amido)acetic acid | 385 | 11 |

TABLE 3-continued

The following table lists compounds which were prepared by the methods described above.

| Ex. | Structure | Name | ¹H NMR δ ppm) or MS Data (M + H) | Method |
|---|---|---|---|---|
| 34 | 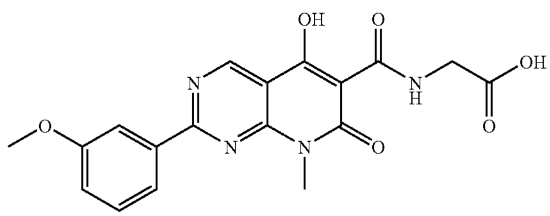 | 2-(5-hydroxy-2-(3-methoxyphenyl)-8-methyl-7-oxo-7,8-dihydropyrido[2,3-d]pyrimidine-6-carboxamido)acetic acid | 385 | 11 |
| 35 | 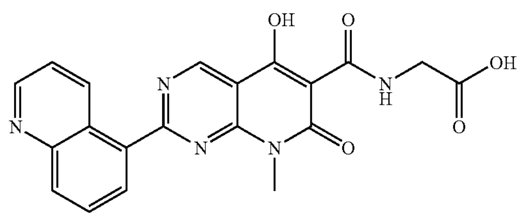 | 2-(5-hydroxy-8-methyl-7-oxo-2-(quinolin-5-yl)-7,8-dihydropyrido[2,3-d]pyrimidine-6-carboxamido)acetic acid | 406 | 11 |
| 36 | 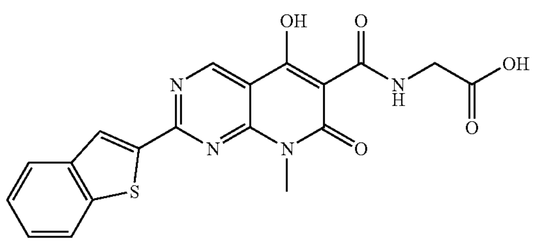 | 2-(2-(benzo[b]thiophen-2-yl)-5-hydroxy-8-methyl-7-oxo-7,8-dihydropyrido[2,3-d]pyrimidine-6-carboxamido)acetic acid | 411 | 11 |
| 37 | 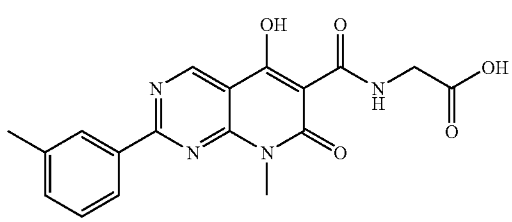 | 2-(5-hydroxy-8-methyl-7-oxo-2-m-tolyl-7,8-dihydropyrido[2,3-d]pyrimidine-6-carboxamido)acetic acid | 369 | 11 |
| 38 | 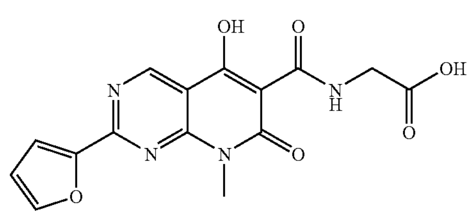 | 2-(2-(furan-2-yl)-5-hydroxy-8-methyl-7-oxo-7,8-dihydropyrido[2,3-d]pyrimidine-6-carboxamido)acetic acid | 345 | 11 |
| 39 | 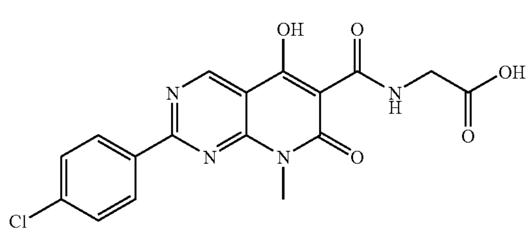 | 2-(2-(4-chlorophenyl)-5-hydroxy-8-methyl-7-oxo-7,8-dihydropyrido[2,3-d]pyrimidine-6-carboxamido)acetic acid | 390 | 11 |

TABLE 3-continued

The following table lists compounds which were prepared by the methods described above.

| Ex. | Structure | Name | $^1$H NMR δ ppm) or MS Data (M + H) | Method |
|---|---|---|---|---|
| 40 | 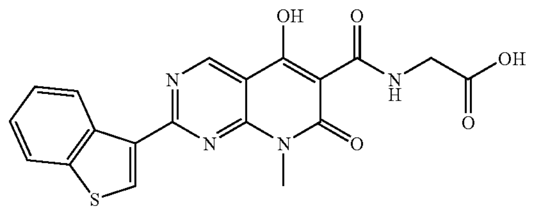 | 2-(2-(benzo[b]thiophen-3-yl)-5-hydroxy-8-methyl-7-oxo-7,8-dihydropyrido[2,3-d]pyrimidine-6-carbox-amido)acetic acid | 411 | 11 |
| 41 | 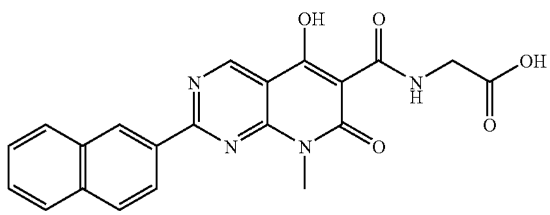 | 2-(5-hydroxy-8-methyl-2-(naphthalen-2-yl)-7-oxo-7,8-dihydropyrido[2,3-d]pyrimidine-6-carbox-amido)acetic acid | 405 | 11 |
| 42 | 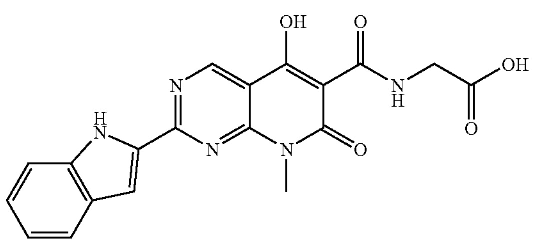 | 2-(5-hydroxy-2-(1H-indol-2-yl)-8-methyl-7-oxo-7,8-dihydropyrido[2,3-d]pyrimidine-6-carbox-amido)acetic acid | 394 | 11 |
| 43 | 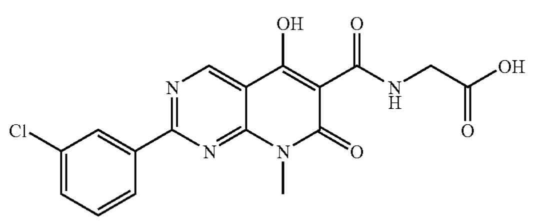 | 2-(2-(3-chlorophenyl)-5-hydroxy-8-methyl-7-oxo-7,8-dihydropyrido[2,3-d]pyrimidine-6-carbox-amido)acetic acid | 390 | 11 |
| 44 | 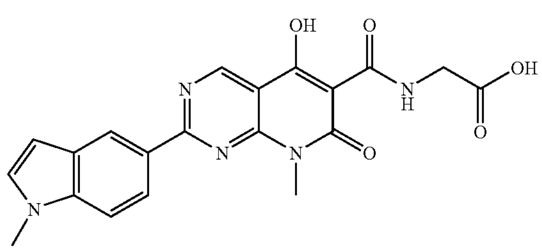 | 2-(5-hydroxy-8-methyl-2-(1-methyl-1H-indol-5-yl)-7-oxo-7,8-dihydropyrido[2,3-d]pyrimidine-6-carbox-amido)acetic acid | 408 | 11 |
| 45 | 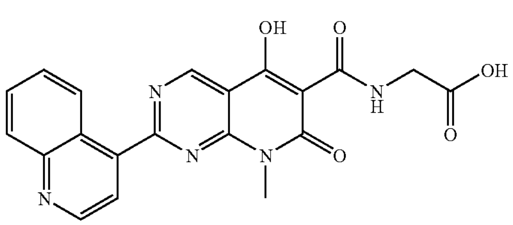 | 2-(5-hydroxy-8-methyl-7-oxo-2-(quinolin-4-yl)-7,8-dihydropyrido[2,3-d]pyrimidine-6-carbox-amido)acetic acid | 406 | 11 |

TABLE 3-continued

The following table lists compounds which were
prepared by the methods described above.

| Ex. | Structure | Name | ¹H NMR δ ppm) or MS Data (M + H) | Method |
|---|---|---|---|---|
| 46 | 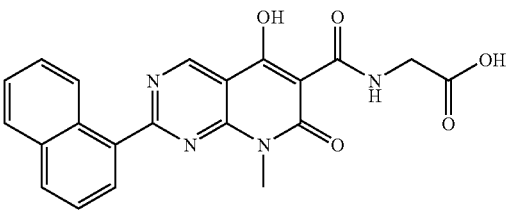 | 2-(5-hydroxy-8-methyl-2-(naphthalen-1-yl)-7-oxo-7,8-dihydropyrido[2,3-d]pyrimidine-6-carbox-amido)acetic acid | 405 | 11 |
| 47 | 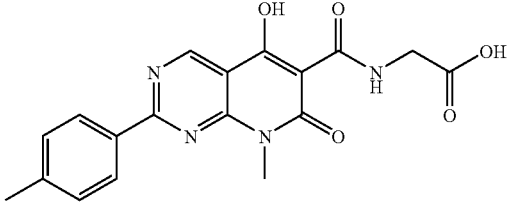 | 2-(5-hydroxy-8-methyl-7-oxo-2-p-tolyl-7,8-dihydropyrido[2,3-d]pyrimidine-6-carbox-amido)acetic acid | 369 | 11 |
| 48 | 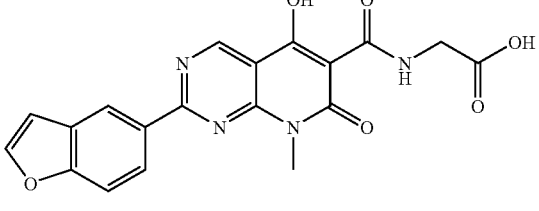 | 2-(2-(benzofuran-5-yl)-5-hydroxy-8-methyl-7-oxo-7,8-dihydropyrido[2,3-d]pyrimidine-6-carbox-amido)acetic acid | 395 | 11 |
| 49 | 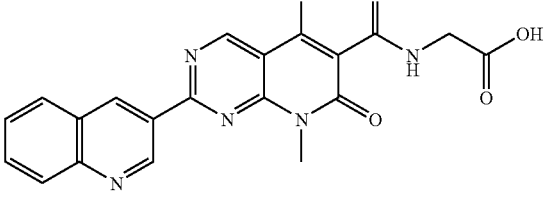 | 2-(5-hydroxy-8-methyl-7-oxo-2-(quinolin-3-yl)-7,8-dihydropyrido[2,3-d]pyrimidine-6-carbox-amido)acetic acid | 406 | 11 |
| 50 | 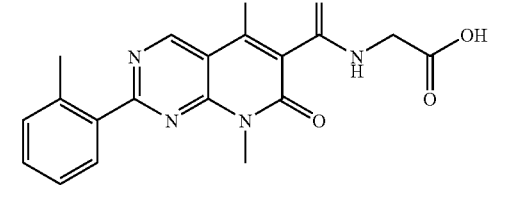 | 2-(5-hydroxy-8-methyl-7-oxo-2-o-tolyl-7,8-dihydropyrido[2,3-d]pyrimidine-6-carbox-amido)acetic acid | 369 | 11 |
| 51 | 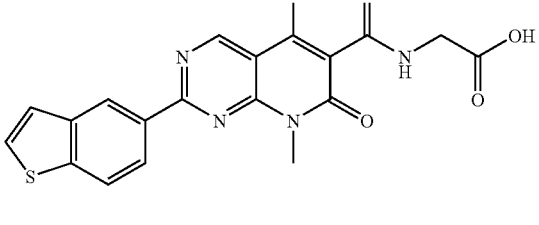 | 2-(2-(benxo[b]thiophen-5-yl)-5-hydroxy-8-methyl-7-oxo-7,8-dihydropyrido[2,3-d]pyrimidine-6-carbox-amido)acetic acid | 411 | 11 |

TABLE 3-continued

The following table lists compounds which were prepared by the methods described above.

| Ex. | Structure | Name | $^1$H NMR δ ppm) or MS Data (M + H) | Method |
|---|---|---|---|---|
| 52 | 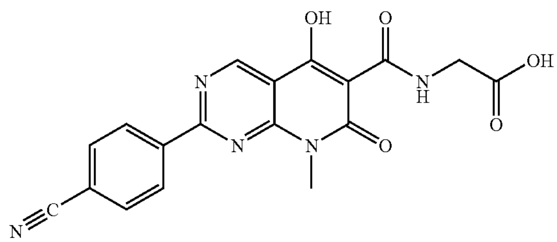 | 2-(2-(4-cyanophenyl)-5-hydroxy-8-methyl-7-oxo-7,8-dihydropyrido[2,3-d]pyrimidine-6-carboxamido)acetic acid | 380 | 11 |
| 53 | 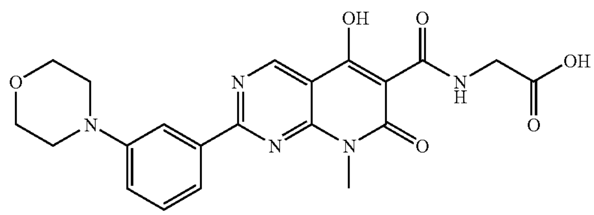 | 2-(5-hydroxy-8-methyl-2-(3-morpholinophenyl)-7-oxo-7,8-dihydropyrido[2,3-d]pyrimidine-6-carboxamido)acetic acid | 440 | 11 |
| 54 | 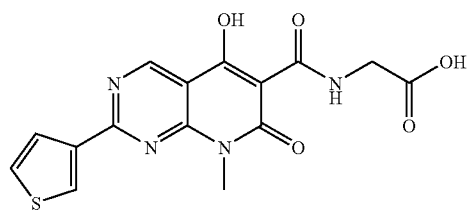 | 2-(5-hydroxy-8-methyl-7-oxo-2-(thiophen-3-yl)-7,8-dihydropyrido[2,3-d]pyrimidine-6-carbox amido)acetic acid | 361 | 11 |
| 55 | 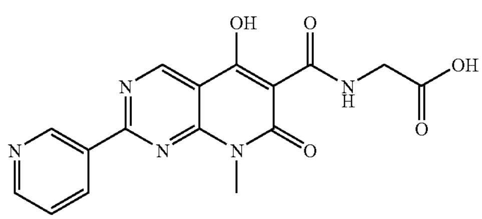 | 2-(5-hydroxy-8-methyl-7-oxo-2-(pyridin-3-yl)-7,8-dihydropyrido[2,3-d]pyrimidine-6-carboxamido)acetic acid | 356 | 11 |
| 56 | 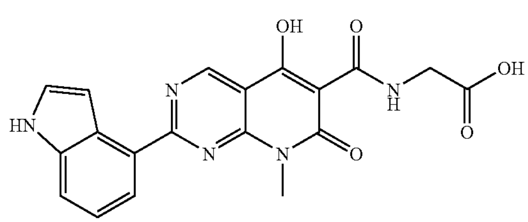 | 2-(5-hydroxy-2-(1H-indol-4-yl)-8-methyl-7-oxo-7,8-dihydropyrido[2,3-d]pyrimidine-6-carboxamido)acetic acid | 394 | 11 |
| 57 | 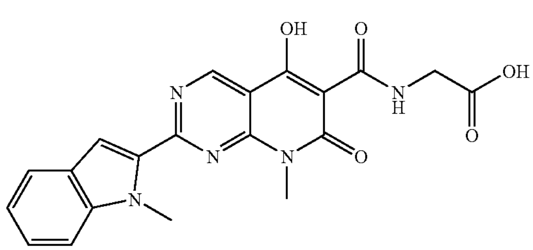 | 2-(5-hydroxy-8-methyl-2-(1-methyl-1H-indol-2-yl)-7-oxo-7,8-dihydropyrido[2,3-d]pyrimidine-6-carboxamido)acetic acid | 408 | 11 |

TABLE 3-continued

The following table lists compounds which were prepared by the methods described above.

| Ex. | Structure | Name | ¹H NMR δ ppm) or MS Data (M + H) | Method |
|---|---|---|---|---|
| 58 | 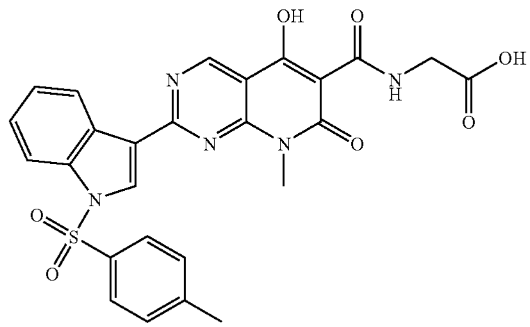 | 2-(5-hydroxy-8-methyl-7-oxo-2-(1-tosyl-1H-indol-3-yl)-7,8-dihydropyrido[2,3-d]pyrimidine-6-carbox-amido)acetic acid | 548 | 11 |

Method 14. Preparation of 6-((Carboxymethyl)carbamoyl)-5-hydroxy-8-methyl-7-oxo-7,8-dihydropyrido[2,3-c]pyridazine-3-carboxylic acid

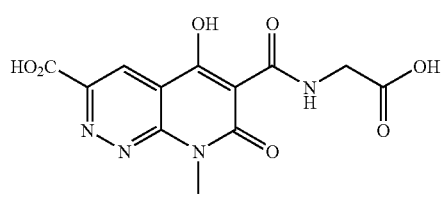

(a) 6-((2-tert-Butoxy-2-oxoethyl)carbamoyl)-5-hydroxy-8-methyl-7-oxo-7,8-dihydropyrido[2,3-c]pyridazine-3-carboxylic acid. The title compound is prepared by a palladium catalyzed carbonylation reaction of tert-butyl 2-(3-chloro-5-hydroxy-8-methyl-7-oxo-7,8-dihydropyrido[2,3-c]pyridazine-6-carboxamido)acetate according to the procedure of Tsuji, J., *Palladium Reagents and catalysts: Innovations in Organic Synthesis* Publisher: (Wiley, Chichester, UK), 340-45 (1995).

(b) 6-((Carboxymethyl)carbamoyl)-5-hydroxy-8-methyl-7-oxo-7,8-dihydropyrido[2,3-c]pyridazine-3-carboxylic acid. The title compound is prepared by acidic deprotection of 6-((2-tert-butoxy-2-oxoethyl)carbamoyl)-5-hydroxy-8-methyl-7-oxo-7,8-dihydropyrido[2,3-c]pyridazine-3-carboxylic acid using TFA according to the procedure described in Method 3(b).

Method 15. Preparation of 2-(2-cyano-5-hydroxy-8-methyl-7-oxo-7,8-dihydropyrido[2,3-d]pyrimidine-6-carboxamido)acetic acid

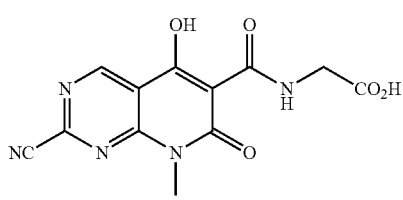

(a) tert-Butyl 2-(2-cyano-5-hydroxy-8-methyl-7-oxo-7,8-dihydropyrido[2,3-d]pyrimidine-6-carboxamido)acetate.

The title compound is prepared by reaction of tert-butyl 2-(5-hydroxy-8-methyl-2-(methylsulfonyl)-7-oxo-7,8-dihydropyrido[2,3-d]pyrimidine-6-carboxamido)acetate with sodium cyanide according to the procedure described in Bioorg. Med. Chem. Lett., 17, 6206 (2007).

(b) 2-(2-Cyano-5-hydroxy-8-methyl-7-oxo-7,8-dihydropyrido[2,3-d]pyrimidine-6-carboxamido)acetic acid. The title compound is prepared by acidic deprotection of tert-butyl 2-(2-cyano-5-hydroxy-8-methyl-7-oxo-7,8-dihydropyrido[2,3-d]pyrimidine-6-carboxamido)acetate according to the procedure described in Method 3(b).

Method 16. Preparation of 6-((carboxymethyl)carbamoyl)-5-hydroxy-8-methyl-7-oxo-7,8-dihydropyrido[2,3-d]pyrimidine-2-carboxylic acid

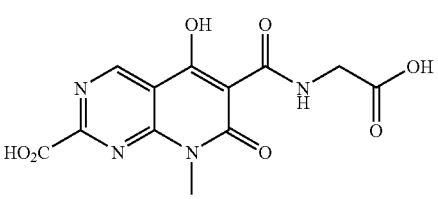

(a) 6-((Carboxymethyl)carbamoyl)-5-hydroxy-8-methyl-7-oxo-7,8-dihydropyrido[2,3-d]pyrimidine-2-carboxylic acid. The title compound is prepared by acidic hydrolysis of the cyano group with accompanying deprotection of tert-butyl 2-(2-cyano-5-hydroxy-8-methyl-7-oxo-7,8-dihydropyrido[2,3-d]pyrimidine-6-carboxamido)acetate according to the procedure described in J. Med. Chem., 50, 3229 (2007) and those described in Method 14(a).

Method 17. Preparation of 2-(5-hydroxy-3-methoxy-8-methyl-7-oxo-7,8-dihydropyrido[2,3-c]pyridazine-6-carboxamido)acetic acid

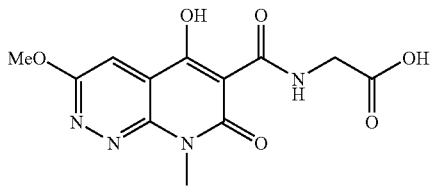

(a) Methyl 5-hydroxy-3-methoxy-8-methyl-7-oxo-7,8-dihydropyrido[2,3-c]pyridazine-6-carboxylate. The title compound is prepared by reaction of methyl 3-chloro-5-hydroxy-8-methyl-7-oxo-7,8-dihydropyrido[2,3-c]pyridazine-6-carboxylate with sodium methoxide according the procedure described in Bioorg. Med. Chem. Lett., 17, 6206 (2007). Alternatively, the title compound is prepared by reaction of methyl 3-chloro-5-hydroxy-8-methyl-7-oxo-7,8-dihydropyrido[2,3-c]pyridazine-6-carboxylate with ammonia in MeOH solution according to Method 8(a).

(b) tert-Butyl 2-(5-hydroxy-3-methoxy-8-methyl-7-oxo-7,8-dihydropyrido[2,3-c]pyridazine-6-carboxamido)acetate. The title compound is prepared from methyl 5-hydroxy-3-methoxy-8-methyl-7-oxo-7,8-dihydropyrido[2,3-c]pyridazine-6-carboxylate and tert-butyl 2-aminoacetate hydrochloride according to Method 3(a).

(c) 2-(5-Hydroxy-3-methoxy-8-methyl-7-oxo-7,8-dihydropyrido[2,3-c]pyridazine-6-carboxamido)acetic acid. The title compound is prepared by deprotection of tert-butyl 2-(5-hydroxy-3-methoxy-8-methyl-7-oxo-7,8-dihydropyrido[2,3-c]pyridazine-6-carboxamido)acetate using TFA according to Method 3(b).

Method 18. Preparation of 2-(5-Hydroxy-8-methyl-7-oxo-3-(piperidin-1-yl)-7,8-dihydropyrido[2,3-c]pyridazine-6-carboxamido)acetic acid

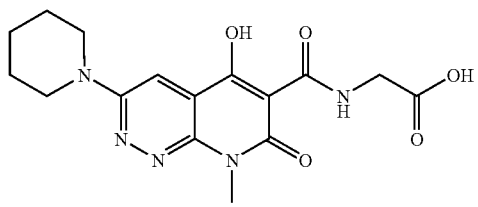

(a) Methyl 5-hydroxy-8-methyl-7-oxo-3-(piperidin-1-yl)-7,8-dihydropyrido[2,3-c]pyridazine-6-carboxylate. The title compound is prepared by reaction of methyl 3-chloro-5-hydroxy-8-methyl-7-oxo-7,8-dihydropyrido[2,3-c]pyridazine-6-carboxylate with piperidine according to literature procedures. Alternatively, the title compound is prepared by reaction of methyl 3-chloro-5-hydroxy-8-methyl-7-oxo-7,8-dihydropyrido[2,3-c]pyridazine-6-carboxylate with piperidine according to Method 7(a).

(b) tert-Butyl 2-(5-hydroxy-8-methyl-7-oxo-3-(piperidin-1-yl)-7,8-dihydropyrido[2,3-c]pyridazine-6-carboxamido)acetate. The title compound is prepared by reaction of methyl 5-hydroxy-8-methyl-7-oxo-3-(piperidin-1-yl)-7,8-dihydropyrido[2,3-c]pyridazine-6-carboxylate and tert-butyl 2-aminoacetate hydrochloride according to Method 3(a).

(c) 2-(5-Hydroxy-8-methyl-7-oxo-3-(piperidin-1-yl)-7,8-dihydropyrido[2,3-c]pyridazine-6-carboxamido)acetic acid. The title compound is deprotected by reaction of tert-butyl 2-(5-hydroxy-8-methyl-7-oxo-3-(piperidin-1-yl)-7,8-dihydropyrido[2,3-c]pyridazine-6-carboxamido)acetate using TFA according to Method 3(b).

TABLE 4

The following table lists compounds which are prepared by the methods described above.

| Ex. | Structure | Name | MW | Method |
|---|---|---|---|---|
| 59 | (structure shown) | 2-(5-hydroxy-8-methyl-7-oxo-7,8-dihydropyrido[2,3-c]pyridazine-6-carboxamido)acetic acid | 278 | 1, 3, 4 b |
| 60 | (structure shown) | 2-(5-hydroxy-8-methyl-7-oxo-3-(pyridin-3-yl)-7,8-dihydropyrido[2,3-c]pyridazine-6-carboxamido)acetic acid | 355 | 1, 2 |

TABLE 4-continued

The following table lists compounds which are prepared by the methods described above.

| Ex. | Structure | Name | MW | Method |
|---|---|---|---|---|
| 61 | 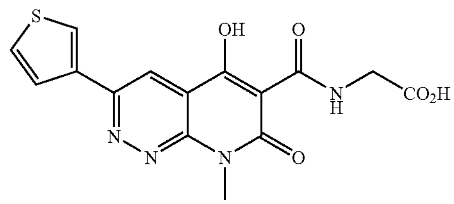 | 2-(5-hydroxy-8-methyl-7-oxo-3-(thiophen-3-yl)-7,8-dihydropyrido[2,3-c]pyridazine-6-carboxamido)acetic acid | 360 | 1, 2 |
| 62 | 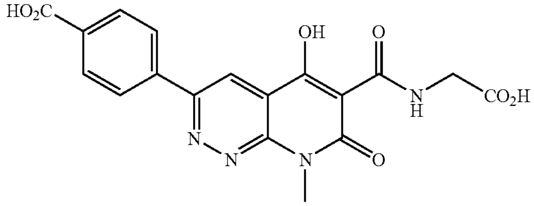 | 4-(6-((carboxymethyl)carbamoyl)-5-hydroxy-8-methyl-7-oxo-7,8-dihydropyrido[2,3-c]pyridazin-3-yl)benzoic acid | 398 | 1, 2 |
| 63 | 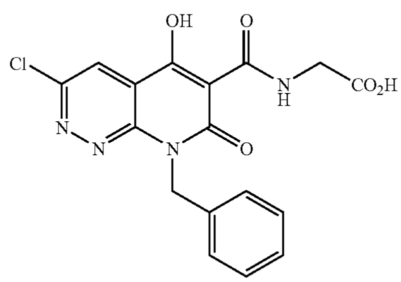 | 2-(8-benzyl-3-chloro-5-hydroxy-7-oxo-7,8-dihydropyrido[2,3-c]pyridazine-6-carboxamido)acetic acid | 388 | 1, 3 |
| 64 | 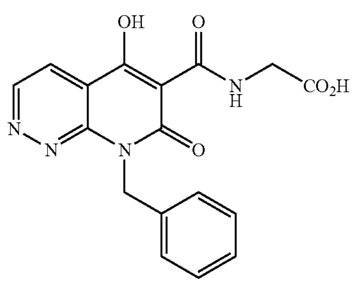 | 2-(8-benzyl-5-hydroxy-7-oxo-7,8-dihydropyrido[2,3-c]pyridazine-6-carboxamido)acetic acid | 354 | 1, 3, 4b |
| 65 | 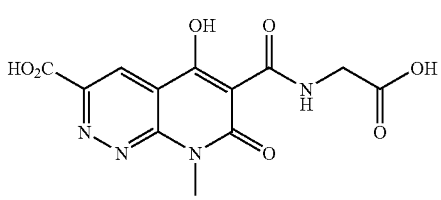 | 6-((carboxymethyl)carbamoyl)-5-hydroxy-8-methyl-7-oxo-7,8-dihydropyrido[2,3-c]pyridazine-3-carboxylic acid | 322 | 1, 3, 14 |
| 66 | 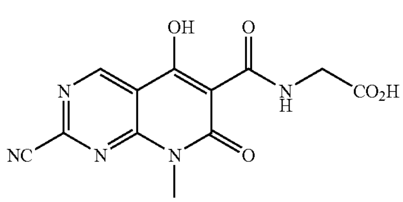 | 2-(2-cyano-5-hydroxy-8-methyl-7-oxo-7,8-dihydropyrido[2,3-d]pyrimidine-6-carboxamido)acetic acid | 303 | 6, 15 |

TABLE 4-continued

The following table lists compounds which are prepared by the methods described above.

| Ex. | Structure | Name | MW | Method |
|-----|-----------|------|-----|--------|
| 67 | 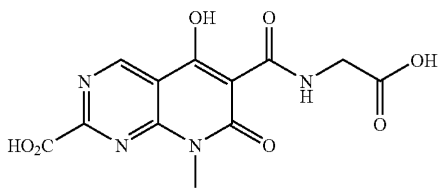 | 6-((carboxymethyl)carbamoyl)-5-hydroxy-8-methyl-7-oxo-7,8-dihydropyrido[2,3-d]pyrimidine-2-carboxylic acid | 322 | 6, 16 |
| 68 | 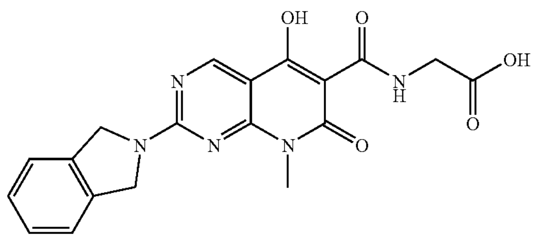 | 2-(5-hydroxy-2-(isoindolin-2-yl)-8-methyl-7-oxo-7,8-dihydropyrido[2,3-d]pyrimidine-6-carboxamido)acetic acid | 395 | 5, 6, 7 |
| 69 | 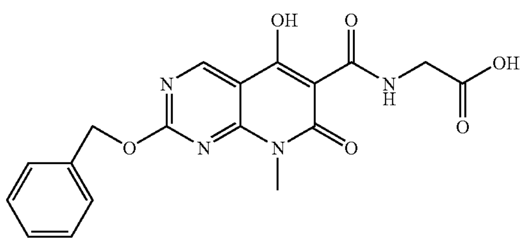 | 2-(2-(benzyloxy)-5-hydroxy-8-methyl-7-oxo-7,8-dihydropyrido[2,3-d]pyrimidine-6-carboxamido)acetic acid | 384 | 5, 6, 8 |
| 70 | 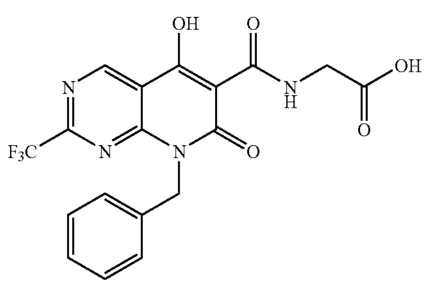 | 2-(8-benzyl-5-hydroxy-7-oxo-2-(trifluoromethyl)-7,8-dihydropyrido[2,3-d]pyrimidine-6-carboxamido)acetic acid | 422 | 5 |
| 71 | 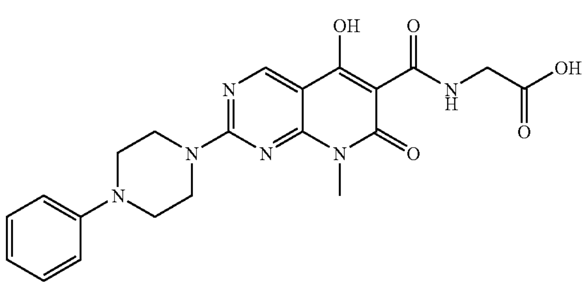 | 2-(5-hydroxy-8-methyl-7-oxo-2-(4-phenylpiperazin-1-yl)-7,8-dihydropyrido[2,3-d]pyrimidine-6-carboxamido)acetic acid | 438 | 5, 6, 7 |
| 72 | 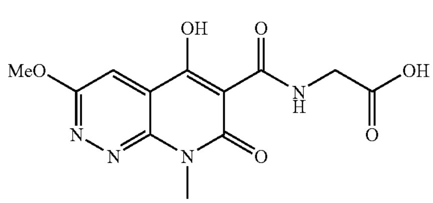 | 2-(5-hydroxy-3-methoxy-8-methyl-7-oxo-7,8-dihydropyrido[2,3-c]pyridazine-6-carboxamido)acetic acid | 308 | 1, 3, 17 |

TABLE 4-continued

The following table lists compounds which are prepared by the methods described above.

| Ex. | Structure | Name | MW | Method |
|---|---|---|---|---|
| 73 | 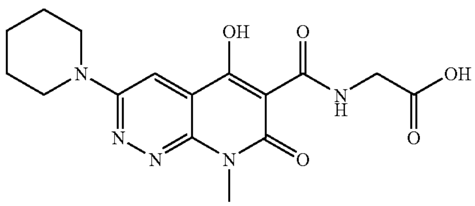 | 2-(5-hydroxy-8-methyl-7-oxo-3-(piperidin-1-yl)-7,8-dihydropyrido[2,3-c]pyridazine-6-carboxamido)acetic acid | 361 | 1, 3, 18 |

The following are examples of methods that may be used to quantitate HIF PHD activity and the inhibition of HIF PHD activity by compounds of the present invention.

Expression, Purification and Europium Labeling of VCB and Design of an Eu-VCB Based TR-FRET Assay for the Detection of Hydroxypropyl HIF1α Peptides The VCB complex is defined as the Von Hippel-Lindau protein (pVHL), elongin B and elongin C heterotrimeric complex. VCB specifically binds to hydroxyproline residues of HIF1α, initiating polyubiquitinylation of HIF1α and its subsequent proteolytic destruction. In the absence of prolyl hydroxylase activity, VCB does not bind unmodified HIF1α. The VCB complex was expressed in *E. coli* and purified from the soluble fraction. The amino acid sequences of the three protein components are as follows:

```
VHL (Amino Acids 54-213)
                                          (SEQ ID NO: 1)
MHHHHHHEAGRPRPVLRSVNSREPSQVIFCNRSPRVVLPVWLNFDGEPQP

YPTLPPGTGRRIHSYRGHLWLFRDAGTHDGLLVNQTELFVPSLNVDGQPI

FANITLPVYTLKERCLQVVRSLVKPENYRRLDIVRSLYEDLEDHPNVQKD

LERLTQERIAHQRMGD

ElonginB
                                          (SEQ ID NO: 2)
MDVFLMIRRHKTTIFTDAKESSTVFELKRIVEGILKRPPDEQRLYKDDQL

LDDGKTLGECGFTSQTARPQAPATVGLAFRADDTFEALCIEPFSSPPELP

DVMKPQDSGSSANEQAVQ*

ElonginC (Amino Acids 17-112)
                                          (SEQ ID NO: 3)
MYVKLISSDGHEFIVKREHALTSGTIKAMLSGPGQFAENETNEVNFREIP

SHVLSKVCMYFTYKVRYTNSSTEIPEFPIAPEIALELLMAANFLDC
```

The N-terminus of VHL contains a six histidine affinity tag for purification purposes.

A VCB-based assay allows a highly sensitive and direct measurement of enzymatic product formation (HIF1α protein or fragments thereof containing a hydroxylated proline residue) and is suitable for high throughput screening.

For expression in *E. coli*, VHL 54-213 was cloned into pAMG21 (Plux promoter) between the NdeI-XhoI site. Immediately downstream of this is the ElonginC gene cloned into the XhoI site to SacII. There is a 13 bp spacer between the stop codon of VHL and the initiating codon of ElonginC. The expression plasmid pAMG21 is a 6118 base pair plasmid that was derived from the expression vector pCFM1656 (ATCC #69576), which in turn can be derived from the expression vector system described in U.S. Pat. No. 4,710,473. This design allows for chemical rather than thermal induction of protein expression by substitution of the promoter region, replacing a synthetic bacteriophage lambda pl promoter with a DNA segment containing the LuxR gene and the LuxPR promoter, and affords regulation of expression by the plasmid-encoded LuxR protein, thereby allowing any *E. coli* strain to serve as host.

ElonginB was cloned into pTA2 (PACYC184.1 based vector) under the control of a Lac promoter. Competent *E. coli* cells were transformed with the pAMG21-VHL-ElonginC construct. These *E. coli* cells were rendered competent again prior to transformation with the pTA2-elonginB construct to produce the final *E. coli* strain containing both plasmid constructs. Induction of protein expression was initiated by the addition of IPTG and N-(3-oxo-hexanoyl)-homoserine lactone (HSL) at 30° C.

Bacterial cells were lysed by a microfluidizer in aqueous buffer of pH 8.0 and the soluble fraction was separated by centrifugation. The soluble *E. coli* fraction was subjected to Nickel-NTA chelating chromatography to utilize the six histidine affinity tag located on the pVHL construct. The pooled fractions from the nickel column were applied to a Superdex 200 size exclusion chromatography (SEC) column. The protein eluted as a monomer on SEC, indicating that the three protein components formed a complex in solution. The fractions from the SEC column were pooled and applied to a Q Sepharose anion exchange column for final purification. The purified complex was visualized by SDS-PAGE and the identities of the three protein components were confirmed by N-terminal amino acid sequencing.

Purified VCB was exchanged into 50 mM sodium carbonate buffer pH 9.2 and labeled with a europium chelate overnight. LANCE™ europium chelate (PerkinElmer, Inc; Eu-W1024 ITC chelate; catalog number is AD0013) was used to label the lysine residues of the VCB complex. The chelate contains an isothiocyanate reactive group that specifically labels proteins on lysine residues (there are fifteen lysine residues in the VCB protein complex). The resulting europylated VCB was purified by desalting columns and quantitated by standard means. The labeling yield was determined to be 6.6 europium groups per one VCB complex.

Two peptides were produced by SynPep, Inc.: a hydroxyproline modified peptide and an unmodified control peptide. VCB was expected to specifically bind to the hydroxyproline modified peptide (a mimic of enzymatic hydroxylation by prolyl hydroxylase). VCB was not expected to bind to the unmodified peptide. Both peptides were produced with a biotin group at the N-terminus to allow for binding by the streptavidin-labeled fluorescent acceptor allophycocyanin (streptavidin APC; Prozyme, Inc.).

The sequence of the custom synthesized HIF1α peptides (amino acids 556-575, with methionine residues replaced with alanine residues to prevent oxidation) were as follows:

(SEQ ID NO: 4)
(unmodified)
Biotin-DLDLEALAPYIPADDDFQLR-CONH$_2$ (SEQ ID NO: 5)
(modified)
Biotin-DLDLEALA[hyP]YIPADDDFQLR-CONH$_2$ The peptides were purchased from SynPep as lyophilized solids and were suspended in DMSO for experimental use. The peptides were quantitated according to their absorbance at 280 nm.

Experiments were conducted in 96 well Costar polystyrene plates. Biotinylated peptides and europylated VCB were suspended in the following buffer: 100 mM HEPES 7.5, 0.1 M NaCl, 0.1% BSA and 0.05% Tween 20. The reagents were allowed to reach equilibrium by shaking for 1 hour before the plates were read on the Discovery Instrument (Packard). The data output is the ratio of the 665 nm and 620 nm emission signal resulting from the 320 nm excitation.

As shown in FIG. 1, the specific interaction of europylated VCB with the hydroxyproline modified HIF1α peptide coupled to streptavidin APC generated a fluorescence signal detectable over the background signal. These results demonstrate a fluorescence signal generated by the specific interaction of Eu-VCB with hyp-HIF1α peptide. Each bar represents the data from a single well of a 96 well assay plate. The signal to background ratio was calculated from data from a control plate (unmodified peptide). Eu-VCB concentration was titrated across rows (nM) and streptavidin APC concentrations were titrated down columns. The peptide concentration was fixed at 100 nM.

Detection of Enzymatically Converted
Hydroxypropyl HIF-1α by HIF PHD2 and Inhibition of HIF PHD2 Activity Binding of the P564-HIF1α peptide to VCB was validated utilizing the homogeneous time-resolved FRET (TR-FRET) technology. A 17 amino acid (17aa) peptide with an N-terminally labeled biotin molecule corresponding to amino acid sequences 558 to 574 of the HIF1α protein was synthesized in-house (DLEMLAPYIPMDDDFQL (SEQ ID NO: 6)). A second 17aa peptide containing a hydroxylated proline at position 564 was chemically generated to mimic the PHD enzyme converted product form of the protein that is recognized by VCB. The assay was performed in a final volume of 100 μL in buffer containing 50 mM Tris-HCl (pH 8), 100 mM NaCl, 0.05% heat inactivated FBS, 0.05% Tween-20, and 0.5% NaN$_3$. The optimal signal over background and the linear range of detection was determined by titrating the hydroxylated or unhydroxylated peptide at varied concentrations between 0 and 1 μM with a titration of VCB-Eu at varying concentrations between 0 and 50 nM with 50 nM of streptavidin APC. The binding reagents were allowed to reach equilibrium by shaking for 1 hour before it was read on the Discovery Instrument (Packard). The data output is the ratio of the 665 nm and 620 nm emission signal resulting from the 320 nm excitation.

HIF PHD2 activity was detected by P564-HIF1α peptide and VCB binding in the TR-FRET format. HIF PHD2 was assayed at various concentrations between 0 and 400 nM with 3 μM HIF1α peptide in buffer containing 50 mM Tris-HCl (pH 7.5), 100 mM NaCl, 0.05% Tween 20, 2 mM 2-oxoglutarate (2-OG), 2 mM ascorbic acid and 100 μM FeCl$_2$ in a final volume of 100 μL. The time-course was determined by periodically transferring 2.5 μL of the reaction into 250 μL of 10×TR-FRET buffer containing 500 mM HEPES (pH 7.5), 1 M NaCl, 1% BSA, and 0.5% Tween-20 to terminate the enzyme reaction. 15 nM HIF-1α peptide from the terminated reaction was added to 35 nM streptavidin-APC and 10 nM VCB-Eu to a final volume of 100 μL in 10×TR-FRET buffer. The TR-FRET reagents were placed on a shaker for 1 hour before detection on the Discovery platform.

Figure 2B:
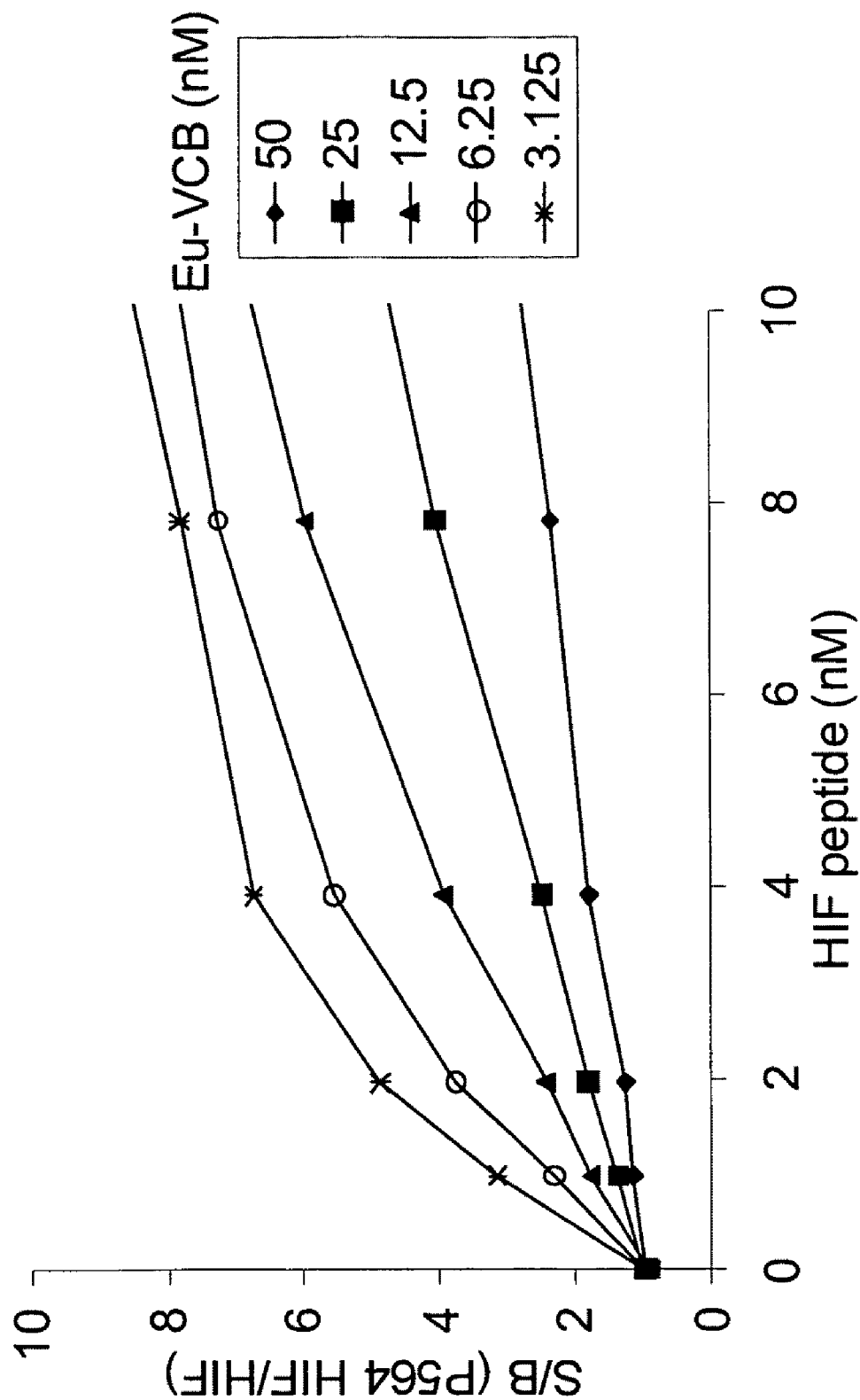

As demonstrated in FIGS. 2A and 2B, there was a dose dependent increase in TR-FRET signal resulting from binding of the hydroxylated-P564-HIF1α peptide to VCB-Eu compared to the unhydroxylated form of the peptide resulting in a 14 fold signal over noise ratio at 125 nM HIF1α peptide. VCB binding to the APC bound peptide permits a FRET transfer between the Eu and APC. The signal was linear to 2 nM peptide with 3.125 nM VCB, but increases to 62.5 nM peptide with 50 nM VCB resulting in a larger linear range.

Figure 3A:
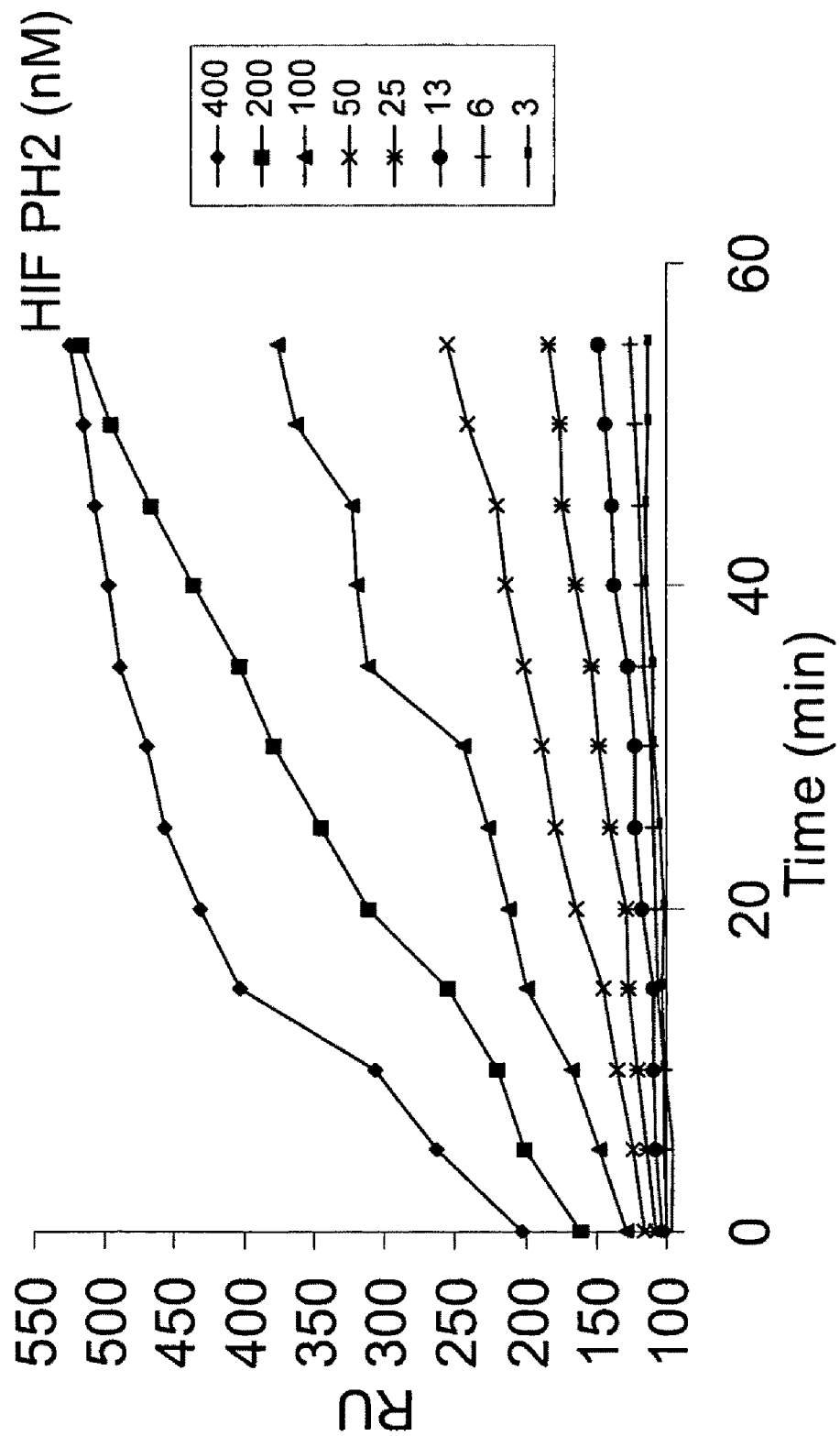
FIGS. 3A and 3B are graphs illustrating VCB binding and TR-FRET detection for determining HIF PHD2 hydroxylation of a HIF1α peptide.
Figure 3B:
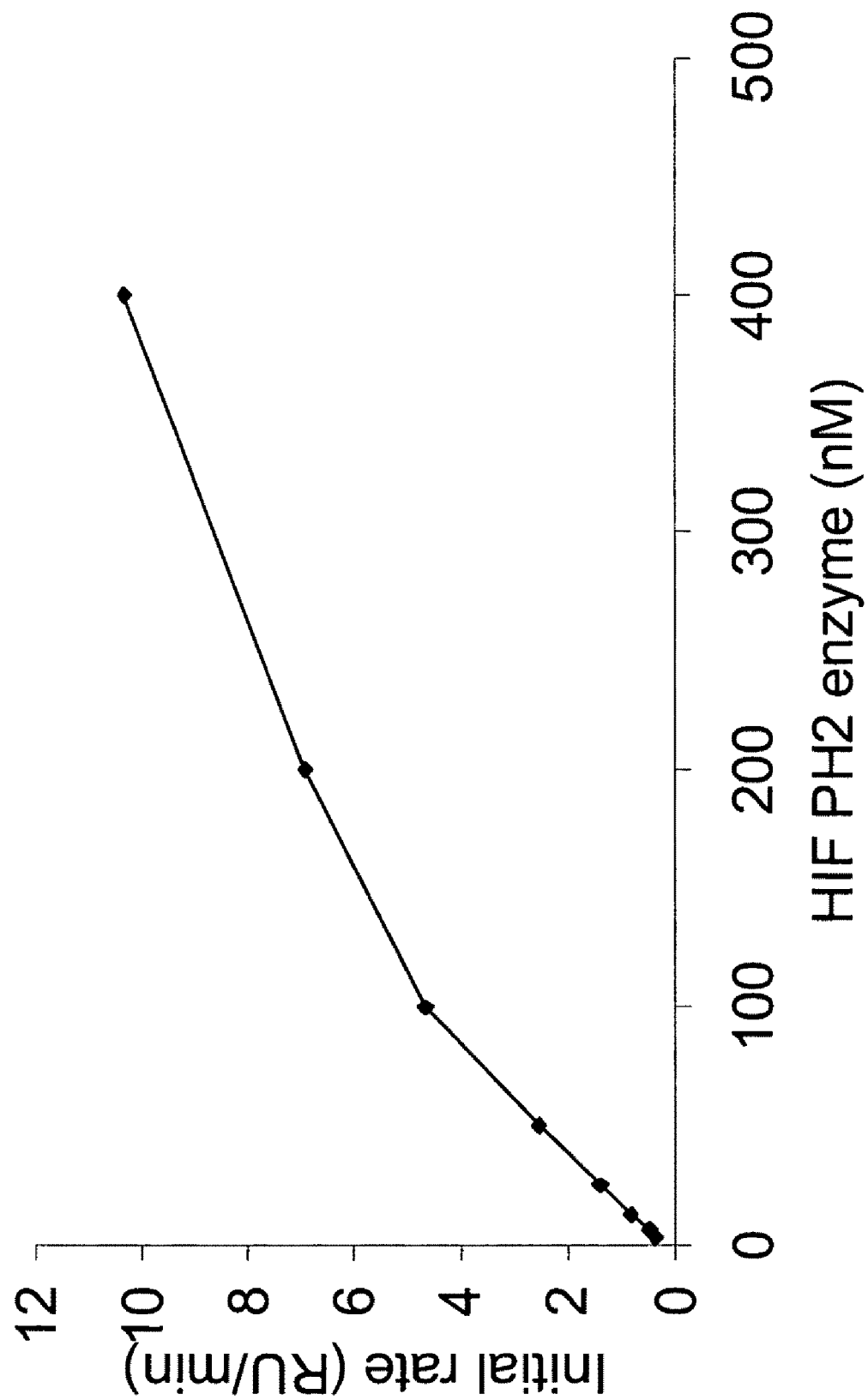

TR-FRET detection utilizing Eu-labeled VCB is a practical system for determining HIF PHD2 catalytic activity. HIF PHD2 hydroxylation of the HIF1α peptide results in the increase affinity of VCB to the peptide and hence and increased FRET signal. As shown in FIGS. 3A and 3B, activity was verified with a fairly linear and an increasing TR-FRET signal over time. There was a dose dependant increase in initial rates with increasing HIF PHD2 enzyme concentration up to 400 nM. The initial rates were linear to 100 nM enzyme.

Inhibition of HIF PHD2 activity was quantified utilizing the TR-FRET technology. HIF PHD2 catalyzes a hydroxyl modification on the proline residue of the P564-HIF1α peptide substrate (Biotin-DLEMLAPYIPMDDDFQL (SEQ ID NO: 7)) resulting in recognition and binding of the europylated Von Hippel-Lindau protein (pVHL), elongin B and elongin C heterotrimeric (VCB-Eu) complex.

The PHD2 inhibition assay was executed by addition of freshly dissolved FeCl$_2$ to 178.57 μM (100 μM final concentration) in PHD2 Reaction Buffer containing 30 mM MES, pH 6, 10 mM NaCl, 0.25% Brij-35, 0.01% BSA, and 1% DMSO. 28 μL of the iron solution and 2 μL of inhibitor compounds serially diluted in 100% DMSO (5% DMSO final) were added to black polypropylene 96-well microtiter plates. To that, 10 μL of 10 nM PHD2 (2 nM final) was added to all wells of the plate except for the 8 wells of column 12 (LO control), and allowed to incubate at room temperature on the shaker for one hour. Column 6 was the HI control containing PHD2 enzyme and 5% DMSO vehicle, but no inhibitor compound. To initiate the PHD2 enzymatic reaction, 10 μL of a solution containing 500 nM P564-HIF1α peptide (100 nM final), 10 mM ascorbic acid (2 mM final), and 1.25 μM 2-oxoglutarate (α-ketoglutarate; 0.25 μM final) in PHD2 Reaction Buffer was added to all wells of the plate and allowed to incubate on the shaker at room temperature for one hour.

The reaction was terminated by addition of 25 μL TR-FRET Buffer (50 mM TRIS-HCl, pH 9, 100 mM NaCl, 0.05% BSA, and 0.5% Tween-20) containing 150 mM succinate (product inhibitor; 50 mM final), 75 nM streptavidin-APC (25 nM final), and 7.5 nM VCB-Eu (2.5 nM final). The TR-FRET detection reagents were placed on a shaker for 1 hour to reach binding equilibrium before reading on the Discovery platform (PerkinElmer). Europium is excited at 315 nm and phosphoresces at 615 nm with a large Stoke's shift. APC, in turn, emits at 655 nm upon excitation at 615 nm. The TR-FRET signal is measured as the ratio of the APC 655 nm signal divided by the internal europium reference 615 nm emission signal.

The POC (percentage of control) was determined by comparing the signal from hydroxylated peptide substrate in the enzyme reaction containing inhibitor compound with that from PHD2 enzyme with DMSO vehicle alone (HI control), and no enzyme (LO control). POC was calculated using the formula: % control (POC)=(cpd−average LO)/(average HI−average LO)*100. Data (consisting of POC and inhibitor concentration in μM) was fitted to a 4-parameter equation $(y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm.

In certain embodiments, compounds of the present invention exhibit a HIF PHD inhibitory activity $IC_{50}$ value of 40 μM or less. In additional embodiments, compounds of the present invention exhibit a HIF PHD inhibitory activity $IC_{50}$ value of 10 μM or less and in further embodiments, compounds of the present invention exhibit a HIP PHD inhibitory activity $IC_{50}$ value of 5 μM or less.

The following table includes PHD2 $IC_{50}$ values obtained using the procedures set forth herein for various Examples compounds described herein.

| Example | Structure | PHD2 $IC_{50}$ (μM) |
|---|---|---|
| 1 | 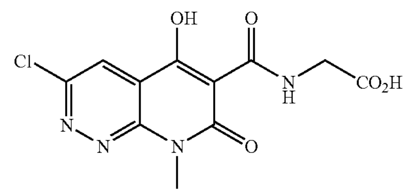 | 0.024 |
| 2 | 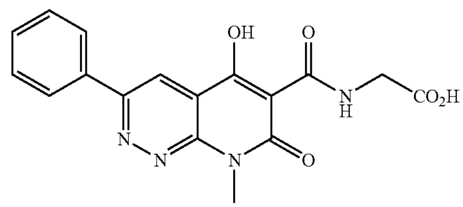 | 0.017 |
| 3 | 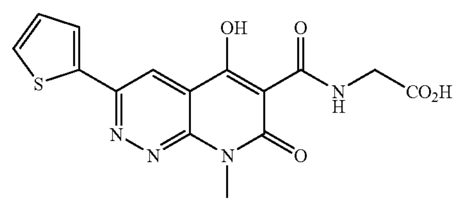 | 0.022 |
| 4 | 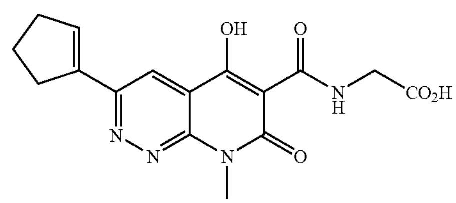 | 0.017 |
| 5 | 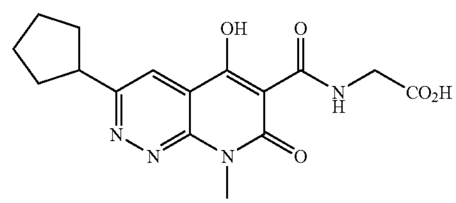 | 0.0088 |

Table of PHD2 $IC_{50}$ values of Example Compounds

Table of PHD2 IC$_{50}$ values of Example Compounds

| Example | Structure | PHD2 IC$_{50}$ (μM) |
|---|---|---|
| 6 | (3-cyclohexenyl-substituted pyrido[2,3-c]pyridazine with 5-OH, 8-methyl, 7-oxo, and 6-carboxamide-N-glycine) | 0.016 |
| 7 | (3-(3-isopropoxyphenyl)-substituted pyrido[2,3-c]pyridazine with 5-OH, 8-methyl, 7-oxo, and 6-carboxamide-N-glycine) | 0.026 |
| 8 | (3-(4-isopropoxyphenyl)-substituted pyrido[2,3-c]pyridazine with 5-OH, 8-methyl, 7-oxo, and 6-carboxamide-N-glycine) | 0.021 |
| 9 | (3-(2-isopropoxyphenyl)-substituted pyrido[2,3-c]pyridazine with 5-OH, 8-methyl, 7-oxo, and 6-carboxamide-N-glycine) | 0.014 |
| 10 | (2-methylthio-pyrimido[4,5-b]pyridine with 5-OH, 8-methyl, 7-oxo, and 6-carboxamide-N-glycine) | 0.025 |
| 11 | (2-piperidinyl-pyrimido[4,5-b]pyridine with 5-OH, 8-methyl, 7-oxo, and 6-carboxamide-N-glycine) | 0.016 |
| 12 | (2-methoxy-pyrimido[4,5-b]pyridine with 4-OH, 8-methyl, 7-oxo, and 6-carboxamide-N-glycine) | 0.018 |

-continued

Table of PHD2 IC$_{50}$ values of Example Compounds

| Example | Structure | PHD2 IC$_{50}$ (μM) |
|---|---|---|
| 13 | 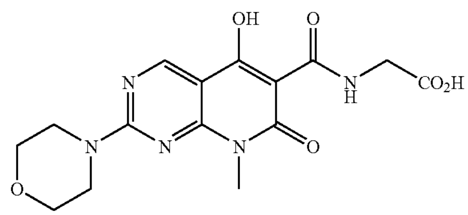 | 0.24 |
| 14 | 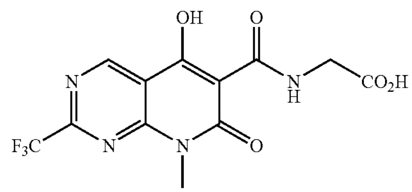 | 0.0069 |
| 15 | 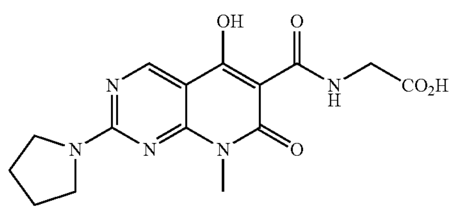 | 0.00735 |
| 16 | 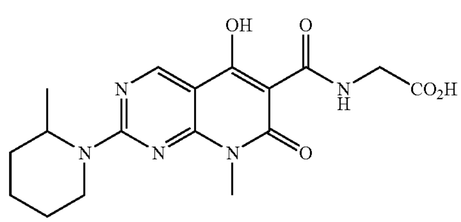 | 0.0525 |
| 17 | 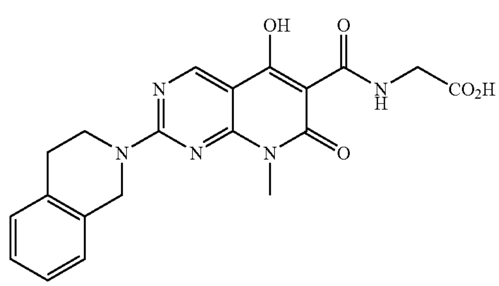 | 0.017 |
| 18 | 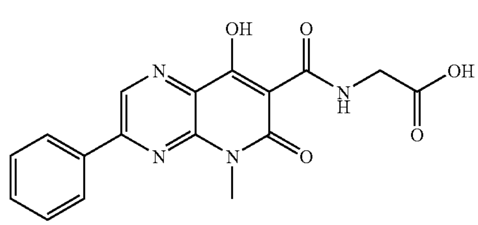 | 0.0088 |

-continued

Table of PHD2 IC$_{50}$ values of Example Compounds

| Example | Structure | PHD2 IC$_{50}$ (μM) |
|---------|-----------|---------------------|
| 19 | 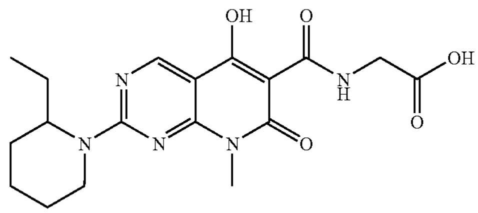 | 0.071 |
| 20 | 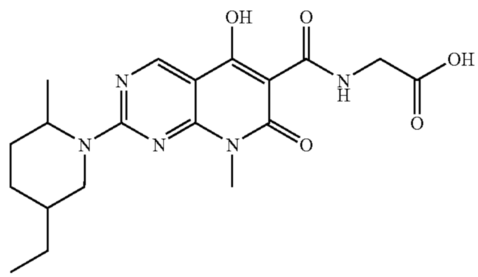 | 0.175 |
| 21 | 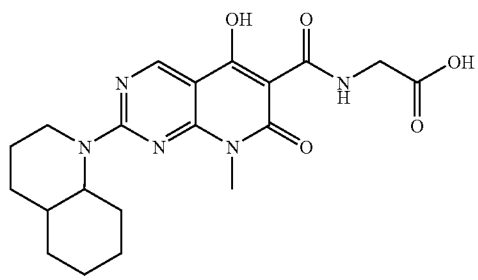 | 0.152 |
| 22 | 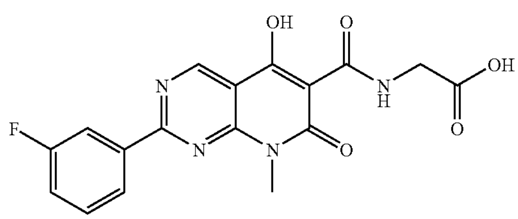 | 0.0029 |
| 23 | 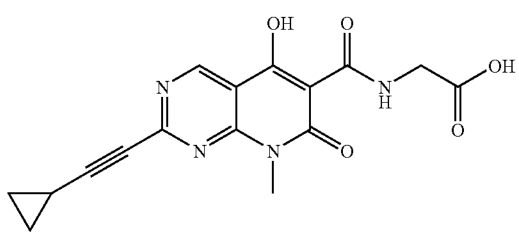 | 0.012 |
| 24 | 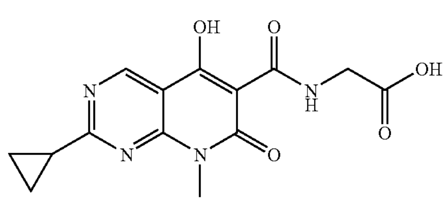 | 0.0039 |

-continued
Table of PHD2 IC$_{50}$ values of Example Compounds
| Example | Structure | PHD2 IC$_{50}$ (μM) |
|---|---|---|
| 25 | 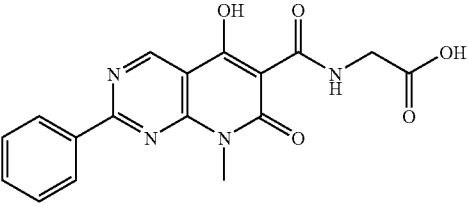 | 0.0043 |
| 26 | 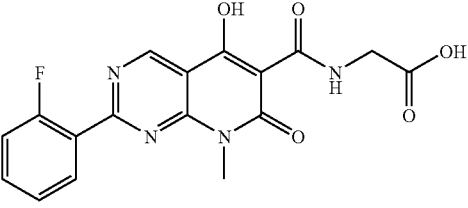 | 0.0015 |
| 27 | 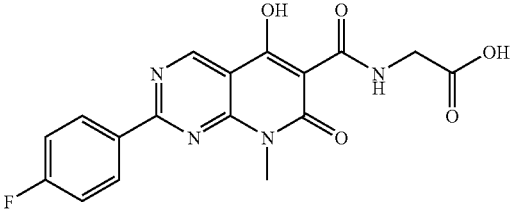 | 0.0023 |
| 28 | 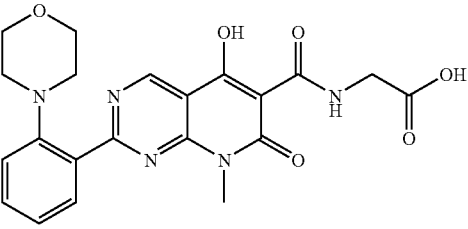 | 0.0029 |
| 29 | 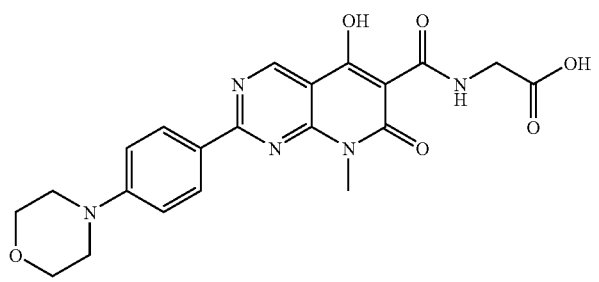 | 0.0037 |
| 30 | 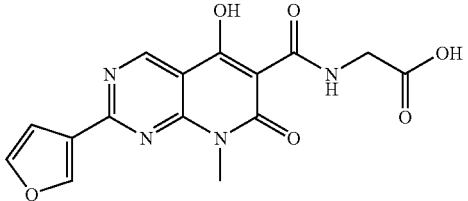 | 0.0053 |

-continued

Table of PHD2 IC$_{50}$ values of Example Compounds

| Example | Structure | PHD2 IC$_{50}$ (μM) |
|---|---|---|
| 31 | 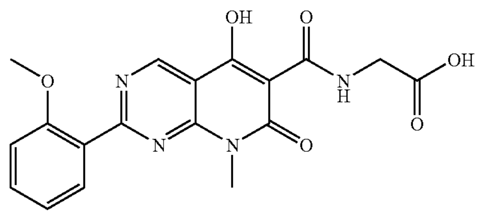 | 0.0024 |
| 32 | 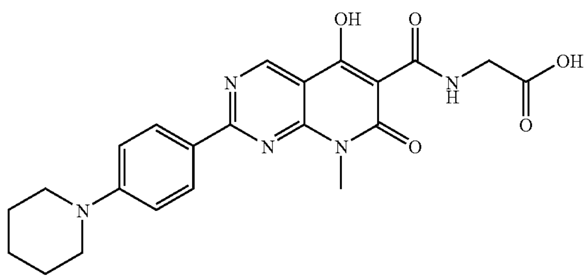 | 0.0053 |
| 33 | 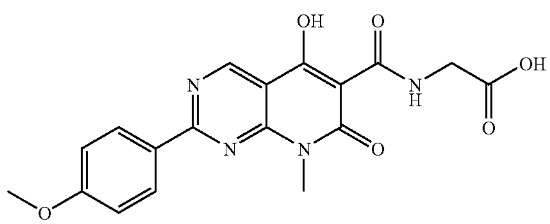 | 0.0064 |
| 34 | 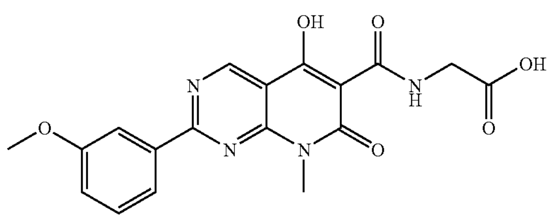 | 0.010 |
| 35 | 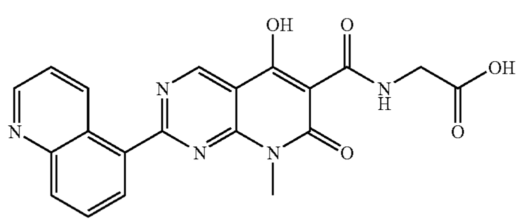 | 0.0024 |
| 36 | 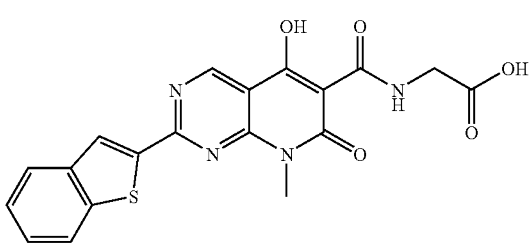 | 0.0074 |

-continued

Table of PHD2 IC$_{50}$ values of Example Compounds

| Example | Structure | PHD2 IC$_{50}$ (μM) |
|---|---|---|
| 37 | 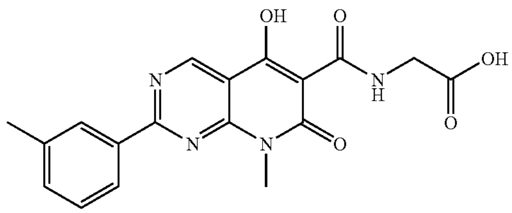 | 0.0088 |
| 38 | 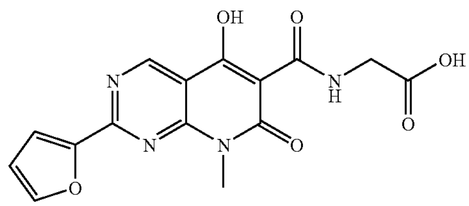 | 0.0025 |
| 39 | 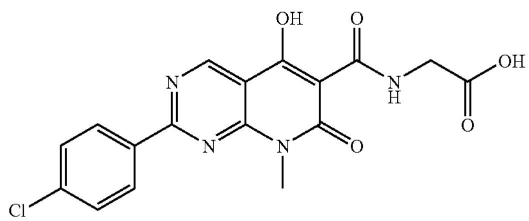 | 0.0078 |
| 40 | 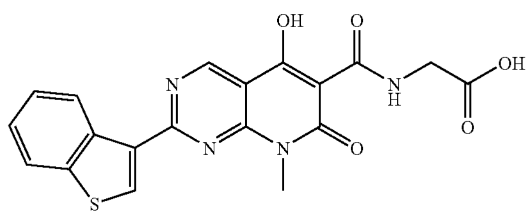 | 0.013 |
| 41 | 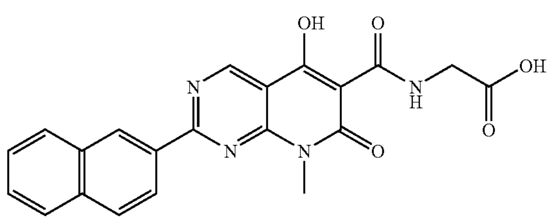 | 0.0094 |
| 42 | 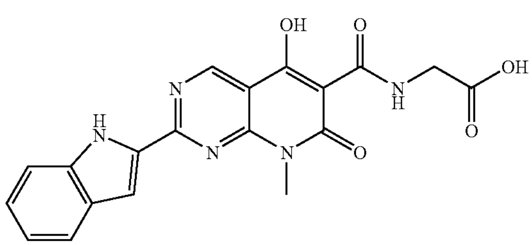 | 0.0031 |
| 43 | 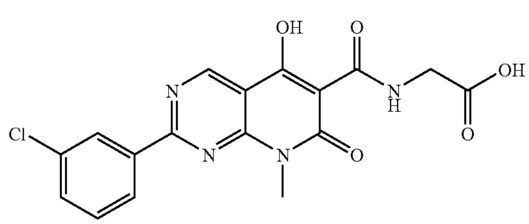 | 0.0079 |

Table of PHD2 IC$_{50}$ values of Example Compounds

| Example | Structure | PHD2 IC$_{50}$ (μM) |
|---|---|---|
| 44 | 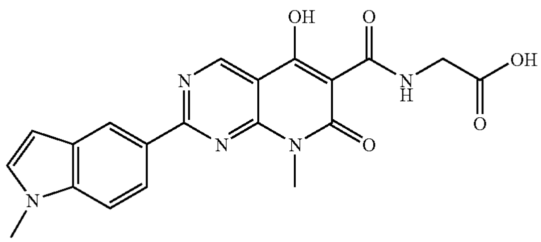 | 0.0078 |
| 45 | 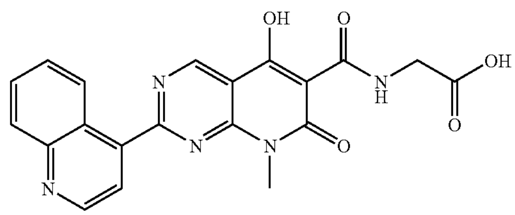 | 0.0020 |
| 46 | 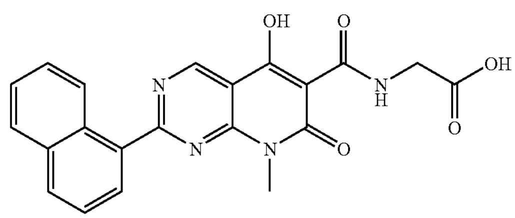 | 0.0023 |
| 47 | 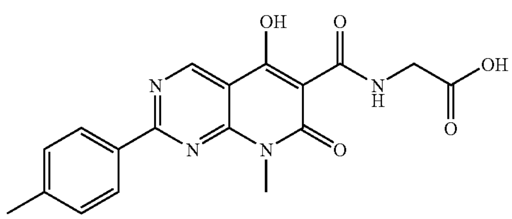 | 0.0067 |
| 48 | 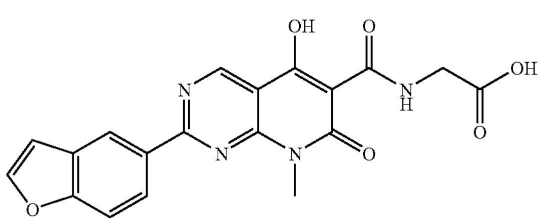 | 0.0071 |
| 49 | 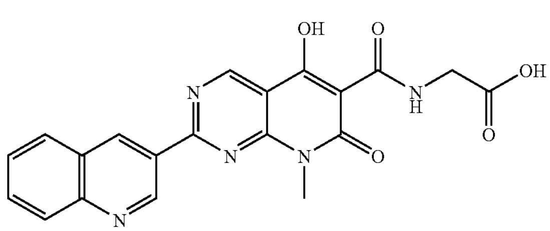 | 0.0032 |

Table of PHD2 IC$_{50}$ values of Example Compounds

| Example | Structure | PHD2 IC$_{50}$ (μM) |
|---|---|---|
| 50 | 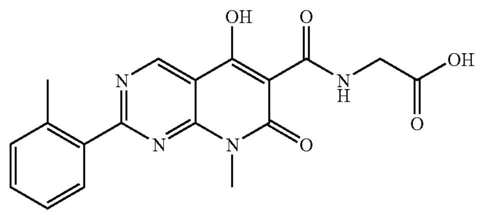 | 0.0036 |
| 51 | 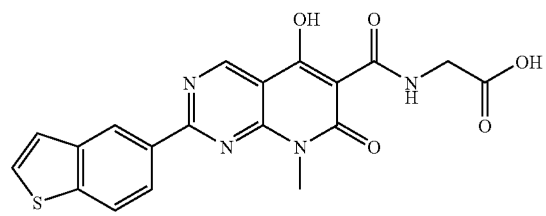 | 0.0094 |
| 52 | 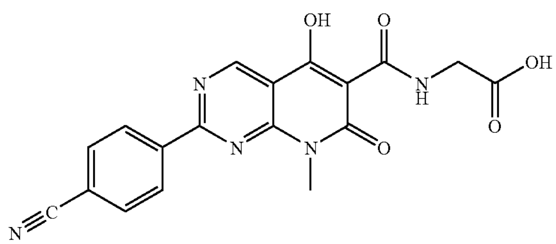 | 0.0041 |
| 53 | 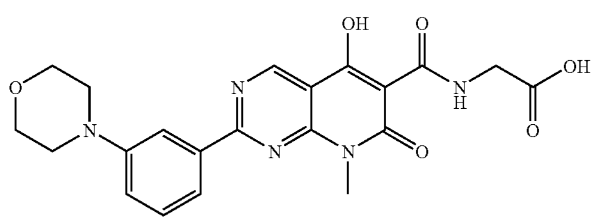 | 0.0050 |
| 54 | 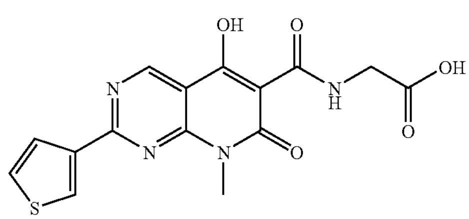 | 0.004 |
| 55 | 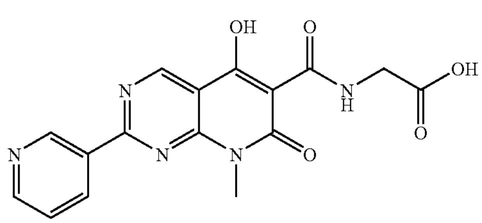 | 0.00445 |

-continued

Table of PHD2 IC$_{50}$ values of Example Compounds

| Example | Structure | PHD2 IC$_{50}$ (μM) |
|---------|-----------|---------------------|
| 56 | 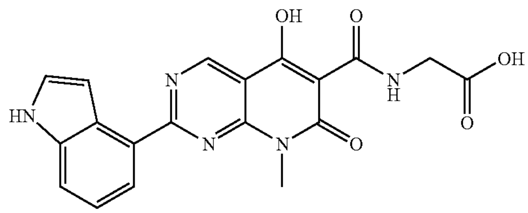 | 0.0053 |
| 57 | 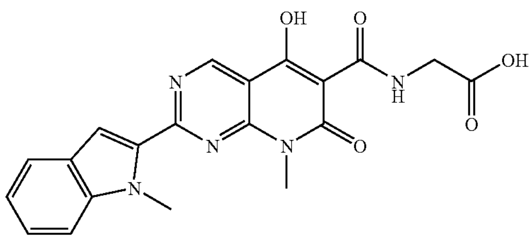 | 0.014 |
| 58 | 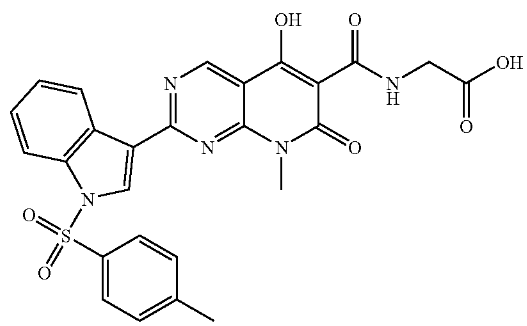 | 0.042 |

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A composition of matter, comprising at least one compound of Formula I:

a pharmaceutically acceptable salt thereof, a tautomer thereof, or a pharmaceutically acceptable salt of the tautomer; or a mixture of any of the foregoing, wherein:

J is $CR_6$;
K is N;
L is $CR_6$;
M is N
n is 1;
$R_1$ and $R_2$ are H;
X is selected from —$NR_a$—, wherein $R_a$ is H;
$R_3$ is selected from OH, SH, $NH_2$, lower alkyl, substituted lower alkyl, lower alkoxy, substituted lower alkoxy, or sulfanyl;
$R_4$ is selected from H, OH, lower alkoxy, SH, $NH_2$, $NHSO_2R_7$, or sulfonyl;
$R_5$ is selected from H, lower alkyl, or substituted lower alkyl;
each $R_6$ is independently selected from H, F, Cl, Br, I, alkyl, substituted alkyl, haloalkyl, perhaloalkyl, alkenyl, substituted alkenyl, alkynyl, substituted alkynyl, $NR_dR_e$, $C(O)R_7$, $C(O)OR_8$, $OR_8$, $SR_8$, $SO_2R_8$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_9$, wherein:
Y is selected from —$N(R_{10})$—Z— or —Z—$N(R_{10})$—;
Z is selected from C(O), $SO_2$, alkylene, substituted alkylene, alkenylene, substituted alkenylene, alkynylene, or substituted alkynylene;
$R_7$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;
$R_8$ is selected from H, alkyl, substituted alkyl, alkenyl, substituted alkenyl, alkynyl, or substituted alkynyl;
$R_9$ is selected from H, heterocyclyl, substituted heterocyclyl, aryl, substituted aryl, heteroaryl, or substituted heteroaryl;
$R_{10}$ is selected from H, lower alkyl, or substituted lower alkyl; and
$R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring.

2. The composition of matter according to claim 1, wherein $R_3$ is OH.

3. The composition of matter according to claim 1, wherein $R_4$ is OH.

4. The composition of matter according to claim 1, wherein at least one instance of $R_6$ is a substituted or unsubstituted aryl, a substituted or unsubstituted heteroaryl, a substituted or unsubstituted cycloalkyl, or a substituted or unsubstituted heterocyclyl group.

5. The composition of matter according to claim 4, wherein at least one instance of $R_6$ is a heterocyclyl group.

6. The composition of matter according to claim 4, wherein at least one instance of $R_6$ is a heteroaryl group.

7. The composition of matter according to claim 4, wherein at least one instance of $R_6$ is a phenyl or substituted phenyl group.

8. The composition of matter according to claim 1, wherein at least one instance of $R_6$ is chosen from a halo or a moiety substituted with at least one halo.

9. The composition of matter according to claim 1, wherein $R_6$ is a group of formula wherein the wavy line indicates the point of attachment to the rest of the molecule.

10. The composition of matter according to claim 1, wherein $R_3$ is OH and $R_4$ is OH.

11. The composition of matter according to claim 1, wherein $R_5$ is H.

12. The composition of matter according to claim 1, wherein $R_5$ is lower alkyl.

13. The composition of matter according to claim 12, wherein $R_5$ is methyl.

14. The composition of matter according to claim 1, wherein $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

15. The composition of matter according to claim 1, wherein the at least one compound is selected from one of the following compounds or is a salt thereof, a tautomer thereof, or a salt of the tautomer:

- 2-(5-hydroxy-8-methyl-2-(methylthio)-7-oxo-7,8-dihydropyrido[2,3-d]pyrimidine-6-carboxamido)acetic acid;
- 2-(5-hydroxy-8-methyl-7-oxo-2-(piperidin-1-yl)-7,8-dihydropyrido[2,3-d]pyrimidine-6-carboxamido)acetic acid;
- 2-(5-hydroxy-2-methoxy-8-methyl-7-oxo-7,8-dihydropyrido[2,3-d]pyrimidine-6-carboxamido)acetic acid;
- 2-(5-hydroxy-8-methyl-2-morpholino-7-oxo-7,8-dihydropyrido[2,3-d]pyrimidine-6-carboxamido)acetic acid;
- 2-(5-hydroxy-8-methyl-7-oxo-2-(trifluoromethyl)-7,8-dihydropyrido[2,3-d]pyrimidine-6-carboxamido)acetic acid;
- 2-(5-hydroxy-8-methyl-7-oxo-2-(pyrrolidin-1-yl)-7,8-dihydropyrido[2,3-d]pyrimidine-6-carboxamido)acetic acid;
- 2-(5-hydroxy-8-methyl-2-(2-methylpiperidin-1-yl)-7-oxo-7,8-dihydropyrido[2,3-d]pyrimidine-6-carboxamido)acetic acid; or
- 2-(2-(3,4-dihydroquinolin-1(2H)-yl)-5-hydroxy-8-methyl-7-oxo-7,8-dihydropyrido[2,3-d]pyrimidine-6-carboxamido)acetic acid.

16. The composition of matter according to claim 1, wherein the at least one compound is selected from one of the following compounds or is a salt thereof, a tautomer thereof, or a salt of the tautomer:

- 2-(2-cyano-5-hydroxy-8-methyl-7-oxo-7,8-dihydropyrido[2,3-d]pyrimidine-6-carboxamido)acetic acid;
- 6-((carboxymethyl)carbamoyl)-5-hydroxy-8-methyl-7-oxo-7,8-dihydropyrido[2,3-d]pyrimidine-2-carboxylic acid;
- 2-(5-hydroxy-2-(isoindolin-2-yl)-8-methyl-7-oxo-7,8-dihydropyrido[2,3-d]pyrimidine-6-carboxamido)acetic acid;
- 2-(2-(benzyloxy)-5-hydroxy-8-methyl-7-oxo-7,8-dihydropyrido[2,3-d]pyrimidine-6-carboxamido)acetic acid;
- 2-(8-benzyl-5-hydroxy-7-oxo-2-(trifluoromethyl)-7,8-dihydropyrido[2,3-d]pyrimidine-6-carboxamido)acetic acid; or
- 2-(5-hydroxy-8-methyl-7-oxo-2-(4-phenylpiperazin-1-yl)-7,8-dihydropyrido[2,3-d]pyrimidine-6-carboxamido)acetic acid.

17. The composition of matter according to claim 1, wherein the at least one compound is selected from one of the following compounds or is a salt thereof, a tautomer thereof, or a salt of the tautomer:

- 2-(2-(2-ethylpiperidin-1-yl)-5-hydroxy-8-methyl-7-oxo-7,8-dihydropyrido[2,3-d]pyrimidine-6-carboxamido)acetic acid;
- 2-(2-(5-ethyl-2-methylpiperidin-1-yl)-5-hydroxy-8-methyl-7-oxo-7,8-dihydropyrido[2,3-d]pyrimidine-6-carboxamido)acetic acid;
- 2-(5-hydroxy-8-methyl-2-(octahydroquinolin-1(2H)-yl)-7-oxo-7,8-dihydropyrido[2,3-d]pyrimidine-6-carboxamido)acetic acid;
- 2-(2-(3-fluorophenyl)-5-hydroxy-8-methyl-7-oxo-7,8-dihydropyrido[2,3-d]pyrimidine-6-carboxamido)acetic acid;
- 2-(2-(2-cyclopropylethynyl)-5-hydroxy-8-methyl-7-oxo-7,8-dihydropyrido[2,3-d]pyrimidine-6-carboxamido)acetic acid;
- 2-(2-cyclopropyl-5-hydroxy-8-methyl-7-oxo-7,8-dihydropyrido[2,3-d]pyrimidine-6-carboxamido)acetic acid;
- 2-(5-hydroxy-8-methyl-7-oxo-2-phenyl-7,8-dihydropyrido[2,3-d]pyrimidine-6-carboxamido)acetic acid;
- 2-(2-(2-fluorophenyl)-5-hydroxy-8-methyl-7-oxo-7,8-dihydropyrido[2,3-d]pyrimidine-6-carboxamido)acetic acid;
- 2-(2-(4-fluorophenyl)-5-hydroxy-8-methyl-7-oxo-7,8-dihydropyrido[2,3-d]pyrimidine-6-carboxamido)acetic acid;
- 2-(5-hydroxy-8-methyl-2-(2-morpholinophenyl)-7-oxo-7,8-dihydropyrido[2,3-d]pyrimidine-6-carboxamido)acetic acid;
- 2-(5-hydroxy-8-methyl-2-(4-morpholinophenyl)-7-oxo-7,8-dihydropyrido[2,3-d]pyrimidine-6-carboxamido)acetic acid;
- 2-(2-(furan-3-yl)-5-hydroxy-8-methyl-7-oxo-7,8-dihydropyrido[2,3-d]pyrimidine-6-carboxamido)acetic acid;
- 2-(5-hydroxy-2-(2-methoxyphenyl)-8-methyl-7-oxo-7,8-dihydropyrido[2,3-d]pyrimidine-6-carboxamido)acetic acid;
- 2-(5-hydroxy-8-methyl-7-oxo-2-(4-(piperidin-1-yl)phenyl)-7,8-dihydropyrido[2,3-d]pyrimidine-6-carboxamido)acetic acid;
- 2-(5-hydroxy-2-(4-methoxyphenyl)-8-methyl-7-oxo-7,8-dihydropyrido[2,3-d]pyrimidine-6-carboxamido)acetic acid;
- 2-(5-hydroxy-2-(3-methoxyphenyl)-8-methyl-7-oxo-7,8-dihydropyrido[2,3-d]pyrimidine-6-carboxamido)acetic acid;
- 2-(5-hydroxy-8-methyl-7-oxo-2-(quinolin-5-yl)-7,8-dihydropyrido[2,3-d]pyrimidine-6-carboxamido)acetic acid;
- 2-(2-(benzo[b]thiophen-2-yl)-5-hydroxy-8-methyl-7-oxo-7,8-dihydropyrido[2,3-d]pyrimidine-6-carboxamido)acetic acid;
- 2-(5-hydroxy-8-methyl-7-oxo-2-m-tolyl-7,8-dihydropyrido[2,3-d]pyrimidine-6-carboxamido)acetic acid;
- 2-(2-(furan-2-yl)-5-hydroxy-8-methyl-7-oxo-7,8-dihydropyrido[2,3-d]pyrimidine-6-carboxamido)acetic acid;
- 2-(2-(4-chlorophenyl)-5-hydroxy-8-methyl-7-oxo-7,8-dihydropyrido[2,3-d]pyrimidine-6-carboxamido)acetic acid;
- 2-(2-(benzo[b]thiophen-3-yl)-5-hydroxy-8-methyl-7-oxo-7,8-dihydropyrido[2,3-d]pyrimidine-6-carboxamido)acetic acid;
- 2-(5-hydroxy-8-methyl-2-(naphthalen-2-yl)-7-oxo-7,8-dihydropyrido[2,3-d]pyrimidine-6-carboxamido)acetic acid;
- 2-(5-hydroxy-2-(1H-indol-2-yl)-8-methyl-7-oxo-7,8-dihydropyrido[2,3-d]pyrimidine-6-carboxamido)acetic acid;
- 2-(2-(3-chlorophenyl)-5-hydroxy-8-methyl-7-oxo-7,8-dihydropyrido[2,3-d]pyrimidine-6-carboxamido)acetic acid;

2-(5-hydroxy-8-methyl-2-(1-methyl-1H-indol-5-yl)-7-oxo-7,8-dihydropyrido[2,3-d]pyrimidine-6-carboxamido)acetic acid;

2-(5-hydroxy-8-methyl-7-oxo-2-(quinolin-4-yl)-7,8-dihydropyrido[2,3-d]pyrimidine-6-carboxamido)acetic acid;

2-(5-hydroxy-8-methyl-2-(naphthalen-1-yl)-7-oxo-7,8-dihydropyrido[2,3-d]pyrimidine-6-carboxamido)acetic acid;

2-(5-hydroxy-8-methyl-7-oxo-2-p-tolyl-7,8-dihydropyrido[2,3-d]pyrimidine-6-carboxamido)acetic acid;

2-(2-(benzofuran-5-yl)-5-hydroxy-8-methyl-7-oxo-7,8-dihydropyrido[2,3-d]pyrimidine-6-carboxamido)acetic acid;

2-(5-hydroxy-8-methyl-7-oxo-2-(quinolin-3-yl)-7,8-dihydropyrido[2,3-d]pyrimidine-6-carboxamido)acetic acid;

2-(5-hydroxy-8-methyl-7-oxo-2-o-tolyl-7,8-dihydropyrido[2,3-d]pyrimidine-6-carboxamido)acetic acid;

2-(2-(benzo[b]thiophen-5-yl)-5-hydroxy-8-methyl-7-oxo-7,8-dihydropyrido[2,3-d]pyrimidine-6-carboxamido)acetic acid;

2-(2-(4-cyanophenyl)-5-hydroxy-8-methyl-7-oxo-7,8-dihydropyrido[2,3-d]pyrimidine-6-carboxamido)acetic acid;

2-(5-hydroxy-8-methyl-2-(3-morpholinophenyl)-7-oxo-7,8-dihydropyrido[2,3-d]pyrimidine-6-carboxamido)acetic acid;

2-(5-hydroxy-8-methyl-7-oxo-2-(thiophen-3-yl)-7,8-dihydropyrido[2,3-d]pyrimidine-6-carboxamido)acetic acid;

2-(5-hydroxy-8-methyl-7-oxo-2-(pyridin-3-yl)-7,8-dihydropyrido[2,3-d]pyrimidine-6-carboxamido)acetic acid;

2-(5-hydroxy-2-(1H-indol-4-yl)-8-methyl-7-oxo-7,8-dihydropyrido[2,3-d]pyrimidine-6-carboxamido)acetic acid;

2-(5-hydroxy-8-methyl-2-(1-methyl-1H-indol-2-yl)-7-oxo-7,8-dihydropyrido[2,3-d]pyrimidine-6-carboxamido)acetic acid; or 2-(5-hydroxy-8-methyl-7-oxo-2-(1-tosyl-1H-indol-3-yl)-7,8-dihydropyrido[2,3-d]pyrimidine-6-carboxamido)acetic acid.

18. A pharmaceutical formulation comprising at least one pharmaceutically acceptable excipient, and a therapeutically effective amount of the composition of matter according to claim 1.

19. The pharmaceutical formulation of claim 18, wherein the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

20. A composition of matter, comprising at least one compound of Formula I:

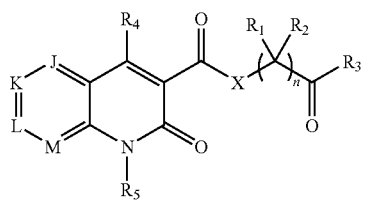

I a pharmaceutically acceptable salt thereof, a tautomer thereof, or a pharmaceutically acceptable salt of the tautomer; or a mixture of any of the foregoing, wherein:

J is $CR_6$;
K is N;
L is $CR_6$;
M is N
n is 1 to 6;
$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;
X is selected from —$NR_a$—, —O—, or —S—, wherein $R_a$ is selected from H or lower alkyl;
$R_3$ is selected from OH, SH, $NH_2$, lower alkyl, substituted lower alkyl, lower alkoxy, substituted lower alkoxy, or sulfanyl;
$R_4$ is selected from H, OH, lower alkoxy, SH, $NH_2$, $NHSO_2R_7$, or sulfonyl;
$R_5$ is selected from H, lower alkyl, or substituted lower alkyl;
each $R_6$ is independently selected from H, F, Cl, Br, I, alkyl, substituted alkyl, haloalkyl, perhaloalkyl, alkenyl, substituted alkenyl, alkynyl, substituted alkynyl, $NR_dR_e$, $C(O)R_7$, $C(O)OR_8$, $OR_8$, $SR_8$, $SO_2R_8$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—$R_9$, wherein:
Y is selected from —$N(R_{10})$—Z— or —Z—$N(R_{10})$—;
Z is selected from C(O), $SO_2$, alkylene, substituted alkylene, alkenylene, substituted alkenylene, alkynylene, or substituted alkynylene;
$R_7$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;
$R_8$ is selected from H, alkyl, substituted alkyl, alkenyl, substituted alkenyl, alkynyl, or substituted alkynyl;
$R_9$ is selected from H, heterocyclyl, substituted heterocyclyl, aryl, substituted aryl, heteroaryl, or substituted heteroaryl;
$R_{10}$ is selected from H, lower alkyl, or substituted lower alkyl; and
$R_d$ and $R_e$ are independently selected from H, lower alkyl, substituted lower alkyl, lower haloalkyl, or substituted lower haloalkyl, or $R_d$ and $R_e$ can join together to form a 3 to 6 membered ring or a substituted 3 to 6 membered ring,
wherein $R_1$ and $R_2$ are not both H if X is —$NR_a$—; $R_a$ is H; and n is 1.

21. The composition of matter according to claim 20, wherein $R_3$ is OH.

22. The composition of matter according to claim 20, wherein $R_4$ is OH.

23. The composition of matter according to claim 20, wherein X is —$NR_a$—.

24. The composition of matter according to claim 23, wherein X is —NH—.

25. The composition of matter according to claim 20, wherein at least one instance of $R_6$ is a substituted or unsubstituted aryl, a substituted or unsubstituted heteroaryl, a substituted or unsubstituted cycloalkyl, or a substituted or unsubstituted heterocyclyl group.

26. The composition of matter according to claim 25, wherein at least one instance of $R_6$ is a heterocyclyl group.

27. The composition of matter according to claim 25, wherein at least one instance of $R_6$ is a heteroaryl group.

28. The composition of matter according to claim 25, wherein at least one instance of $R_6$ is a phenyl or substituted phenyl group.

29. The composition of matter according to claim 20, wherein at least one instance of $R_6$ is chosen from a halo or a moiety substituted with at least one halo.

30. The composition of matter according to claim 20, wherein $R_6$ is selected from —Cl, —$CF_3$, —SMe, —OMe, or a group having the formula

[structures shown]

wherein the wavy line indicates the point of attachment to the rest of the molecule.

31. The composition of matter according to claim 20, wherein n is 1.

32. The composition of matter according to claim 20, wherein $R_1$ and $R_2$ are independently chosen from H and lower alkyl.

33. The composition of matter according to claim 32, wherein $R_1$ and $R_2$ are independently chosen from H and methyl.

34. The composition of matter according to claim 32, wherein $R_1$ and $R_2$ are both H.

35. The composition of matter according to claim 20, wherein $R_3$ is OH; $R_4$ is OH; X is —$NR_a$—; and $R_a$ is H.

36. The composition of matter according to claim 20, wherein $R_5$ is H.

37. The composition of matter according to claim 20, wherein $R_5$ is lower alkyl.

38. The composition of matter according to claim 37, wherein $R_5$ is methyl.

39. The composition of matter according to claim 20, wherein $R_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

40. The composition of matter according to claim 20, wherein at least one of $R_1$ and $R_2$ is not H.

41. A pharmaceutical formulation comprising at least one pharmaceutically acceptable excipient, and a therapeutically effective amount of the composition of matter according to claim 20.

42. The pharmaceutical formulation of claim 41, wherein the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

43. The composition of matter according to claim 1, wherein at least one of $R_1$ and $R_2$ is not H.

44. A composition of matter, comprising at least one compound of Formula I:

[structure of Formula I]

a pharmaceutically acceptable salt thereof, a tautomer thereof, or a pharmaceutically acceptable salt of the tautomer; or a mixture of any of the foregoing, wherein:

J is $CR_6$;
K is N;
L is $CR_6$;
M is N
n is 1 to 6;
$R_1$ and $R_2$ are independently selected in each instance from H, lower alkyl, substituted lower alkyl, lower haloalkyl, or substituted lower haloalkyl, or $R_1$ and $R_2$ can join together to form a 3 to 6 membered ring or a substituted 3 to 6 membered ring;
X is selected from —$NR_a$—, —O—, or —S—, wherein $R_a$ is selected from H or lower alkyl;
$R_3$ is selected from OH, SH, $NH_2$, lower alkyl, substituted lower alkyl, lower alkoxy, substituted lower alkoxy, or sulfanyl;
$R_4$ is selected from H, OH, lower alkoxy, SH, $NH_2$, $NHSO_2R_7$, or sulfonyl;
$R_5$ is selected from H, lower alkyl, or substituted lower alkyl;
each $R_6$ is independently selected from H, F, Cl, Br, I, alkyl, substituted alkyl, haloalkyl, perhaloalkyl, alkenyl, substituted alkenyl, alkynyl, substituted alkynyl, $NR_aR_e$, C(O)R$_7$, C(O)OR$_8$, OR$_8$, SR$_8$, SO$_2$R$_8$, CN, NO$_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, or —Y—R$_9$, wherein:

Y is selected from —N(R$_{10}$)—Z— or —Z—N(R$_{10}$)—;

Z is selected from C(O), SO$_2$, alkylene, substituted alkylene, alkenylene, substituted alkenylene, alkynylene, or substituted alkynylene;

R$_7$ is selected from H, alkyl, substituted alkyl, alkenyl, substituted alkenyl, alkynyl, substituted alkynyl heterocyclyl, substituted heterocyclyl, aryl, substituted aryl, heteroaryl, or substituted heteroaryl;

R$_8$ is selected from H, alkyl, substituted alkyl, alkenyl, substituted alkenyl, alkynyl, or substituted alkynyl;

R$_9$ is selected from H, heterocyclyl, substituted heterocyclyl, aryl, substituted aryl, heteroaryl, or substituted heteroaryl;

R$_{10}$ is selected from H, lower alkyl, or substituted lower alkyl; and

R$_d$ and R$_e$ are independently selected from H, lower alkyl, substituted lower alkyl, lower haloalkyl, or substituted lower haloalkyl, or R$_d$ and R$_e$ can join together to form a 3 to 6 membered ring or a substituted 3 to 6 membered ring, wherein one instance of R$_6$ is selected from a group having the formula

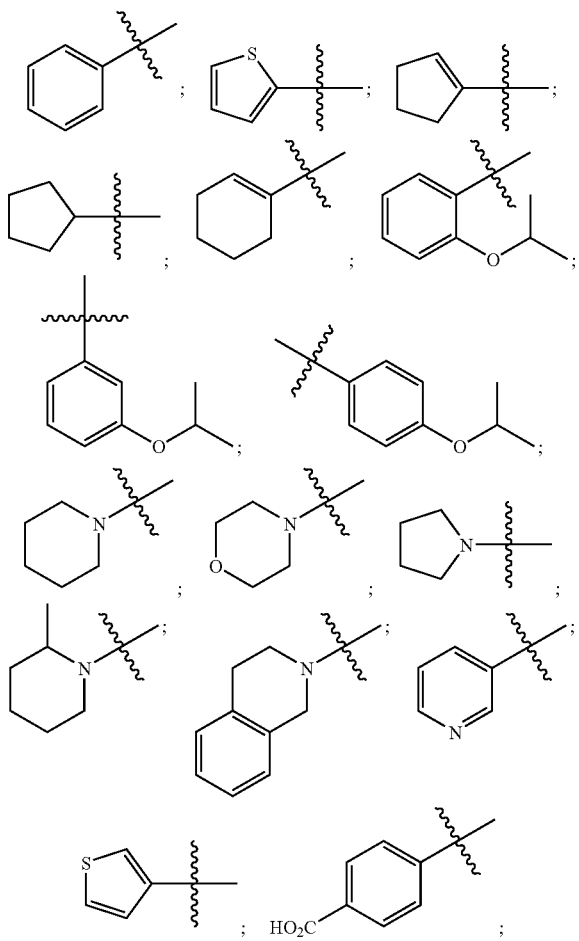

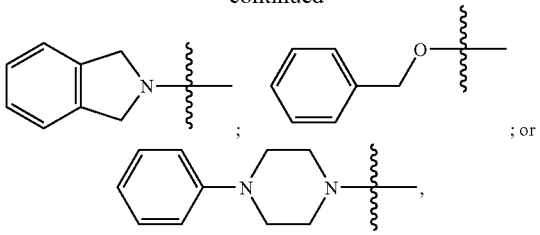

wherein the wavy line indicates the point of attachment to the rest of the molecule.

45. The composition of matter according to claim 44, wherein R$_3$ is OH.

46. The composition of matter according to claim 44, wherein R$_4$ is OH.

47. The composition of matter according to claim 44, wherein X is —NR$_a$—.

48. The composition of matter according to claim 47, wherein X is —NH—.

49. The composition of matter according to claim 44, wherein n is 1.

50. The composition of matter according to claim 44, wherein R$_1$ and R$_2$ are independently chosen from H and lower alkyl.

51. The composition of matter according to claim 50, wherein R$_1$ and R$_2$ are independently chosen from H and methyl.

52. The composition of matter according to claim 50, wherein R$_1$ and R$_2$ are both H.

53. The composition of matter according to claim 44, wherein n is 1; R$_1$ is H or lower alkyl; R$_2$ is H; R$_3$ is OH; R$_4$ is OH; X is —NR$_a$—; and R$_a$ is H.

54. The composition of matter according to claim 44, wherein R$_5$ is H.

55. The composition of matter according to claim 44, wherein R$_5$ is lower alkyl.

56. The composition of matter according to claim 55, wherein R$_5$ is methyl.

57. The composition of matter according to claim 44, wherein R$_5$ is a substituted lower alkyl selected from an arylalkyl, a heteroarylalkyl, a heterocyclylalkyl, a cycloalkylalkyl, a hydroxyalkyl, an alkoxyalkyl, or a haloalkyl.

58. The composition of matter according to claim 44, wherein R$_1$ and R$_2$ are not both H if X is —NR$_a$—; R$_a$ is H; and n is 1.

59. The composition of matter according to claim 44, wherein n is 1, R$_1$ and R$_2$ are both H, X is —NR$_a$—; and R$_a$ is H.

60. The composition of matter according to claim 1, wherein at least one of R$_1$ and R$_2$ is not H.

61. A pharmaceutical formulation comprising at least one pharmaceutically acceptable excipient, and a therapeutically effective amount of the composition of matter according to claim 44.

62. The pharmaceutical formulation of claim 61, wherein the composition of matter is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

* * * * *

SEQUENCE LISTING

<160> NUMBER OF SEQ ID NOS: 7

<210> SEQ ID NO 1
<211> LENGTH: 166
<212> TYPE: PRT
<213> ORGANISM: Homo sapiens

<400> SEQUENCE: 1

Met His His His His His His Glu Ala Gly Arg Pro Arg Pro Val Leu
1               5                   10                  15

Arg Ser Val Asn Ser Arg Glu Pro Ser Gln Val Ile Phe Cys Asn Arg
            20                  25                  30

Ser Pro Arg Val Val Leu Pro Val Trp Leu Asn Phe Asp Gly Glu Pro
        35                  40                  45

Gln Pro Tyr Pro Thr Leu Pro Pro Gly Thr Gly Arg Arg Ile His Ser
    50                  55                  60

Tyr Arg Gly His Leu Trp Leu Phe Arg Asp Ala Gly Thr His Asp Gly
65                  70                  75                  80

Leu Leu Val Asn Gln Thr Glu Leu Phe Val Pro Ser Leu Asn Val Asp
            85                  90                  95

Gly Gln Pro Ile Phe Ala Asn Ile Thr Leu Pro Val Tyr Thr Leu Lys
            100                 105                 110

Glu Arg Cys Leu Gln Val Val Arg Ser Leu Val Lys Pro Glu Asn Tyr
            115                 120                 125

Arg Arg Leu Asp Ile Val Arg Ser Leu Tyr Glu Asp Leu Glu Asp His
130                 135                 140

Pro Asn Val Gln Lys Asp Leu Glu Arg Leu Thr Gln Glu Arg Ile Ala
145                 150                 155                 160

His Gln Arg Met Gly Asp
            165

<210> SEQ ID NO 2
<211> LENGTH: 118
<212> TYPE: PRT
<213> ORGANISM: Homo sapiens

<400> SEQUENCE: 2

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
            20                  25                  30

Gly Ile Leu Lys Arg Pro Pro Asp Glu Gln Arg Leu Tyr Lys Asp Asp
            35                  40                  45

Gln Leu Leu Asp Asp Gly Lys Thr Leu Gly Glu Cys Gly Phe Thr Ser
50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
            85                  90                  95

Pro Glu Leu Pro Asp Val Met Lys Pro Gln Asp Ser Gly Ser Ser Ala
            100                 105                 110

Asn Glu Gln Ala Val Gln
            115

<210> SEQ ID NO 3
<211> LENGTH: 96
<212> TYPE: PRT
<213> ORGANISM: Homo sapiens

<400> SEQUENCE: 3

Met Tyr Val Lys Leu Ile Ser Ser Asp Gly His Glu Phe Ile Val Lys
1               5                   10                  15

Arg Glu His Ala Leu Thr Ser Gly Thr Ile Lys Ala Met Leu Ser Gly
            20                  25                  30

Pro Gly Gln Phe Ala Glu Asn Glu Thr Asn Glu Val Asn Phe Arg Glu
            35                  40                  45

Ile Pro Ser His Val Leu Ser Lys Val Cys Met Tyr Phe Thr Tyr Lys
50                  55                  60

Val Arg Tyr Thr Asn Ser Ser Thr Glu Ile Pro Glu Phe Pro Ile Ala
65                  70                  75                  80

Pro Glu Ile Ala Leu Glu Leu Leu Met Ala Ala Asn Phe Leu Asp Cys
            85                  90                  95

```
<210> SEQ ID NO 4
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (20)..(20)
<223> OTHER INFORMATION: Carboxylation

<400> SEQUENCE: 4

Asp Leu Asp Leu Glu Ala Leu Ala Pro Tyr Ile Pro Ala Asp Asp Asp
1               5                   10                  15

Phe Gln Leu Arg
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (9)..(9)
<223> OTHER INFORMATION: Xaa at position 9 is hydroxyproline
<220> FEATURE:
<221> NAME/KEY: MISC_FEATURE
<222> LOCATION: (20)..(20)
<223> OTHER INFORMATION: Carboxyamidated

<400> SEQUENCE: 5

Asp Leu Asp Leu Glu Ala Leu Ala Xaa Tyr Ile Pro Ala Asp Asp Asp
1               5                   10                  15

Phe Gln Leu Arg
            20

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Asp Leu Glu Met Leu Ala Pro Tyr Ile Pro Met Asp Asp Asp Phe Gln
1               5                   10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
```

```
<400> SEQUENCE: 7

Asp Leu Glu Met Leu Ala Pro Tyr Ile Pro Met Asp Asp Asp Phe Gln
1               5                   10                  15
Leu
```